US009217010B2

(12) United States Patent
Cushman et al.

(10) Patent No.: US 9,217,010 B2
(45) Date of Patent: Dec. 22, 2015

(54) N-SUBSTITUTED INDENOISOQUINOLINES AND SYNTHESES THEREOF

(71) Applicants: PURDUE RESEARCH FOUNDATION, West Lafayette, IN (US); THE UNITED STATES OF AMERICA AS REPRESENTED BY THE SECRETARY, DEPARTMENT OF HEALTH AND HUMAN SERVICES, Washington, DC (US)

(72) Inventors: Mark S. Cushman, West Lafayette, IN (US); Andrew E. Morrell, San Diego, CA (US); Muthukaman Nagarajan, Hyderabad (IN); Yves G. Pommier, Bethesda, MD (US); Keli K. Agama, Germantown, MD (US); Smitha Antony, Silver Springs, MD (US); Daniel E. Beck, Lafayette, IN (US)

(73) Assignees: PURDUE RESEARCH FOUNDATION, West Lafayette, IN (US); THE UNITED STATES OF AMERICA AS REPRESENTED BY THE SECRETARY OF THE DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 14/339,766

(22) Filed: Jul. 24, 2014

(65) Prior Publication Data
US 2014/0336188 A1 Nov. 13, 2014

Related U.S. Application Data

(63) Continuation of application No. 13/317,153, filed on Oct. 11, 2011, now Pat. No. 8,829,022, which is a continuation of application No. 12/093,398, filed as application No. PCT/US2006/043933 on Nov. 13, 2006, now Pat. No. 8,053,443.

(60) Provisional application No. 60/808,699, filed on May 26, 2006, provisional application No. 60/736,471, filed on Nov. 14, 2005.

(51) Int. Cl.
C07D 221/18 (2006.01)
C07J 73/00 (2006.01)
A61K 31/473 (2006.01)
A61K 31/4741 (2006.01)

(52) U.S. Cl.
CPC .............. *C07J 73/005* (2013.01); *A61K 31/473* (2013.01); *A61K 31/4741* (2013.01); *C07D 221/18* (2013.01); *C07J 73/003* (2013.01)

(58) Field of Classification Search
None
See application file for complete search history.

(56) References Cited

U.S. PATENT DOCUMENTS

| 5,597,831 | A | 1/1997 | Michalsky et al. |
| 6,509,344 | B1 | 1/2003 | Cushman et al. |
| 7,312,228 | B2 | 12/2007 | Cushman et al. |
| 7,495,100 | B2 | 2/2009 | Cushman et al. |
| 7,781,445 | B2 | 8/2010 | Cushman et al. |
| 8,053,443 | B2 | 11/2011 | Cushman et al. |
| 2004/0229895 | A1 | 11/2004 | Jagtap et al. |
| 2008/0262016 | A1 | 10/2008 | Jagtap et al. |
| 2008/0318995 | A1 | 12/2008 | Cushman et al. |

FOREIGN PATENT DOCUMENTS

| WO | WO00/21537 | 4/2000 |
| WO | WO2004/014862 | 4/2004 |

OTHER PUBLICATIONS

Morrell, et al., Evaluation of indenoisoquinoline topoisomerase I inhibitors using a hollow fiber assay, Bioorganic & Medicinal Chemistry Letters, Jun. 5, 2006, vol. 16, No, 16, p. 4395-4399.
Nagarajan, et al., Synthesis and Evaluation of Indenoisoquinoline Topoisomerase I Inhibitors Substituted with Nitrogen Heterocycles, Journal of Medicinal Chemistry, Sep. 26, 2006, vol. 49, No. 21, p. 6283-6289.
Morrell, et al., A Systematic Study of Nitrated Indenoisoquinolines Reveals a Potent Topoisomerase I Inhibitor, Journal of Medicinal Chemistry, Nov. 24, 2006, vol. 49, p. 7740-7753.
International Search Report and Written Opinion for PCT/US2006/043933 filed Nov. 13, 2006.
Kucerova, T., et al., "Solovolysis of 0-acyl-10hydroxy-10dihydroindeno[1,2-c]Isoquinolin-5,11-diones", 1979, Database CA, Chemical Abstracts Service, Database Accession No. 1980:22814.
Cushman, Mark, et al., "Synthesis of a New Indeno[1,2-c]Isoquinolines: Cytotoxic Non-Camptothecin Topoisomerase I Inhibitors", 2000, Journal of Medicinal Chemistry, vol. 43, No. 20, pp. 3688-3698.
Jayaraman, Muthusamy, et al., "Synthesis of New Dihydroindeno[1-2-c]Isoquinolone and Indenoisoquinolinium Chloride Topoisomerase I Inhibitors Having High In Vivo Anticancer Activity in the Hollow Fiber Animal Model", 2002, *Journal of Medicinal Chemistry*, vol. 45, No. 1, pp. 242-249.
Morrell, Andrew, et al., "Synthesis, of Nitrated Indenoisoquinolines as Topoisomerase I Inhibitors", 2004, Bioorganic & Medicinal Chemistry Letters, vol. 14, pp. 3659-3663.

(Continued)

Primary Examiner — Zinna Northington Davis
(74) Attorney, Agent, or Firm — Mark S. Cohen; Pearl Cohen Zedek Latzer Baratz LLP

(57) ABSTRACT

N-Substituted indenoisoquinoline compounds, and pharmaceutical formulations of N-substituted indenoisoquinoline compounds are described. Also described are processes for preparing N-substituted indenoisoquinoline compounds. Also described are methods for treating cancer in mammals using the described N-substituted indenoisoquinoline compounds or pharmaceutical formulations thereof.

3 Claims, No Drawings

(56) References Cited

OTHER PUBLICATIONS

Nagarajan, Muthukaman, et al., "Synthesis and Anticancer Activity of Simplified Indenoisoquinoline Topoisomerase I Inhibitors Lacking Substituents on the Aromatic Bag", 2004, Journal of Medicinal Chemistry, vol. 47, No. 23, pp. 5651-5661.
Strumbert, Dirk, et al., "Synthesis of Cytotoxic Indenoisoquinoline Topoisomerase I Poisons", 1999, *Journal of Medicinal Chemistry*, vol. 42, No. 3, pp. 446-457.
Wawzonek, Stanley, "Novel Formation of 11-Ketoindeno[1,2-c]Isocoumarin", 1968, The Journal of Organic Chemistry, vol. 33, No. 2, pp. 896-897.
Wawzonek, Stanley, "Synthesis of 6-Substituted-6H-Indeno[1,2-c]Isoquinoline-5,11-diones", 1982, Database CA, Chemical Abstracts Service, Database Accession No. 1982:199485.
Staker, B.L.; Hjerrild, K.; Feese, M.D.; Behnke, C.A.; Burgin Jr., A.B.; Stewart, L "The Mechanism of Topoisomerase I Poisoning by a Camptothecin Analog," *Proc. Natl. Acad. Sci. U.S.A.*, 2002, 99, 15387-15392.
Pommier, Y.; Pourquier, P.; Fan, Y.; Strumberg, D. "Mechanism of Action of Eukaryotic DNA Topoisomerase I and Drugs Targeted to the Enzyme", *Biochim. Biophys. Acta*, 1998, 1400,83-106.
Kohlhagen, G.; Paull, K.; Cushman, M.; Nagafuji, P.; Pommier, Y., "Protein-Linked DNA Strand Breaks Induced by NSC 314622, a Novel Noncamptothecin Topoisomerase I Poison," *Mol. Pharmacol.*, 1998, 54, 50-58.
Jaxel, C.; Kohn, K. W.; Wani, M. C.; Wa.., M.C.; Pommier, Y., "Structure-Activity Study of the Actions of Camptothecin Derivatives on Mammalian Topoisomerase I: Evidence for a Specific Receptor Site and a Relation to Antitumor Activity," *Cancer. Rev.*, 1989, 49, 1465-1469.
Minami, H.; Beijnen, J.H.; Verweij, J.; Ratain, M. J., "Limited Sampling Model for the Area under the Concentration Time Curve of Total Topotecan", *Clin. Cancer Res.*, 1996, 2, 43-46.
Danks, M.K.; Pawlik, C.A.; Whipple, D.O.; Wolverton, J.S., "Intermittant Exposure of Medulloblastoma Cells to Topotecan Produces Growth Inhibition equivalent to Continuous Exposure," Clinical Cancer Research, 1997, 3, 1731-1738.
Haas, N.B.; LaCreta, F.P.; Walczak, J.; Hudes, G.R.; Brennan, J.M.; Ozols, R.F.; O'Dwyer, P.J. "Phase I/Pharmacokinetic Study of Topotecan by 24-Hour Continuous Infusion Weekly," *Cancer Res.*, 1994, 54, 1220-1226.
Shapiro, S.L.; Geiger, K.; Youlus, J.; Freedman, L., "Indandiones. II. A Modified Dieckmann Reaction," *J. Org. Chem.*, 1961, 26, 3580-3582.
Pailer, M.; Worther, H.; Meller, A., "Some reactions of 2-aryl-1,3-indandiones", *Monatsh Chem.*, 1961, 92, 1037-1047.
Freireich, E.J., et al., "Quantitative Comparison to Toxicity of Anticancer Agents in Mouse, Rat, Hamster, Dog, Monkey, and Man", *Cancer Chemother. Rep.*, 1966, 50 (4), 219-244.

Nagarajan, M.; Xiao, X.; Antony, S.; Kohlhagen, G.; Pommier, Y.; Cushman, M., "Design, Synthesis, and Biological Evaluation of Indenoisoquinoline Topoisomerase I Inhibitors Featuring Polyamine Side Chains on the Lactam Nitrogen," *J. Med. Chem,.* 2003, 46, 5712-5724.
Hollingshead, M.; Plowman, J.; Alley, M.; Mayo, J.; Sausville, E., "The Hollow Fiber Assay," *Contrib. Oncol,.* 1999, 54, 109-120.
Plowman, J.; Camalier, R.; Alley, M.; Sausville, E.; Schepartz, S., "US NCI Testing Procedures" *Contrib. Onco,l.* 1999, 54, 121-135.
Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.*, 2003, 63, 7428-7435.
West, Anthony R., "Solid State Chemistry and its Applications," Wiley, New York, 1988, pp. 358 & 365.
Staker et al., "Structures of Three Classes of Anticancer Agents Bound to the Human Topoisomerase I-DNA Covalent Complex," J. Med. Chem., 2005, vol. 48, No. 7, 2336-2345.
Ioanoviciu et al., "Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex as Determined by X-ray Crystallographic Analysis," J. Med. Chem., 2005, vol. 48, No. 15, 4803-4814.
Xiao et al., "On the Binding of Indeno[1,2-c]isoquinolines in the DNA-Topoisomerase I Cleavage Complex," J. Med. Chem., 2005, vol. 48, No. 9, 3231-3238.
Antony et al., "Cellular Topisomerase I Inhibition and Antiproliferative Activity by MJ-III-65 (NSC 706744), an Indenoisoquinoline Topoisomerase I Poison," Molecular Pharmacology, 2005, vol. 67, No. 2, 523-530.
Strumberg, D., Pommier, Y., Paull, K., Jayaraman, M., Nagafuji, P., & Cushman, M. (1999). Synthesis of cytotoxic indenoisoquinoline topoisomerase I poisons. Journal of medicinal chemistry, 42(3), 446-457.
Sarkhel, B. K.; Ghosh, A.; Srivastava, J. N. Reaction of homophthalic acid with m-hydroxybenzoic acid. J. Indian Chem. Soc. 1961, 553-554.
Morrell, A.; Antony, S.; Kohlhagen, G.; Pommier, Y.; Cushman, M. Synthesis of Benz-d-indeno-1,2-b-pyran-5,11-diones: Versatile Intermediates for the Design and Synthesis of Topoisomerase I Inhibitors. Bioorg. Med. Chem. Lett. 2006, 16, 1846-1849.
Nagarajan, M.; Morrell, A.; Antony, S.; Kohlhagen, G.; Agama, K.; Pommier, Y.; Ragazzon, P. A.; Garbett, N. C.; Chaires, J. B.; Hollingshead, M.; Cushman, M. Synthesis and Biological Evaluation of Bisindenoisoquinolines as Topoisomerase I Inhibitors. J. Med. Chem. 2006, 49, 5129-5140.
Waisser et al., Chemicals Abstract Service, Database Accession No. 123:132077 of Folia Pharmaceutica Universitatis Carolinae (1995), 18, 35-39.
Waisser et al., Folia Pharmaceutica Universitatis Carolinae (1995), 18, pp. 35-39.

N-SUBSTITUTED INDENOISOQUINOLINES AND SYNTHESES THEREOF

CROSS REFERENCE TO RELATED APPLICATIONS

This application is a continuation application under 35 U.S.C. §120 of U.S. application Ser. No. 13/317,153, filed Oct. 11, 2011, now U.S. Pat. No. 8,829,022, which is a continuation of U.S. application Ser. No. 12/093,398, filed May 12, 2008, now U.S. Pat. No. 8,053,443, which is a U.S. national application under 35 U.S.C. §371 (b) of International Application No. PCT/US2006/043933, filed Nov. 13, 2006, which claims the benefit under 35 U.S.C. §119 (e) of U.S. Provisional Application Ser. No. 60/736,471, filed Nov. 14, 2005, and U.S. Provisional Application Ser. No. 60/808,699, filed May 26, 2006, the disclosures of which are hereby incorporated herein by reference.

GOVERNMENT RIGHTS

This invention was made with government support under Grant Nos. CA895661 and CA009634 awarded by the National Institutes of Health. The government has certain rights in this invention.

TECHNICAL FIELD

The invention described herein pertains to N-substituted indenoisoquinoline compounds. The invention described herein also pertains to methods for treating cancer in mammals using indenoisoquinoline compounds.

BACKGROUND

The control and cure of cancer represents one of our most challenging health problems. The treatment of cancer can be approached by several modes of therapy including surgery, radiation, chemotherapy or a combination of any of these treatments. Chemotherapy continues to be an indispensable therapy for inoperable or metastatic forms of the disease. Thus, the discovery of compounds specifically targeting cancer cells, or the cellular mechanisms involved in the proliferation of cancer cells, can provide significant advancement in the eradication or control of cancer.

The selection of compounds having effective anticancer activity is complicated by the still limited knowledge of cancer cell biology and biochemistry. Therefore, development of new effective anti-cancer agents remains heavily dependent on screening of new compounds for cytotoxic activity. Antineoplastic drug candidates exhibit enhanced cytotoxicity against cancer cells relative to normal cells. Methods of screening for anticancer activity have focused on several targets, (1) the ability of a compound to inhibit tumor growth and/or progression in animal studies; (2) inhibition of cell growth/proliferation in cell lines of cancerous origin; and (3) inhibition of intracellular processes necessary for the growth or propagation of cancer cells.

The mouse L1210 leukemia cell line was initially the preferred model system used for screening compounds for anticancer activity. However, the P388 murine leukemia system was found to be more sensitive and predictive than L1210 leukemia system; it has been used as a primary screen during the past decade. Systematic screening for compounds exhibiting toxicity to these two cell lines has resulted in the isolation of a large number of active natural products. However, the anticancer activities of these compounds were predominantly for leukemia, lymphoma and a few rare tumors. Low clinical efficacy, or the lack of clinical efficacy of known chemotherapeutics against slower growing solid tumors, is a serious concern.

Considering the diversity of cancer in terms of cell type, morphology, growth rate and other cellular characteristics, the U.S. National Cancer Institute (NCI) has developed a disease-oriented approach to anticancer activity screening (M. R. Boyd, in "Principle of Practice of Oncology" J. T. Devita, S. Hellman, S. A. Rosenberg (Eds.) Vol. 3, PPO Update, No. 10, 1989). This in vitro prescreening system is based on the measurement of anticancer cytotoxicity against human cancer cell line panels consisting of approximately 60 cell lines of major human cancers (including leukemia, and slower growing tumor cells such as lung, colon, breast, skin, kidney, etc.) and is referred hereinafter as "COMPARE" screening. An important advantage of the new in vitro screening panels is the opportunity to facilitate identification of compounds that are selectively more cytotoxic to cells of certain types of cancers, thus increasing the ability to select compounds for further study with respect to specific diseases.

Anticancer agents are known to act through a variety of mechanisms to destroy or inhibit the proliferation of cancer cells. For example, some agents are antimetabolites which act as false substrates in the biochemical processes of cancer cells. One compound which has this mechanism of action is methotrexate, an analog of folic acid, which functions in part by binding to dihydrofolate reductase, thereby preventing the formation of guanine and adenine from the folic acid precursor molecule. Thus, methotrexate inhibits the ability of cancer cells to construct DNA by inhibiting the proper metabolism of folic acid.

Other anticancer agents act by alkylating DNA strands, thereby producing defects in the normal double helical structure of the DNA molecule. This alkylation may cause the formation of breaks and inappropriate links between (or within) strands of DNA. Such disruption of the DNA structure, if not repaired by intracellular repair mechanisms, impairs the cell's ability to replicate its DNA. Examples of alkylating anticancer agents are cyclophosphamide and chlorambucil.

Some anticancer agents target the intracellular mechanisms involved in replication of the DNA strand itself. Replication of a cell's genetic material requires a means to pull the DNA double helix apart into two strands. This separation is typically accomplished by the enzyme topoisomerase I. Disruption of the function of this enzyme results in DNA strand breaks in cells that are dividing, thereby causing the death of the dividing cell. Because cancer cells grow and reproduce at a much faster rate than normal cells, they are more vulnerable to topoisomerase I inhibition than are normal cells. Thus, agents that inhibit topoisomerase I are known to be potent anticancer agents. The drug camptothecin was shown to be an inhibitor of topoisomerase I and a potent anticancer agent. However, it has been observed that camptothecin may produce toxic side effects. In addition, the effectiveness of camptothecin is hampered by both the instability of the molecule itself, resulting in lactone ring opening, and the reversible nature of the inhibition, allowing impacted cells to recover. Therefore, the search for potent inhibitors of topoisomerase I continues.

SUMMARY OF THE INVENTION

Described herein are N-substituted indenoisoquinoline compounds, and more specifically, substituted 11H-indeno[1,2-c]isoquinoline compounds, including dimers of such substituted 11H-indeno[1,2-c]isoquinoline compounds formed with a divalent linker. The compounds described herein may be useful for treating cancer. Also described herein are pharmaceutical compositions of such compounds, processes for preparing N-substituted indenoisoquinoline compounds, and methods for treating cancer by administering therapeutically effective amounts of such substituted indenoisoquinoline compounds alone or as pharmaceutical compositions.

In one illustrative embodiment, novel compounds of formula I are described

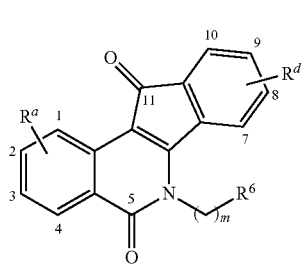

(I)

and pharmaceutically acceptable salts, hydrates, and solvates thereof, wherein:

m is an integer from 0 to about 6;

$R^6$ is selected from haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoallylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof; and $R^a$ and $R^d$ each independently represent hydrogen, or one or more optional and independently selected monovalent and divalent substituents.

In one aspect, $R^a$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another aspect, $R^d$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, m is the integer 0. In another embodiment, m is an integer from 1 to about 6, and $R^6$ is selected from halo, haloalkyl, halocycloalkyl, alkoxy, cycloalkoxy, haloalkoxy, halocycloalkoxy, optionally substituted heteroaryl, aryloxy, heteroaryloxy, and heteroarylamino, acyloxy, haloacyloxy, amino, dialkylamino, trialkylammonium, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof.

In another illustrative embodiment, $R^6$ includes a water soluble or hydrophilic functional group. In one aspect, $R^6$ includes an optionally substituted aminoalkyl. In another aspect, $R^6$ includes an alkyl group substituted with optionally substituted heteroaryl, heteroaryloxy, or heteroarylamino, amino, dialkylamino, trialkylammonium, bis(hydroxyalkyl) amino, hydroxyalkylaminoalkylamino, heteroarylalkylaminoalkylamino, acylamino, hydroxylamino, alkoxylamino, acyloxylamino, heterocyclyl, heterocyclylamino, nitro, or azido.

In another illustrative embodiment, $R^a$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, $R^a$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, $R^d$ represents 1-4 substituents each of which is independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, $R^d$ represents 2-4 substituents where 2 of said substituents are adjacent substituents and are taken together with the attached carbons to form an optionally substituted heterocycle, and where any remaining substituents are each independently selected from the group consisting of halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

In another illustrative embodiment, m is an integer from 0 to about 6, and $R^6$ is selected from the group consisting of haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof; provided that when $R^6$ is hydroxy, alkylamino, or hydroxyalkylamino, m is the integer 0.

In another illustrative embodiment, novel compounds of formula II are described

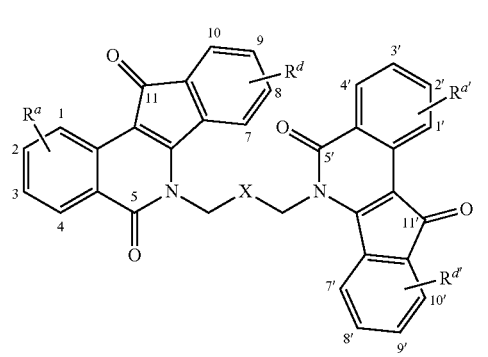

(II)

and pharmaceutically acceptable salts, hydrates, and solvates thereof, wherein:

$R^a$, $R^d$, $R^{a'}$, and $R^{d'}$ each independently represent 4 substituents, all of which are independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or where 2 of said substituents are adjacent substituents and are taken together with the attached carbons to form an optionally substituted heterocycle; and X is a divalent linker comprising one or more divalent radicals selected from $-(CR^1R^2)$, $-(NR^1)-$ and $-O-$, where $R^1$ and $R^2$ are independently selected in each occurrence from hydrogen, alkyl, and acyl, providing that the divalent linker does not include $-O-O-$. In one aspect, if present, each divalent $-(NR^1)-$ and $-O-$ is separated by at least one divalent radical $(-CR^1R^2)-$. In another aspect, each $R^1$ and $R^2$ is hydrogen.

In another illustrative embodiment, X is a group having the general structure $-(CH_2)_n-[(CH_2)_x-NR^1-(CH_2)_y]_z-(NR^2)_p-(CH_2)_q-$, where n is 0 or 1, x and y are integers independently ranging from 1 to about 4, z is an integer ranging from 1 to about 4, p is 0 or 1, q is 0 or an integer ranging from 1 to about 2, and where $R^1$ and $R^2$ are independently selected in each instance from hydrogen, methyl, t-butyloxycarbonyl, benzyloxycarbonyl, and fluorenylmethoxycabonyl, or $R^1$ and $R^2$ and any adjacent $R^2$ together with the attached nitrogens form a heterocycle.

In another illustrative embodiment, indenoisoquinoline compounds of formulae I and II described herein are useful for treating cancer or tumors. In one aspect, compounds described herein exhibit the activity of stabilizing DNA-topoisomerase I cleavage complexes through intercalation at the DNA cleavage site, resulting in inhibition of the religation reaction. See, for example, Kohlhagen, G.; Paull, K.; Cushman, M.; Nagafuji, P.; Pommier, Y. Protein-Linked DNA Strand Breaks Induced by NSC 314622, a Novel Noncamptothecin Topoisomerase I Poison *Mol. Pharmacol.* 1998, 54, 50-58; Pommier, Y.; Pourquier, P.; Fan, Y.; Strumberg, D. Mechanism of Action of Eukaryotic DNA Topoisomerases and Drugs Targeted to the Enzyme *Biochem. Biophys. Acta.* 1998, 1400, 83-105; Staker, B. L.; Hjerrild, K.; Feese, M. D.; Behnke, C. A.; Burgin Jr., A. B.; Stewart, L. The Mechanism of Topoisomerase I Poisoning by a Camptothecin *Analog Proc. Natl. Acad. Sci. U.S.A.* 2002, 99, 15387-15392, the disclosures of each of which are incorporated herein by reference. As inhibitors of the DNA religation reaction occurring after DNA cleavage by topoisomerase 1, compounds described herein may be classified as "top 1 poisons," and may exhibit biological and pharmacological activity similar to that observed with camptothecins. In another aspect, indenoisoquinoline compounds of formulae I and II described herein may be efficacious against various types of human cancers. In another aspect, indenoisoquinoline compounds of formulae I and II described herein may be chemically more stable than camptothecin. In yet another aspect, indenoisoquinoline compounds of formulae I and II described herein may have unique DNA binding site selectivities relative to camptothecin.

In another illustrative embodiment, methods for treating human cancers are described. In one aspect of the methods described herein, the cancers are attributable to abnormally fast cell growth, reproduction, and/or proliferation. In another aspect, the cancers treatable by compounds of formulae I and II are responsive to enzyme inhibition, such as inhibition of topoisomerase 1.

In another illustrative embodiment, processes for preparing indenoisoquinoline compounds of formula I and II are described. In one embodiment, the processes include preparing an intermediate benz[d]indeno[1,2-b]pyran-5,11-dione of the formula III

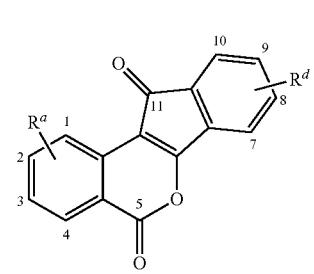

(III)

where the process comprises reacting a 2-carboxybenzaldehyde compound and a phthalide compound of respective formulae

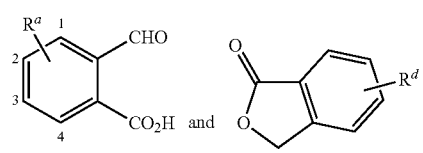

followed by acidic treatment in benzene under reflux or treatment with a suitable coupling reagent such as dicyclohexylcarbodiimide with dimethyaminopyridine, wherein $R^a$ and $R^d$ are as defined herein for compounds of formulae I and II.

In another illustrative embodiment, processes are described herein for preparing compounds of formulae I and II comprising the steps of (i) reacting an $R^a$-substituted hydroxy phthalide compound and an $R^d$-substituted phthalide compound of respective formulae

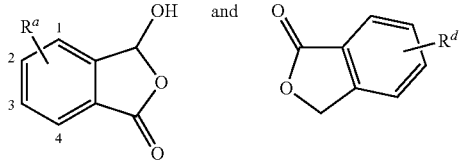

in the presence of a base, then (ii) treating the mixture with an acid to prepare the intermediate benz[d]indeno[1,2-b]pyran-5,11-dione described above, wherein $R^d$ and $R^d$ are as defined herein for compounds of formulae I and II.

In another illustrative embodiment, processes are described herein for preparing compounds of formulae I and II comprising the steps of reacting a benz[d] indeno[1,2-b]pyran-5,11-dione of the formula

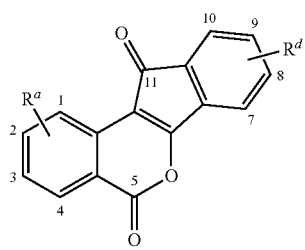

with a primary amine of the formula $R^6$—$(CH_2)_m$—$NH_2$, wherein $R^a$, $R^d$, m, and $R^6$ are as defined herein for compounds of formulae I and II. In one embodiment, the primary amine is illustratively 4-(2-aminoethyl)morpholine, 1-(3-aminopropyl)imidazole, N-(3-aminopropyl)-N,N-dimethylamine, 4-(hydroxy)butylamine, 3-(bromo)propylamine, a mono-Boc-protected diamine, and the like. It is appreciated that although chloroform at room temperature will suffice as the solvent for most primary amines, when a primary amine such as a mono-Boc-protected diamine, for example, is used to form the lactam from a benz[d]indeno[1,2-b]pyran-5,11-dione, chloroform at reflux may be used as the solvent. It is further appreciated that an indenoisoquinoline compound for which the integer m is not 0, and wherein $R^6$ is halo, azido, or cyano, for example, may be further elaborated through displacement of the halo, azido, or cyano functionality, respectively, with a variety of nucleophiles.

In another illustrative embodiment, processes are described herein for preparing compounds of formulae I and II comprising the steps of reacting an optionally substituted homophthalic anhydride and an optionally substituted Schiff base of respective formulae

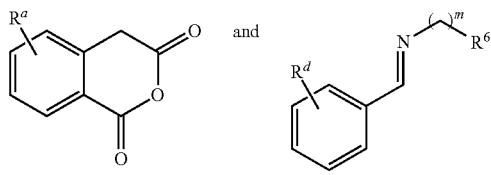

followed by subjecting the resulting carboxylic acid to oxidative Friedel-Crafts ring closure with thionyl chloride and aluminum chloride, wherein $R^a$, $R^d$, m, and $R^6$ are as defined herein for compounds of formulae I and II.

In another illustrative embodiment, processes are described herein for preparing compounds of formulae I and II comprising the steps of reacting a benz[d]indeno[1,2-b]pyran-5,11-dione of the formula

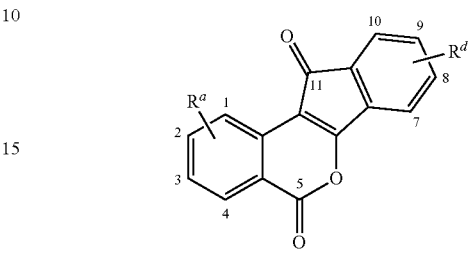

with a polyamine of the formula $NH_2$—$(CH_2)_n$—$[(CH_2)_x$—$NR^1$—$(CH_2)_y]_z$—$(NR^2)_p$—$(CH_2)_q$—$NH_2$, where $R^1$, $R^2$, n, x, y, z, p, q, $R^a$, and $R^d$ are as defined herein for compounds of formula II. In one embodiment, the polyamine is illustratively N,N-bis(2-aminoethyl)amine, N,N-bis(3-aminopropyl)amine, N-(2-aminoethyl)-N-(3-aminopropyl)-amine, N,N'-bis(2-aminoethyl)-1,3-propanediamine, N,N'-bis(3-aminopropyl)-1,3-propanediamine and the like.

It is to be understood that each of the aspects of the various illustrative embodiments described herein may be modified and/or combined as additional illustrative embodiments. For example, illustrative embodiments of the compounds of formula II may include those aspects wherein an unsubstituted, symmetrical bisindenoisoquinoline is present, as reflected in the use of a benz[d]indeno[1,2-b]pyran-5,11-dione where $R^a$ and $R^d$ are each hydrogen. Further, illustrative embodiments of the compounds of formula II may include those aspects wherein a substituted, symmetrical bisindenoisoquinoline is present, as reflected in the use of a benz[d]indeno[1,2-b] pyran-5,11-dione where, for example, $R^a$ is 2,3-dimethoxy and $R^d$ is hydrogen, or where, for example, $R^a$ is 3-nitro and $R^d$ is hydrogen. In addition, illustrative embodiments of the compounds of formula II may include those aspects wherein a substituted, unsymmetrical bisindenoisoquinoline is present, as reflected in the use of a mixture of two differentially substituted benz[d]indeno[1,2-b]pyran-5,11-diones to prepare a dimer such as

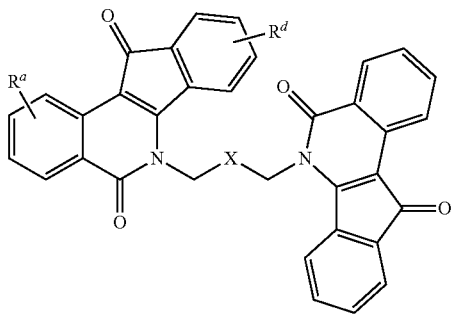

wherein Ra, Rd, and X are as defined herein for compounds of formula II, and wherein Ra≠H and/or Rd≠H.

DETAILED DESCRIPTION

In one illustrative embodiment, novel compounds of formula I are described

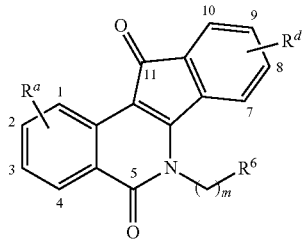

(I)

and pharmaceutically acceptable salts, hydrates, and solvates thereof, wherein:

m is an integer from 0 to about 6; and $R^6$ is selected from haloalkyl, halocycloalkyl, hydroxy, alkoxy, cycloalkoxy, haloalkoxy, halocycloalkoxy, optionally substituted heteroaryl, aryloxy, heteroaryloxy, and heteroarylamino, acyloxy, haloacyloxy, amino, alkyl and dialkylamino, trialkylammonium, hydroxyalkylamino, bis(hydroxyalkyl)amino, hydroxyalkylaminoalkylamino, heteroarylalkylaminoalkylamino, acylamino, hydroxylamino, alkoxylamino, acyloxylamino, cycloalkyl, heterocyclyl, heterocyclylamino, alkynyl, acyl, urethanyl, cyano, nitro, azido, thio, alkylsulfonyl, sulfonic acid and derivatives thereof, carboxylic acid and derivatives thereof, and phosphonic acid and derivatives thereof;

$R^a$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where the remaining substituents, in cases where $R^a$ represents 3-4 substituents, are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; and $R^d$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where the remaining substituents, in cases where represents 3-4 substituents, are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$, $C_1$-$C_4$ alkyl, methyl, ethyl, propyl, 3-methylpentyl, and the like.

As used herein, the term "cycloalkyl" refers to a monovalent chain of carbon atoms, a portion of which forms a ring. It is understood that in embodiments that include cycloalkyl, illustrative variations of those embodiments include lower cycloalkyl, such as $C_3$-$C_8$, $C_3$-$C_6$ cycloalkyl, cyclopropyl, cyclohexyl, 3-ethylcyclopentyl, and the like.

As used herein, the term "alkenyl" refers to an unsaturated monovalent chain of carbon atoms including at least one double bond, witch may be optionally branched. It is understood that in embodiments that include alkenyl, illustrative variations of those embodiments include lower alkenyl, such as $C_2$-$C_6$, $C_2$-$C_4$ alkenyl.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as $C_2$-$C_4$, alkylene, methylene, ethylene, propylene, 3-methylpentylene, and the like.

As used herein, the term "heterocycle" refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

It is to be understood that each of alkyl, cycloalkyl, alkenyl, cycloalkenyl, alkylene, and heterocyclyl may be optionally substituted with independently selected groups such as alkyl, haloalkyl, hydroxyalkyl, aminoalkyl, carboxylic acid and derivatives thereof, including esters, amides, and nitriles, hydroxy, alkoxy, acyloxy, amino, alkyl and dialkylamino, acylamino, thio, and the like, and combinations thereof.

As used herein, the term "optionally substituted aryl" refers to an aromatic mono or polycyclic ring of carbon atoms, such as phenyl, naphthyl, and the like, which may be optionally substituted with one or more independently selected substituents, such as halo, hydroxy, amino, alkyl or dialkylamino, alkoxy, alkylsulfonyl, cyano, nitro, and the like.

As used herein, the term "optionally substituted heteroaryl" refers to an aromatic mono or polycyclic ring of carbon atoms and at least one heteroatom selected from nitrogen, oxygen, and sulfur, such as pyridinyl, pyrimidinyl, indolyl, benzoxazolyl, and the like, which may be optionally substituted with one or more independently selected substituents, such as halo, hydroxy, amino, alkyl or dialkylamino, alkoxy, alkylsulfonyl, cyano, nitro, and the like.

As used herein, the term "acyl" refers to hydrogen, alkyl, cycloalkyl, alkenyl, cycloalkenyl, heterocyclyl, optionally substituted aryl, optionally substituted arylalkyl, optionally substituted heteroaryl, and optionally substituted heteroarylalkyl attached as a substituent through a carbonyl (C=O) group, such as formyl, acetyl, pivalolyl, benzoyl, phenacetyl, and the like.

As used herein, the terms "dialkylamino," "dialkylammonium," and "trialkyammonium" refer to amino substituted with alkyl groups, where each alkyl group is independently selected, and illustratively includes dimethylamino, methylethylamino, diisopropylethylammonium, benzyldimethylammonium, benzyldiisopropylammonium, and the like.

As used herein, the terms "protected hydroxy" and "protected amino" refer to hydroxy and amino groups, respectively, that are protected with a protecting group. It is to be understood that such protecting groups are conventional and routinely selected to allow a synthetic or chemical transformation to be performed in a manner that the hydroxy group or amino group does not interfere with or is not changed by the synthetic or chemical transformation performed. Illustrative, but not exclusive, examples of such protecting groups may be found in Greene & Wuts "Protective Groups in Organic Synthesis," 2d Ed., John Wiley & Sons, New York, 1991, the disclosure of which is incorporated herein by reference. Further illustrative of such protecting groups are those particularly suited for protecting phenols and catechols, and analogs and derivatives thereof.

In one illustrative aspect of the compounds of formula I, $R^6$ is dialkylamino, including dimethylamino, azido, poly(hydroxyalkyl)amino, hydroxyalkylaminoalkylamino, polyhydroxyalkylaminoalkylamino, hydroxyalkyl(alkylamino), heteroaryl, or a combination thereof. In another aspect, $R^6$ is selected from the formulae

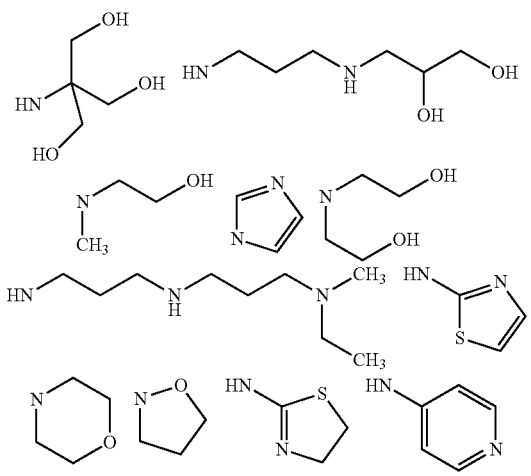

each of which may be optionally substituted. In another aspect, m is 2, 3, or 4.

In another aspect of the compounds of formula I, $R^6$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), and combinations thereof. In another aspect, $R^6$ is substituted $C_1$-$C_4$ alkyl. In another aspect, $R^6$ is substituted $C_3$ alkyl.

In another illustrative embodiment of the compounds of formula I, $R^a$ represents one or more substituents selected from optionally substituted alkoxy. In one aspect, $R^a$ represents at least two adjacent substituents taken together to form alkylenedioxy. In another embodiment, $R^a$ represents one or more substituents selected from halo, hydroxy, amino, alkyl and dialkylamino, nitroso, nitro, hydroxylamino, alkoxylamino, and cyano. In another embodiment of the compounds of formula I, $R^d$ represents one or more substituents selected from optionally substituted alkoxy. In one aspect, $R^d$ represents at least two adjacent substituents taken together to form alkylenedioxy. In another embodiment, $R^d$ represents one or more substituents selected from halo, amino, alkyl and dialkylamino, nitroso, nitro, and cyano.

In another illustrative embodiment of the compounds of formula I, $R^6$ is alkyl substituted with amino, dialkylamino, trialkylammonium, poly(hydroxyalkyl)amino, hydroxyalkylaminoalkylamino, (polyhydroxy)alkylaminoalkylamino, heteroaryl, azido, hydroxyalkyl(alkylamino), and combinations thereof. In another aspect, $R^6$ is substituted $C_1$-$C_4$ alkyl. In another aspect, $R^6$ is substituted $C_3$ alkyl. In another aspect, $R^a$ represents one or more substituents selected from optionally substituted alkoxy. In another aspect, $R^a$ represents at least two adjacent substituents taken together to form alkylenedioxy. In another aspect, $R^a$ represents one or more substituents selected from halo, hydroxy, amino, alkyl and dialkylamino, nitroso, nitro, hydroxylamino, alkoxylamino, and cyano. In another aspect, $R^d$ represents one or more substituents selected from optionally substituted alkoxy. In another aspect, $R^d$ represents at least two adjacent substituents taken together to form alkylenedioxy. In another aspect, $R^d$ represents one or more substituents selected from halo, amino, alkyl and dialkylamino, nitroso, nitro, and cyano.

In another illustrative embodiment, indenobenzopyran compounds of formula III are described, where $R^a$ and $R^d$ are as defined in the compounds of formulae I and II. These compounds may be used to prepare compounds of formulae I and II according to the processes described herein. In one embodiment, compounds 4a-4s are described, as shown in the following table. Compounds 4a-4s were prepared by the processes described herein comprising the steps of preparing and cyclizing the adduct of an optionally substituted 2-carboxybenzaldehyde and an optionally substituted phthalide as described herein.

(III)

| Compound | $R^a$ | $R^d$ |
|---|---|---|
| 4a | 2,3-(MeO)$_2$ | H |
| 4b | 2,3-(OCH$_2$O) | H |
| 4c | 3-NO$_2$ | H |
| 4d | H | H |
| 4e | 2,3-(MeO)$_2$ | 8,9-(OCH$_2$O) |
| 4f | 2,3-(MeO)$_2$ | 8,9-(MeO)$_2$ |
| 4g | 2,3-(MeO)$_2$ | 7,8,9-(MeO)$_3$ |
| 4h | 2,3-(OCH$_2$O) | 8,9-(MeO)$_2$ |
| 4i | 2,3-(OCH$_2$O) | 8,9-(OCH$_2$O) |
| 4j | 2,3-(OCH$_2$O) | 7,8,9-(MeO)$_3$ |
| 4k | 1,2,3-(MeO)$_3$ | 8,9-(MeO)$_2$ |
| 4l | 1,2,3-(MeO)$_3$ | 8,9-(OCH$_2$O) |
| 4m | 1,2,3-(MeO)$_3$ | 7,8,9-(MeO)$_3$ |
| 4n | 1,4-(MeO)$_2$ | 8,9-(MeO)$_2$ |
| 4o | 1,4-(MeO)$_2$ | 8,9-(OCH$_2$O) |
| 4p | 1,4-(MeO)$_2$ | 7,8,9-(MeO)$_3$ |
| 4q | 2,3,4-(MeO)$_3$ | 8,9-(MeO)$_2$ |
| 4r | 2,3,4-(MeO)$_3$ | 8,9-(OCH$_2$O) |
| 4s | 2,3,4-(MeO)$_3$ | 7,8,9-(MeO)$_3$ |

In another illustrative embodiment, novel indenoisoquinoline compounds 5a-5z, 5aa-5az, and 5ba-5bs are described. These compounds were prepared by the processes described herein comprising the steps of preparing the corresponding benz[d]indeno[1,2-b]pyran-5,11-dione and converting the lactone into the corresponding lactam with a suitable primary amine, or by condensing an optionally substituted homophthalic anhydride and an optionally substituted Schiff base, as described herein.

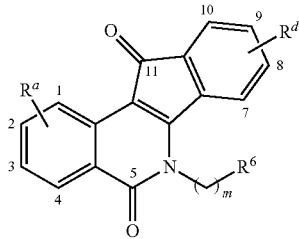

(I)

| Compound | $R^a$ | $R^d$ | m | $R^6$ |
|---|---|---|---|---|
| 5a | 2,3-(MeO)$_2$ | H | 3 | (Me)$_2$N |
| 5b | 2,3-(OCH$_2$O) | H | 3 | (Me)$_2$N |
| 5c | 3-NO$_2$ | H | 3 | (Me)$_2$N |
| 5d | H | H | 3 | (Me)$_2$N |
| 5e | 2,3-(MeO)$_2$ | H | 3 | imidazol-1-yl |
| 5f | 3-NO$_2$ | H | 3 | imidazol-1-yl |
| 5g | H | H | 3 | imidazol-1-yl |
| 5h | 2,3-(MeO)$_2$ | H | 2 | morpholin-4-yl |
| 5i | 3-NO$_2$ | H | 2 | morpholin-4-yl |
| 5j | H | H | 2 | morpholin-4-yl |
| 5k | 2,3-(MeO)$_2$ | 8,9-(OCH$_2$O) | 3 | CF$_3$CO$_2$ |
| 5l | 2,3-(MeO)$_2$ | 8,9-(OCH$_2$O) | 3 | imidazol-1-yl•2HCl |
| 5m | 2,3-(MeO)$_2$ | 8,9-(OCH$_2$O) | 3 | pyrazol-1-yl |
| 5n | 2,3-(MeO)$_2$ | 8,9-(OCH$_2$O) | 3 | triazol-1-yl•HCl |
| 5o | 2,3-(MeO)$_2$ | 8,9-(OCH$_2$O) | 3 | thiazol-2-ylamino•2HCl |
| 5p | 2,3-(MeO)$_2$ | 8,9-(OCH$_2$O) | 3 | piperazin-1-yl•2HCl |
| 5q | 2,3-(MeO)$_2$ | 8,9-(OCH$_2$O) | 3 | morpholin-4-yl |
| 5r | 2,3-(MeO)$_2$ | 8,9-(OCH$_2$O) | 3 | thiomorpholin-4-yl |
| 5s | 2,3-(MeO)$_2$ | 8,9-(OCH$_2$O) | 3 | 3-hydroxypiperidin-1-yl•HCl |
| 5t | 2,3-(MeO)$_2$ | 8,9-(OCH$_2$O) | 3 | 1-methylpiperazin-1-yl•2HCl |
| 5u | 2,3-(MeO)$_2$ | 8,9-(OCH$_2$O) | 3 | 4-aminopiperidin-1-yl•2HCl |
| 5v | 2,3-(MeO)$_2$ | 8,9-(OCH$_2$O) | 3 | homopiperazin-1-yl•2HCl |
| 5w | 2,3-(MeO)$_2$ | 8,9-(OCH$_2$O) | 3 | 4-(hydroxyethyl)piperazin-1-yl |
| 5x | 2,3-(MeO)$_2$ | 8,9-(OCH$_2$O) | 3 | morpholinylethylamino |
| 5y | 2,3-(MeO)$_2$ | 8,9-(OCH$_2$O) | 3 | bromo |
| 5z | H | H | 0 | —NH$_2$ |
| 5aa | H | H | 2 | —NHBoc |
| 5ab | H | H | 3 | —NHBoc |
| 5ac | H | H | 4 | —NHBoc |
| 5ad | H | H | 5 | —NH$_2$ |
| 5ae | H | H | 6 | —NH$_2$ |
| 5af | H | H | 7 | —NHBoc |
| 5ag | H | H | 8 | —NHBoc |
| 5ah | H | H | 9 | —NHBoc |
| 5ai | H | H | 10 | —NHBoc |
| 5aj | H | H | 11 | —NHBoc |
| 5ak | H | H | 12 | —NHBoc |
| 5al | H | H | 2 | —NH$_3^+$Cl$^-$ |
| 5am | H | H | 3 | —NH$_3^+$Cl$^-$ |
| 5an | H | H | 4 | —NH$_3^+$Cl$^-$ |
| 5ao | H | H | 5 | —NH$_3^+$Cl$^-$ |
| 5ap | H | H | 6 | —NH$_3^+$Cl$^-$ |
| 5aq | H | H | 7 | —NH$_3^+$Cl$^-$ |
| 5ar | H | H | 8 | —NH$_3^+$Cl$^-$ |
| 5as | H | H | 9 | —NH$_3^+$Cl$^-$ |
| 5at | H | H | 10 | —NH$_3^+$Cl$^-$ |
| 5au | H | H | 11 | —NH$_3^+$Cl$^-$ |
| 5av | H | H | 12 | —NH$_3^+$Cl$^-$ |
| 5aw | H | H | 1 | 2-pyridyl |
| 5ax | H | H | 1 | 3-pyridyl |
| 5ay | H | H | 2 | 2-pyridyl |
| 5az | H | H | 2 | 3-pyridyl |
| 5ba | 3-NO$_2$ | 9-MeO | 3 | chloro |
| 5bb | 3-NO$_2$ | H | 3 | bromo |
| 5bc | H | 9-MeO | 3 | chloro |
| 5bd | 3-NO$_2$ | 9-MeO | 3 | iodo |
| 5be | H | 9-MeO | 3 | iodo |
| 5bf | H | 9-MeO | 3 | azido |
| 5bg | H | 9-MeO | 3 | —NH$_3^+$Cl$^-$ |
| 5bh | H | H | 3 | azido |
| 5bi | 3-NO$_2$ | H | 3 | morpholin-4-yl |
| 5bj | 3-NO$_2$ | 9-MeO | 3 | morpholin-4-yl |
| 5bk | H | 9-MeO | 3 | morpholin-4-yl |
| 5bl | 3-NO$_2$ | H | 3 | —NH—CH$_2$—CH$_2$—OH•HCl |

-continued

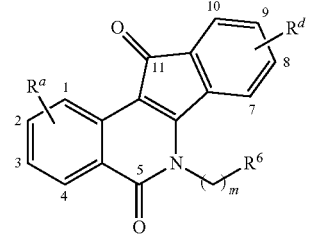

(I)

| Compound | $R^a$ | $R^d$ | m | $R^6$ |
|---|---|---|---|---|
| 5bm | 3-NO$_2$ | 9-MeO | 3 | —NH—CH$_2$—CH$_2$—OH•HCl |
| 5bn | H | 9-MeO | 3 | —NH—CH$_2$—CH$_2$—OH•HCl |
| 5bo | H | H | 3 | —NH—CH$_2$—CH$_2$—OH•HCl |
| 5bp | 3-NO$_2$ | 9-MeO | 3 | (Me)$_2$N |
| 5bq | H | 9-MeO | 3 | (Me)$_2$N |
| 5br | 3-NO$_2$ | 9-MeO | 3 | imidazol-1-yl |
| 5bs | H | 9-MeO | 3 | imidazol-1-yl |

It is appreciated that compounds 5a-5z, 5aa-5az, and 5ba-5bs may be chemically more stable than camptothecin, owing, at least in part, to the absence of a lactone ring, such as is found in camptothecin. See, (a) Jaxel, C.; Kohn, K. W.; Wani, M. C.; Pommier. Y. Structure-Activity Study of the Actions of Camptothecin Derivatives on Mammalian Topoisomerase 1: Evidence for a Specific Receptor Site and a Relation to Antitumor Activity *Cancer. Rev.* 1989, 49, 1465-1469. (b) Minanri, H.; Beijnen, J. H.; Verweij, J.; Ratain, M. J. Limited Sampling Model for the Area under the Concentration Time Curve of Total Topotecan *Clin. Cancer Res.* 1996, 2, 43.46. (c) Danks, M. K.; Pawlik, C. A.; Whipple, D. O.; Wolverton, J. S. Intermittant Exposure of Medulloblastoma Cells to Topotecan Produces Growth Inhibition equivalent to Continuous Exposure *Curr. Topics Med. Chem.* 1997, 3, 1731-1738. (d) Haas. N. B.; LaCreta, F. P.; Walczak, J.; Hudes, G. R.; Brennan, J. M.; Ozols, R. F.; O'Dwyer, P. J. PhaseI/Pharmaco-kinetic Study of Topotecan by 24-Hour Continuous Infusion Weekly *Cancer Res.* 1994, 54, 1220-1226, the disclosures of which are incorporated herein by reference. It is further appreciated that compounds 5a-5z, 5aa-5az, and 5ba-5bs may be efficacious against various types of human cancers. It is also appreciated that compounds 5a-5z, 5aa-5az, and 5ba-5bs may have unique DNA binding site selectivities relative to camptothecin.

In another illustrative embodiment, processes for preparing unsubstituted benz[d]indeno[1,2-b]pyran-5,11-dione 4d are described. In one aspect, indenobenzopyran 4d may be prepared as shown in Scheme 1, wherein condensation of 2-carboxybenzaldehyde Id and phthalide 2d in methanol/ethyl acetate with sodium methoxide (step (a)) generates an intermediate 3d, which can be isolated and subsequently cyclized in acidified, refluxing benzene (step (b)) to provide indenobenzopyran 4d. See, Shapiro, S. L.; Geiger, K.; Youlus, J.; Freedman, L. Indandiones A Modified Dieckman Reaction *J. Org. Chem.* 1961, 26, 3580-3582. In another aspect, indenobenzopyran 4d was prepared by a novel, one-pot two-step method, without isolation of intermediate 3d, which resulted in an improved yield (86%) compared to the previously reported synthesis yield (31%). See, Palior. M.; Worther, H.; Meller, A. Some reactions of 2-aryl-1,3indandiones *Monatsh Chem.* 1961, 92, 1037-1047.

Scheme 1

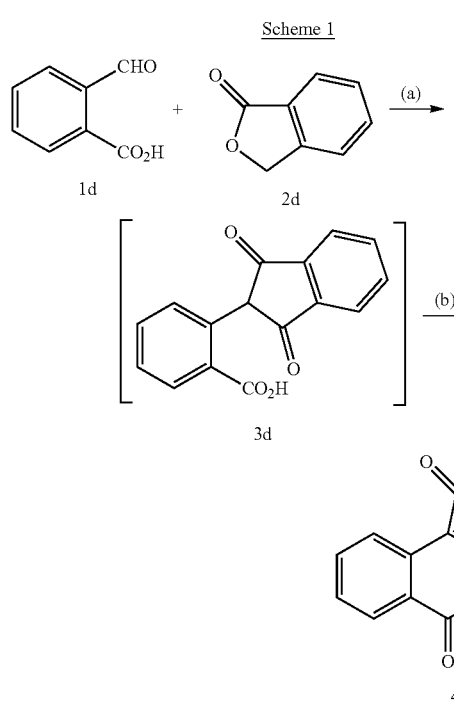

In another illustrative embodiment, substituted benz[d]indeno[1,2-b]pyran-5,11-diones 4 are prepared as shown in Scheme 2. Treatment of optionally substituted phthalide 2 with N-bromosuccinimde in carbon tetrachloride/benzene under reflux (step (a)) affords brominated phthalide 2e. Treating brominated phthalide 2e with aqueous acidic conditions under reflux (step (b)) affords hydroxylated phthalide 2f. Condensation of hydroxylated phthalide 2f with optionally substituted phthalide 2 in a solution comprising methanol at room temperature, and an organic base, such as sodium methoxide (step (c)), followed by reflux under acidic conditions (step (d)) affords optionally substituted indenobenzopyrans 4, where $R^a$ and $R^d$ are as defined herein.

Scheme 2

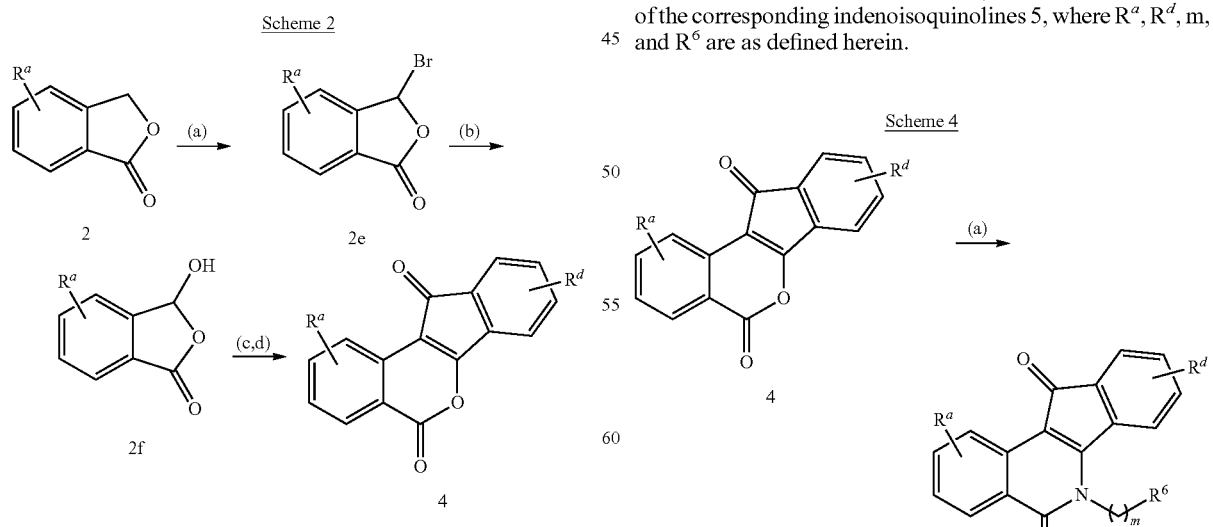

In another illustrative embodiment, a novel, one-pot two-step process for preparing substituted benz[d]indeno[1,2-b]pyran-5,11-diones 4 is described. As shown in Scheme 3, condensation of optionally substituted 2-carboxybenzaldehydes 1 and optionally substituted phthalides 2 in methanol/ethyl acetate with sodium methoxide (step (a)) generates intermediates 3, which are cyclized without isolation in acidified, refluxing benzene or via dicyclohexylcarbodiimide and dimethylaminopyridine (step (b)) to provide optionally substituted indenobenzopyrans 4, where $R^a$ and $R^d$ are as defined herein.

Scheme 3

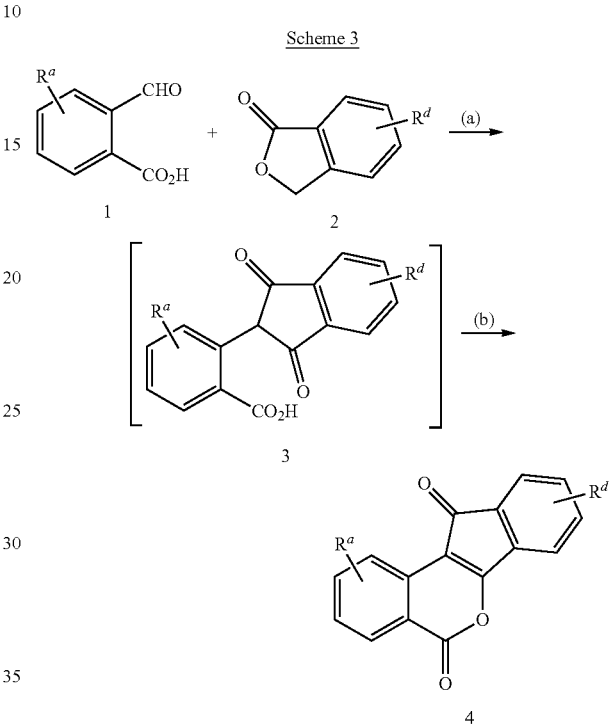

In another illustrative embodiment, indenoisoquinoline compounds of formula I are prepared as outlined in Scheme 4. Treatment of the indenobenzopyrans 4 in chloroform with a primary amine of the formula $R^6—(CH_2)_m—NH_2$ (step (a)), where $R^6$ and m are as defined herein, results in the formation of the corresponding indenoisoquinolines 5, where $R^a$, $R^d$, m, and $R^6$ are as defined herein.

Scheme 4

It is appreciated that although chloroform at room temperature will suffice as the solvent for most primary amines, when a primary amine such as a mono-Boc-protected diamine, for example, is used to form the lactam from a benz[d]indeno[1,2-b]pyran-5,11-dione 4, chloroform at reflux may be used as the solvent. It is further appreciated that an indenoisoquinoline compound 5 for which the integer m is not 0, and wherein $R^6$ is halo, azido, or cyano, for example, may be further elaborated through displacement of the halo, azido, or cyano functionality, respectively, with a variety of nucleophiles. Illustratively, treatment of indenobenzopyran 4 in chloroform with 3-(bromo)propylamine (step (a)), i.e., a primary amine where $R^6$ and m in the formula $R^6$—$(CH_2)_m$—$NH_2$ are bromo and 3, respectively, results in the formation of the corresponding N-(3-bromo-1-propyl)indenoisoquinoline 5, which compound can be treated with sodium azide or sodium cyanide in DMSO or with primary and secondary amines, such as ethanolamine, imidazole, N,N-dimethylamine, morpholine, piperazine, and the like, in refluxing dioxane, with concomitant displacement of bromide ion. An N-(3-cyano-1-propyl)indenoisoquinoline 5 may be converted to a variety of carboxylic acid derivatives, including, for example, esters, amides, acid chlorides, and the like.

In another illustrative embodiment, indenoisoquinoline compounds of formula I are prepared as outlined in Scheme 5. Condensation of optionally substituted homophthalic anhydrides 6 with optionally substituted Schiff bases 7, where $R^a$, $R^d$, m, and $R^6$ are as defined herein, generates carboxylic acids 8 (step (a)), for which the indicated cis stereochemical relationship is based on the observed coupling constant of ~6 Hz for the two methine protons. (Carboxylic acids 9, with a trans stereochemical relationship, would be expected to display a coupling constant on the order of ~10-12 Hz for the two methine protons.) Subjecting carboxylic acids 8 to oxidative Friedel-Crafts ring closure with thionyl chloride and aluminum chloride (step (b)) provides indenoisoquinolines 5, where $R^a$, $R^d$, m, and $R^6$ are as defined herein.

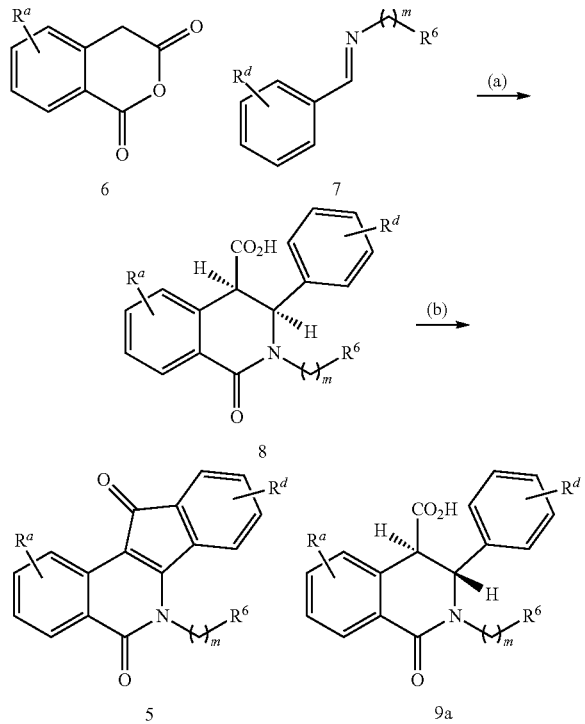

Scheme 5

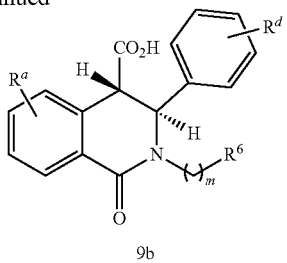

9b

In another illustrative embodiment, indenoisoquinoline compounds 10a-10o are described, where the various aspects and embodiments of m and $R^6$ are as described herein, and $R^a$ and $R^d$ are as indicated in the following table:

(I)

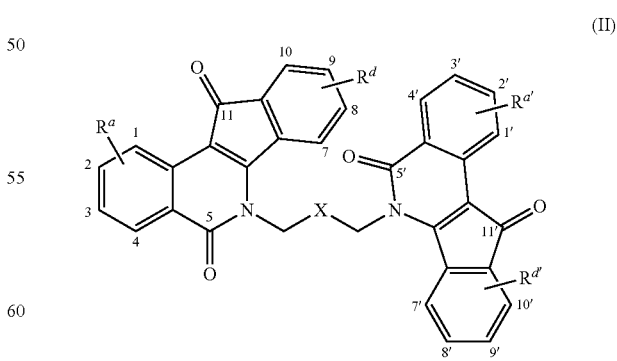

| Compound | $R^a$ | $R^d$ |
|---|---|---|
| 10a | 2,3-(MeO)$_2$ | 8,9-(MeO)$_2$ |
| 10b | 2,3-(MeO)$_2$ | 8,9-(OCH$_2$O) |
| 10c | 2,3-(MeO)$_2$ | 7,8,9-(MeO)$_3$ |
| 10d | 2,3-(OCH$_2$O) | 8,9-(MeO)$_2$ |
| 10e | 2,3-(OCH$_2$O) | 8,9-(OCH$_2$O) |
| 10f | 2,3-(OCH$_2$O) | 7,8,9-(MeO)$_3$ |
| 10g | 1,2,3-(MeO)$_3$ | 8,9-(MeO)$_2$ |
| 10h | 1,2,3-(MeO)$_3$ | 8,9-(OCH$_2$O) |
| 10i | 1,2,3-(MeO)$_3$ | 7,8,9-(MeO)$_3$ |
| 10j | 1,4-(MeO)$_2$ | 8,9-(MeO)$_2$ |
| 10k | 1,4-(MeO)$_2$ | 8,9-(OCH$_2$O) |
| 10l | 1,4-(MeO)$_2$ | 7,8,9-(MeO)$_3$ |
| 10m | 2,3,4-(MeO)$_3$ | 8,9-(MeO)$_2$ |
| 10n | 2,3,4-(MeO)$_3$ | 8,9-(OCH$_2$O) |
| 10o | 2,3,4-(MeO)$_3$ | 7,8,9-(MeO)$_3$ |

In another illustrative embodiment, novel compounds of formula II are described (II)

and pharmaceutically acceptable salts, hydrates, and solvates thereof, wherein:

$R^a$, $R^d$, $R^{a'}$, and $R^{d'}$ each independently represent 4 substituents, all of which are independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or where 2 of said substituents are adjacent substituents and are taken together with the attached carbons to form an optionally substituted heterocycle; and X is a divalent linker comprising one or more divalent radicals selected from —(CR$^1$R$^2$), —(NR$^1$)— and —O—, where R$^1$ and R$^2$ are independently selected in each occurrence from hydrogen, alkyl, and acyl, providing that the divalent linker does not include —O—O—. In one aspect, if present, each divalent —(NR$^1$)— and —O— is separated by at least one divalent radical (—CR$^1$R$^2$)—. In another aspect, each R$^1$ and R$^2$ is hydrogen.

In another illustrative embodiment, X is a group having the general structure —(CH$_2$)$_n$—[(CH$_2$)$_x$—NR$^1$—(CH$_2$)$_y$]$_z$—(NR$^2$)$_p$—(CH$_2$)$_q$—, where n is 0 or 1, x and y are integers independently ranging from 1 to about 4, z is an integer ranging from 1 to about 4, p is 0 or 1, q is 0 or an integer ranging from 1 to about 2, and where R$^1$ and R$^2$ are independently selected in each instance from hydrogen, methyl, t-butyloxycarbonyl, benzyloxycarbonyl, and fluorenylmethoxycabonyl, or R$^1$ and R$^2$ and, any adjacent R$^2$ together with the attached nitrogens form a heterocycle.

In one illustrative embodiment of the compounds of formula II, R$^a$ and R$^{a'}$ independently represent one or more substituents selected from optionally substituted alkoxy. In one aspect, R$^a$ and R$^{a'}$ independently represent at least two adjacent substituents taken together to form alkylenedioxy. In another embodiment, R$^a$ and R$^{a'}$ independently represent one or more substituents selected from halo, hydroxy, amino, alkyl and dialkylamino, nitroso, nitro, hydroxylamino, alkoxylamino, and cyano. In another embodiment of the compounds of formula II, R$^d$ and R$^{d'}$ independently represent one or more substituents selected from optionally substituted alkoxy. In one aspect, R$^d$ and R$^{d'}$ independently represent at least two adjacent substituents taken together to form alkylenedioxy. In another embodiment, R$^d$ and R$^{d'}$ independently represent one or more substituents selected from halo, amino, alkyl and dialkylamino, nitroso, nitro, and cyano.

In another illustrative embodiment of the compounds of formula II, n, p, and q are 0, and z is 2, 3, or 4. In another aspect, n and p are 1, z is 1, and q is 2. In one aspect, R$^a$ and R$^{a'}$ independently represent one or more substituents selected from optionally substituted alkoxy. In another aspect, R$^a$ and R$^{a'}$ independently represent at least two adjacent substituents taken together to form alkylenedioxy. In another aspect, R$^a$ and R$^{a'}$ independently represent one or more substituents selected from halo, hydroxy, amino, alkyl and dialkylamino, nitroso, nitro, hydroxylamino, alkoxylamino, and cyano. In another aspect, R$^d$ and R$^{d'}$ independently represent one or more substituents selected from optionally substituted alkoxy. In another aspect, R$^d$ and R$^{d'}$ independently represent at least two adjacent substituents taken together to form alkylenedioxy. In another aspect, R$^d$ and R$^{d'}$ independently represent one or more substituents selected from halo, amino, alkyl and dialkylamino, nitroso, and cyano.

In another illustrative embodiment, bisindenoisoquinoline compounds 12-17 are described. These compounds were prepared by the processes described herein comprising the steps of preparing and aminolyzing, with a suitable polyamine, a benz[d]indeno[1,2-b]pyran-5,11-dione 4 as described herein.

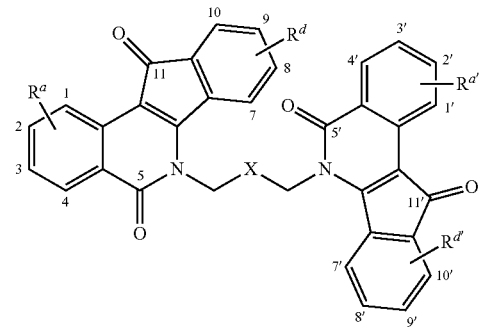

(II)

| Cpd | R$^a$ | R$^{a'}$ | R$^d$ | R$^{d'}$ | —X— |
|---|---|---|---|---|---|
| 12a | H | H | H | H | CH$_2$NHCH$_2$ |
| 12b | H | H | H | H | CH$_2$CH$_2$NHCH$_2$ |
| 12c | H | H | H | H | CH$_2$CH$_2$NHCH$_2$CH$_2$ |
| 12d | H | H | H | H | CH$_2$CH$_2$N(CH$_3$)CH$_2$CH$_2$ |
| 12e | H | H | H | H | CH$_2$CH$_2$NHCH$_2$CH$_2$CH$_2$ |
| 12f | H | H | H | H | CH$_2$NH(CH$_2$)$_2$NHCH$_2$ |
| 12g | H | H | H | H | CH$_2$NH(CH$_2$)$_3$NHCH$_2$ |
| 12h | H | H | H | H | CH$_2$CH$_2$NH(CH$_2$)$_2$NHCH$_2$CH$_2$ |
| 12i | H | H | H | H | CH$_2$CH$_2$N(CH$_2$CH$_2$)$_2$NCH$_2$CH$_2$ |
| 12j | H | H | H | H | CH$_2$CH$_2$NH(CH$_2$)$_3$NHCH$_2$CH$_2$ |
| 12k | H | H | H | H | CH$_2$CH$_2$NH(CH$_2$)$_4$NHCH$_2$CH$_2$ |
| 12l | H | H | H | H | CH$_2$NH(CH$_2$)$_2$NH(CH$_2$)$_2$NHCH$_2$ |
| 12m | H | H | H | H | CH$_2$NH(CH$_2$)$_2$NH(CH$_2$)$_2$NHCH$_2$NHCH$_2$ |
| 13a | H | H | H | H | CH$_2$NBoc(CH$_2$)$_3$NBocCH$_2$ |
| 13b | H | H | H | H | CH$_2$CH$_2$NBoc(CH$_2$)$_2$NBocCH$_2$CH$_2$ |
| 13c | H | H | H | H | CH$_2$CH$_2$NBoc(CH$_2$)$_3$NBocCH$_2$CH$_2$ |
| 13d | H | H | H | H | CH$_2$CH$_2$NBoc(CH$_2$)$_4$NBocCH$_2$CH$_2$ |
| 13e | H | H | H | H | CH$_2$NBoc(CH$_2$)$_2$NBoc(CH$_2$)$_2$NBocCH$_2$ |
| 13f | H | H | H | H | CH$_2$NBoc(CH$_2$)$_2$NBoc(CH$_2$)$_2$NBoc(CH$_2$)$_2$NBocCH$_2$ |
| 14a | H | H | H | H | CH$_2$CH$_2$NHCH$_2$•TFA |

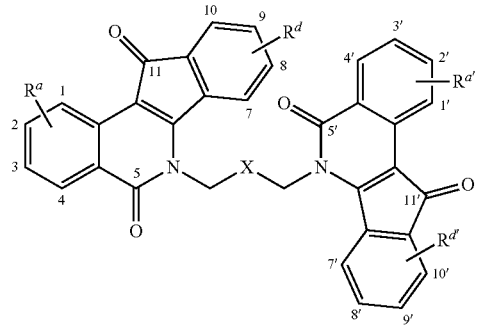

(II)

| Cpd | $R^a$ | $R^{a'}$ | $R^d$ | $R^{d'}$ | —X— |
|---|---|---|---|---|---|
| 14b | H | H | H | H | CH$_2$CH$_2$NHCH$_2$CH$_2$CH$_2$•HCl |
| 14c | H | H | H | H | CH$_2$NH(CH$_2$)$_2$NHCH$_2$•2 TFA |
| 14d | H | H | H | H | CH$_2$NH(CH$_2$)$_3$NHCH$_2$•2 TFA |
| 14e | H | H | H | H | CH$_2$CH$_2$NH(CH$_2$)$_2$NHCH$_2$CH$_2$•2 TFA |
| 14f | H | H | H | H | CH$_2$CH$_2$N(CH$_2$CH$_2$)$_2$NCH$_2$CH$_2$•2 TFA |
| 14g | H | H | H | H | CH$_2$CH$_2$NH(CH$_2$)$_3$NHCH$_2$CH$_2$•2 TFA |
| 14h | H | H | H | H | CH$_2$CH$_2$NH(CH$_2$)$_4$NHCH$_2$CH$_2$•2 TFA |
| 14i | H | H | H | H | CH$_2$NH(CH$_2$)$_2$NH(CH$_2$)$_2$NHCH$_2$•3 TFA |
| 14j | H | H | H | H | CH$_2$NH(CH$_2$)$_2$NH(CH$_2$)$_2$NHCH$_2$NHCH$_2$•4 TFA |
| 14k | 2,3-(MeO)$_2$ | 2,3-(MeO)$_2$ | H | H | CH$_2$NH(CH$_2$)$_3$NHCH$_2$•2 TFA |
| 14l | 2,3-(MeO)$_2$ | 2,3-(MeO)$_2$ | H | H | CH$_2$CH$_2$NH(CH$_2$)$_3$NHCH$_2$CH$_2$•2 TFA |
| 14m | 3-NO$_2$ | 3-NO$_2$ | H | H | CH$_2$NH(CH$_2$)$_3$NHCH$_2$•2 TFA |
| 14n | 3-NO$_2$ | 3-NO$_2$ | H | H | CH$_2$CH$_2$NH(CH$_2$)$_3$NHCH$_2$CH$_2$•2 TFA |
| 15a | 2,3-(MeO)$_2$ | H | 8,9-OCH$_2$O | H | CH$_2$CH$_2$NH(CH$_2$)$_3$NHCH$_2$CH$_2$ |
| 16a | 2,3-(MeO)$_2$ | H | 8,9-OCH$_2$O | H | CH$_2$CH$_2$NBoc(CH$_2$)$_3$NBocCH$_2$CH$_2$ |
| 17a | 2,3-(MeO)$_2$ | H | 8,9-OCH$_2$O | H | CH$_2$CH$_2$NH(CH$_2$)$_3$NHCH$_2$CH$_2$•2 TFA |

It is appreciated that compounds 12-17 may be chemically more stable than camptothecin, owing, at least in part, to the absence of the lactone ring. See, (a) Jaxel, C.; Kohn, K. W.; Wani, M. C.; Pornmier. Y. Structure-Activity Study of the Actions of Camptothecin Derivatives on Mammalian Topoisomerase 1: Evidence for a Specific Receptor Site and a Relation to Antitumor Activity *Cancer. Rev.* 1989, 49, 1465-1469. (b) Minanri, H.; Beijnen, J. H.; Verweij, J.; Ratain, M. J. Limited Sampling Model for the Area under the Concentration Time Curve of Total Topotecan *Clin. Cancer Res.* 1996, 2, 43.46. (c) Danks, M. K.; Pawlik, C. A.; Whipple, D. O.; Wolverton, J. S. Intermittant Exposure of Medulloblastoma Cells to Topotecan Produces Growth Inhibition equivalent to Continuous Exposure *Curr. Topics Med. Chem.* 1997, 3, 1731-1738. (d) Haas. N. B.; LaCreta, F. P.; Walczak, J.; Nudes, G. R.; Brennan, J. M.; Ozols, R. F.; O'Dwyer, P. J. Phase1/Pharmaco-kinetic Study of Topotecan by 24-Hour Continuous Infusion Weekly *Cancer Res.* 1994, 54, 1220-1226, the disclosures of which are incorporated herein by reference. It is further appreciated that compounds 1247 may be efficacious against various types of human cancers. It is also appreciated that compounds 12-17 may have unique DNA binding site selectivities relative to camptothecin.

In another illustrative embodiment, symmetrical bisindenoisoquinoline compounds of formula II are prepared as outlined in Scheme 6. Treatment of the indenobenzopyrans 4 in refluxing chloroform with a polyamine of the formula NH$_2$—(CH$_2$)$_n$—[(CH$_2$)$_x$—NR$^1$—(CH$_2$)$_y$]$_z$—(NR$^2$)$_p$—(CH$_2$)$_q$—NH$_2$ 11 (step (a)), where R$^1$, R$^2$, n, x, y, z, p, and q are as defined herein, results in the formation of the corresponding bisindenoisoquinolines 12, where R$^a$, R$^d$, R$^{a'}$, R$^{d'}$, and X are as defined herein. If necessary or desired, bisindenoisoquinolines 12 are converted to their respective t-butyloxycarbonyl (Boc-) derivatives 13 upon treatment with Boc anhydride and triethylamine (step (b)), then purified and treated with trifluoroacetic acid or hydrochloric acid (step (c)) to produce the corresponding TFA or HCl salt 14.

Scheme 6

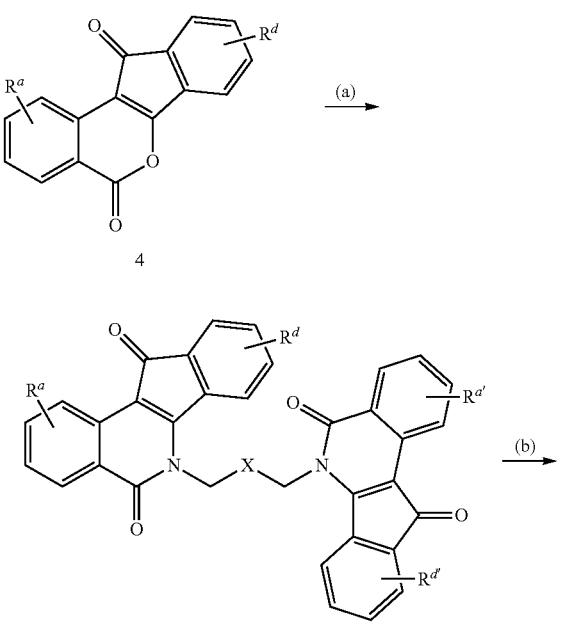

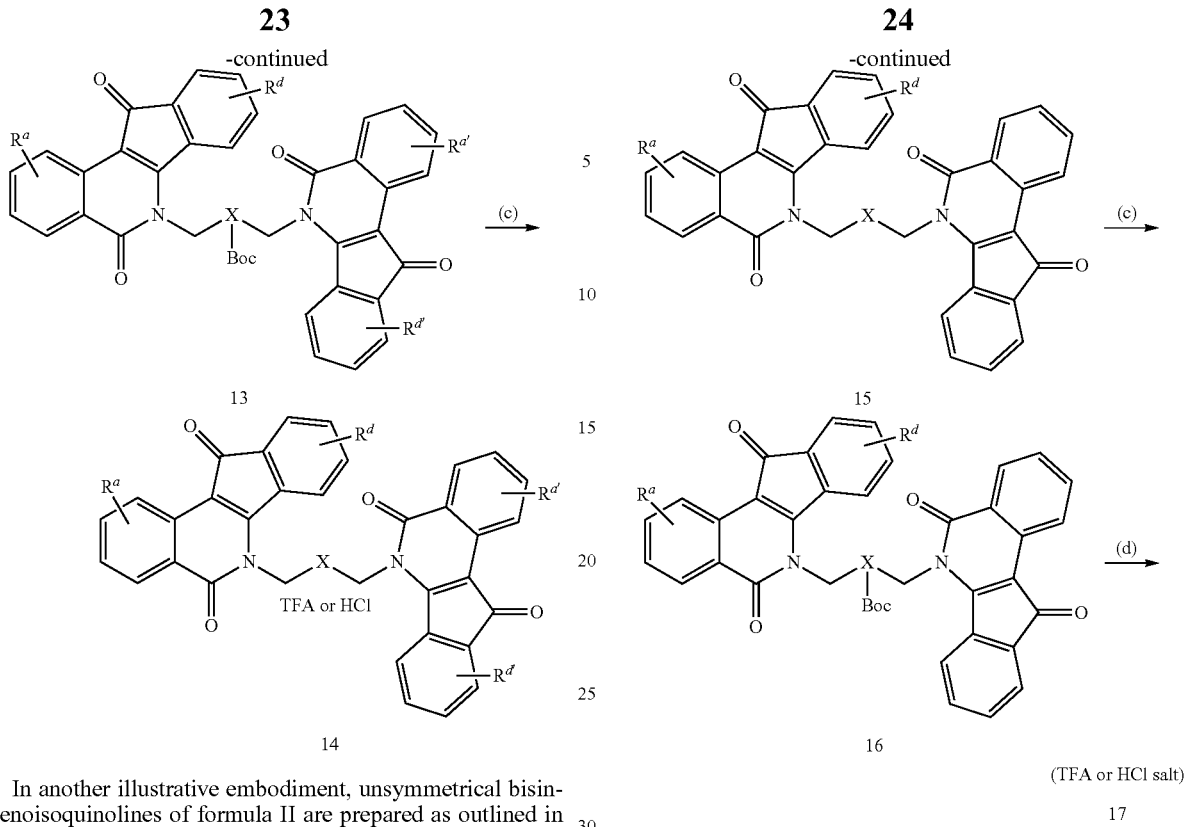

In another illustrative embodiment, unsymmetrical bisindenoisoquinolines of formula II are prepared as outlined in Scheme 7. Treatment of the indenobenzopyrans 4 with a polyamine of the formula $NH_2$—$(CH_2)_n$—$[(CH_2)_x$—$NR^1$—$(CH_2)_y]_z$—$(NR^2)_p$—$(CH_2)_q$—$NH_2$ 11 (step (a)), where $R^1$, $R^2$, n, x, y, z, p, and q are as defined herein, results in the formation of the corresponding polyaminoindenoisoquinoline A, where $R^a$, $R^d$, and X are as defined herein. Subsequent condensation of polyaminoindenoisoquinoline A with indenobenzopyran 4d (step (b)) results in the formation of the corresponding unsymmetrical bisindenoisoquinolines 15. If necessary or desired, unsymmetrical bisindenoisoquinolines 15 are converted to their respective t-butyloxycarbonyl (Boc-) derivatives 16 upon treatment with Boc anhydride and triethylamine (step (c)), then purified and treated with trifluoroacetic acid or hydrochloric acid (step (d)) to produce the corresponding TFA or HCl salt 17.

Scheme 7

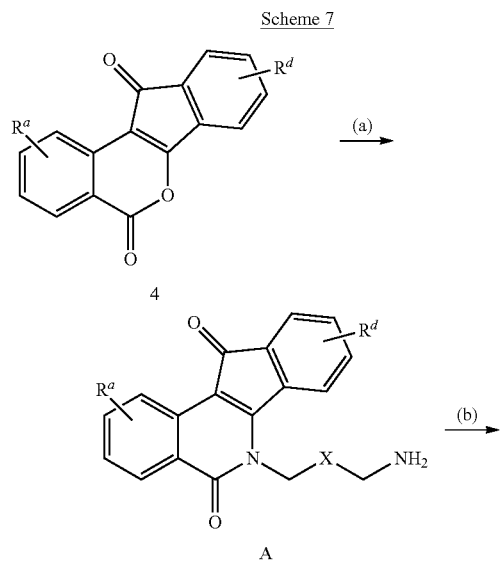

It is appreciated that bisindenoisoquinolines 12 and 15 may be converted to other acyl derivatives, including urethane derivatives such as, for example, benzyloxycarbonyl or fluorenylmethoxycarbonyl derivatives, then purified and deprotected via hydrogenolysis or treatment with piperidine, respectively.

The indenoisoquinoline and bisindenoisoquinoline compounds described herein may also form hydrates and solvates. Hydrates may be formed spontaneously upon exposure to ambient conditions where the humidity is sufficient to hydrate the compounds. In addition, hydrates may be formed with more specificity by exposing the compounds described herein to particular humidity conditions. Hydrates may also be formed with by dissolving or suspending the compounds in media containing a predetermined amount of water and evaporating, lyophilizing, or otherwise concentrating such solutions in a manner to give a hydrate form of the compounds described herein. Solvates of the indenoisoquinolinium and bisindenoisoquinolinium compounds described herein may also be formed by dissolving or suspending the compounds in a solvent that is capable of forming a complex with the compound, and subsequently evaporating or otherwise concentrating such solutions in a manner to give a solvate form of the compounds described herein. Solvents capable of forming solvates may include alcohols, such as ethanol, butanol, and the like. It is appreciated that both hydrates and solvates of the compounds described herein may have a predetermined stoichiometry. Such stoichiometry may be evaluated by conventional analytical techniques, including X-ray diffraction, melting analysis, and the like.

The compounds described herein show antineoplastic activity using the COMPARE screening methodology, demonstrating that they are antineoplastic agents useful in treating human cancers. The compounds described herein are inhibitors of topoisomerase I (top 1), and in particular may be inhibitors of the top 1-catalyzed DNA religation reaction. Such inhibition may account for the antiproliferative activity against cancer cells that compounds described herein show in vitro. The compounds described herein may form ternary complexes consisting of the compound, DNA, and the top 1 enzyme. Without being bound by theory, it is believed that the compounds described herein may be operating as top 1 poisons, which inhibit the top 1 enzyme catalyzed DNA cleavage reaction. It is further appreciated that the compounds described herein may have longer in vitro and in vivo activity than conventional treatments if the formation of the ternary complexes are not reversible or rapidly reversible.

Therefore, some of the growth inhibition demonstrated through COMPARE testing may occur through that mechanism of action, inhibition of topoisomerase I. However, it is appreciated that compounds showing surprisingly potent cell growth inhibition, even though their inhibitory effects on topoisomerase I are relatively small in comparison to other agents tested, may cause inhibition of cell growth, at least in part, through another mechanism of action in addition to or instead of inhibition of topoisomerase I.

Also described herein are pharmaceutical compositions and formulations comprising a therapeutically effective amount of one or more indenoisoquinoline or bisindenoisoquinoline compounds for treating a patient having cancer. It is appreciated that mixtures of certain indenoisoquinoline or bisindenoisoquinoline compounds may be administered. Such pharmaceutical compositions may also include one or more diluents, carriers, and/or excipients. As used herein, an effective amount of the indenoisoquinoline or bisindenoisoquinoline compound is defined as the amount of the compound which, upon administration to a patient, inhibits growth of cancer cells, kills malignant cells, reduces the volume or size of the tumors, and/or eliminates the tumor entirely in the treated patient. It is to be understood that treated patients include humans and other mammals.

As used herein, the term "therapeutically effective amount" refers to the amount to be administered to a patient, and may be based on body surface area, patient weight, and/or patient condition. In addition, it is appreciated that there is an interrelationship of dosages determined for humans and those dosages determined for animals, including test animals (illustratively based on milligrams per meter squared of body surface) as described by Freireich, E. J., et al., *Cancer Chemother. Rep.* 1966, 50 (4), 219, the disclosure of which is incorporated herein by reference. Body surface area may be approximately determined from patient height and weight (see, e.g., Scientific Tables, Geigy Pharmaceuticals, Ardley, New York, pages 537-538 (1970)). A therapeutically effective amount of the indenoisoquinoline and bisindenoisoquinoline compounds described herein may be defined as any amount useful for inhibiting the growth of (or killing) a population of malignant cells or cancer cells, such as may be found in a patient in need of relief from such cancer or malignancy. Typically, such effective amounts range from about 5 mg/kg to about 500 mg/kg, from about 5 mg/kg to about 250 mg/kg, and/or from about 5 mg/kg to about 150 mg/kg of indenoisoquinoline compounds per patient body weight. It is appreciated that effective doses may also vary depending on the route of administration, optional excipient usage, and the possibility of co-usage of the indenoisoquinoline compounds with other conventional and non-conventional therapeutic treatments, including other anti-tumor agents, radiation therapy, and the like.

The indenoisoquinoline and bisindenoisoquinoline compounds may be administered in a variety of pharmaceutical formulations, including conventional pharmaceutical formulations. The indenoisoquinoline compounds, and formulated variants thereof, may also be delivered by a variety of administration routes, including conventional delivery routes. In one embodiment, the indenoisoquinoline compounds, and formulated variants thereof, are delivered via a parenteral route, including subcutaneously, intraperitoneally, intramuscularly, and intravenously. Examples of parenteral dosage forms and formulations include aqueous solutions of the indenoisoquinoline compounds in isotonic saline, 5% glucose or other conventional pharmaceutically acceptable liquid carrier. In one aspect, the one or more indenoisoquinoline compounds are dissolved in a saline solution containing 5% dimethyl sulfoxide and 10% Cremphor EL (Sigma Chemical Company). Additional solubilizing agents such as cyclodextrins, which can form specific, more soluble complexes with the indenoisoquinoline compounds described herein, or other conventional solubilizing agents can be included as pharmaceutical excipients for delivery of the compounds.

In another embodiment, the indenoisoquinoline compounds, bisindenoisoquinoline compounds, and formulated variants thereof, are delivered via oral administration, such as in a capsule, a gel seal, a tablet, and the like. Capsules may comprise any conventional pharmaceutically acceptable material including gelatin and/or cellulose derivatives. Tablets may be formulated by conventional procedures, including by compressing mixtures of the indenoisoquinoline compounds, solid carriers, lubricants, disintegrants, and other conventional ingredients for solid dosage forms, such as starches, sugars, bentonite, and the like. The compounds described herein may also be administered in a form of a hard shell tablet or capsule containing, for example, lactose or mannitol as a binder, and conventional fillers and tableting agents. Solid dosage forms described herein and useful for delivering the indenoisoquinoline compounds also include sustained release formulations, such as tablets, caplets, pills, capsules, and the like that include an enteric coating that may delay the release of the indenoisoquinoline compounds until the formulation has passed into the intestinal tract.

The following exemplary embodiments are included herein to further illustrate the invention. These exemplary embodiments are not intended and should not be interpreted to limit the scope of the invention in any way. It is to be understood that numerous variations of these exemplary embodiments are contemplated herein.

COMPOUND EXAMPLES

Melting points were determined in capillary tubes and are uncorrected. Infrared spectra were obtained using $CHCl_3$ as the solvent unless otherwise specified. Except where noted, 300 MHz $^1$H NMR spectra were obtained using $CDCl_3$ as solvent and the solvent peak as internal standard. Mass spectra were determined by electrospray mass spectrometry. Microanalyses were performed at the Purdue University Microanalysis Laboratory. Reactions were generally monitored by analytical thin-layer chromatography using Bakerflex silica gel IB2-F plates or flexible sheets, visualized with short wavelength UV light. Silica gel flash chromatography was performed using 230-400 mesh silica gel.

A representative procedure for the one-pot synthesis of an indenobenzopyran 4 is described herein for benz[d]indeno[1,2-b]pyran-5,11-dione 4d. It is understood that other indenobenzopyrans, including compounds 4a-4s, may be prepared according to this representative example. In addition, a representative procedure for the synthesis of an indenoisoquinoline 5 from indenobenzopyran 4 and a primary amine is described herein for 5,6-dihydro-6-(2-morpholinyl-4-ylethyl)-3-nitro-5,11-dioxo-11H-indeno[1,2-c]isoquinoline 5i. It is understood that other indenoisoquinolines, including compounds 5a-5k, may be prepared from this representative example. A representative procedure for the synthesis of an indenoisoquinoline 5 by aminolysis of 6-(3-bromo-1-propyl)-5,6-dihydro-2,3-dimethoxy-8,9-methylenedioxy-5,11-dioxo-11H-indeno[1,2-c]isoquinoline 5y is also described herein, by which procedure indenoisoquinolines 5l, and 5o-5x were prepared. In addition, a representative procedure for the synthesis of an indenoisoquinoline 5 from indenobenzopyran 4d and a mono-Boc-protected primary amine is described herein, by which procedure mono-Boc-protected indenoisoquinolines 5aa-5ac, and 5af-5ak were prepared for generation of the corresponding HCl salts 5al-5an and 5aq-5ay. Syntheses of indenoisoquinolines 5aw-5az from indenobenzopyran 4d and a series of aminopyridine derivatives are also described herein. In addition, a representative procedure is described herein for the synthesis of an indenoisoquinoline 5 by i) condensing substituted homophthalic anhydrides 6 with Schiff bases 7 and ii) subjecting the resulting carboxylic acids 8 to oxidative Friedel-Crafts ring closure, by which procedure indenoisoquinolines 5bb-5bc were prepared. It is understood that other indenoisoquinolines, including compounds 5ba, 5bd, and 5be, may be prepared according to this representative example. Indenoisoquinolines 5bf-5bs were prepared from N-haloalkylindenoisoquinolines 5bb, 5bd and 5be by the aminolysis procedure described herein. Also described herein are syntheses of bisindenoisoquinolines 12-17 from indenobenzopyrans 4 and a variety of polyamines 11.

Benz[d]indeno[1,2-b]pyran-5,11-dione (4d). Sodium methoxide (40 mL of a 4 M methanolic solution) was added to a solution of 2-carboxybenzaldehyde 1d (1.000 g, 7.455 mmol) and phthalide 2d (1.119 g, 7.455 mmol) in ethyl acetate (20 mL). The solution was heated at 65° C. for 18 h, concentrated, and acidified with concd HCl. The resulting mixture was diluted with benzene (125 mL), TsOH (100 mg) was added, and the solution was heated for 7 h at reflux in a flask affixed with a Dean-Stark trap. The solution was cooled to room temperature, concentrated, diluted with CHCl$_3$ (150 mL), and washed with sat NaHCO$_3$ (3×50 mL) and sat NaCl (50 mL). The organic layer was dried over sodium sulfate and concentrated to provide indenobenzopyran 4d as an orange solid (1.583 g, 86%): mp 258-259° C. (published mp 257° C.). $^1$H NMR (CDCl$_3$) δ 8.40 (d, J=8.56 Hz, 1 H), 8.32 (d, J=7.93 Hz, 1 H), 7.84-7.79 (m, 1 H), 7.61-7.39 (m, 5 H). Additional details regarding the synthesis of compound 8 are found in Pailer et al., *Monatsh Chem.*, 92:1037-47 (1961), the synthetic disclosure of which is incorporated herein by reference.

5,6-Dihydro-6-(2-morpholin-4-yl-1-ethyl)-3-nitro-5,11-dioxo-11H-indeno[1,2-c]isoquinoline (5i). 4-(2-Aminoethyl)morpholine (0.133 g, 1.023 mmol) was added to a solution of 3-nitrobenz[d]indeno[1,2-b]pyran-5,11-dione 4c (0.100 g, 0.341 mmol) in CHCl$_3$ (30 mL). The solution was allowed to stir at room temperature for 16 h, diluted with CHCl$_3$ (110 mL) and washed with H$_2$O (3×30 mL) and sat NaCl (30 mL). The organic layer was dried over sodium sulfate, filtered, and concentrated to provide indenoisoquinoline 9i as a crude solid. The solid was purified by flash column chromatography (SiO$_2$/CHCl$_3$ to 7% MeOH/CHCl$_3$) to provide indenoisoquinoline 5i as an orange solid (0.138 g, 100%): mp 257-259° C. IR (film) 1670, 1613, 1505, 1330, and 1078 cm$^{-1}$; $^1$H NMR (CDCl$_3$) δ 9.20 (s, 1 H), 8.89 (d, J=Hz, 1 H), 8.52 (d, J=Hz, 1 H), 7.80-7.72 (m, 2 H), 7.54 (m, 2 H), 4.73 (m, 2 H), 3.72 (bs, 4 H), 2.83 (m, 2 H), 2.62 (bs, 4 H); ESIMS m/z (rel intensity) 406 (MH$^+$, 100). Anal. Calcd for C$_{22}$H$_{19}$N$_3$O$_3$: C, 65.18; H, 4.72; N, 10.37. Found: C, 65.27; H, 4.74; N, 10.20.

General Procedure for the Synthesis of Indenoisoquinolines 5l and 5o-5x from 6-(3-bromo-1-propyl)-5,6-dihydro-2,3-dimethoxy-8,9-methylenedioxy-5,11-dioxo-11H-indeno[1,2-c]isoquinoline (5y). A mixture of 6-(3-bromo-1-propyl)-5,6-dihydro-2,3-dimethoxy-8,9-methylenedioxy-5,11-dioxo-11H-indeno[1,2-c]isoquinoline (5y) (0.500 g, 1.06 mmol), amine (2.11 mmol), and anhydrous K$_2$CO$_3$ (0.584 g, 4.23 mmol) in anhydrous 1,4-dioxane (30 mL) was heated at 100° C. for 4 h. The reaction mixture was cooled and then concentrated. The residue was diluted with water (50 mL), extracted with CHCl$_3$ (2×50 mL), washed with 1% aq HCl (50 mL), water (50 mL), sat NaCl (50 mL), and dried over Na$_2$SO$_4$. The crude product was purified by flash column chromatography (SiO$_2$), eluting with a 0-5% gradient of methanol in chloroform, to provide the pure indenoisoquinoline.

3-(Imidazolyl-1-propyl)-5,6-dihydro-2,3-dimethoxy-8,9-methylenedioxy-5,11-dioxo-11H-indeno[1,2-c]isoquinoline Hydrochloride (5l). The desired analogue was obtained as a dark purple solid (245 mg, 63%): mp 316-318° C. $^1$H NMR (CDCl$_3$) δ 8.01 (s, 1 H), 7.63 (s, 1 H), 7.60 (s, 1 H), 7.14 (s, 1 H), 7.04 (s, 2 H), 6.40 (s, 1 H), 6.07 (s, 2 H), 4.45 (t, J=5.8 Hz, 2 H), 4.20 (t, J=6.6 Hz, 2 H), 4.03 (s, 3 H), 3.98 (s, 3 H), 2.33 (t, J=6.9 Hz, 2 H); ESIMS m/z (rel intensity) 460 (MH$^+$, 100). Anal. (C$_{25}$H$_{21}$N$_3$O$_6$.0.2H$_2$O) C, H, N. The hydrochloride salt was formed by dissolving the product in chloroform (50 mL) and an anhydrous solution of 2 M HCl in diethyl ether (15 mL, 30.0 mmol) was added at 0° C. The reaction mixture was stirred at room temperature for 6 h and the precipitated product was filtered and washed with chloroform (50 mL), methanol (20 mL), and dried over P$_2$O$_5$ for 24 h to afford the product as a dark purple solid (170 mg, 79%): mp 270-272° C. $^1$H NMR (DMSO-d$_6$-CD$_3$OD, 2:1) δ 9.07 (s, 1 H), 7.78 (s, 2 H), 7.60 (s, 1 H), 7.42 (s, 1 H), 7.14 (s, 1 H), 6.96 (s, 1 H), 6.13 (s, 2 H), 4.41 (t, J=6.6 Hz, 2 H), 4.36 (t, J=7.3 Hz, 2 H), 3.86 (s, 3 H), 3.82 (s, 3 H), 2.35 (t, J=6.1 Hz, 2 H); ESIMS m/z (rel intensity) 494 (MH$^+$, 100). Anal. (C$_{25}$H$_{22}$N$_3$O$_6$Cl) C, H, N.

6-[3-Pyrazolyl-1-propyl]-5,6-dihydro-2,3-dimethoxy-8,9-methylenedioxy-5,11-dioxo-11H-indeno[1,2-c]isoquinoline (5m). 6-(3-Bromo-1-propyl)-5,6-dihydro-2,3-dimethoxy-8,9-methylenedioxy-5,11-dioxo-11H-indeno[1,2-c]isoquinoline (5y) (0.2113 g, 0.448 mmol) was added to sodium hydride (86.8 mg of a 60% suspension in mineral oil, 2.17 mmol) and pyrazole (0.1749 g, 2.57 mmol) in DMF (50 mL) and the reaction mixture was heated at 60° C. for 4 h. The reaction mixture was diluted with water (200 mL) and extracted with chloroform (200 mL). The organic layer was washed with water (7×200 mL) and concentrated. Benzene was added (2×30 mL) and the mixture was concentrated again. The residue was dissolved in chloroform (4 mL) and diethyl ether (50 mL) was added. The precipitate was washed with diethyl ether (100 mL) and a dark red solid (118.5 mg, 57.6%) was obtained: mp 262-264° C. (dec). IR. (film) 3462, 3104, 2918, 1693, 1640, 1557, 1495, 1488, 1430, 1394, 1308, 1284, 1251, 1205, 868, 785, 769 cm$^{-1}$; $^1$H NMR (DMSO-d$_6$) δ 7.97 (s, 1 H), 7.65 (d, J=1.5 Hz, 1 H), 7.61 (s, 1 H), 6.57 (s, 1 H), 6.97 (s, 1 H), 6.68 (s, 1 H), 6.33 (s, 1 H), 6.05 (s, 2 H), 4.40 (m, 4 H), 4.01 (s, 3 H), 3.96 (s, 3 H), 2.45 (m, 2 H); ESIMS m/z (rel intensity) 460 (MH$^+$, 100). Anal. (C$_{25}$H$_{21}$N$_3$O$_6$.0.75 H$_2$O) C, H, N.

6-(3-[2-(1,2,4)]-Triazolyl-1-propyl)-5,6-dihydro-2,3-dimethoxy-8,9-methylenedioxy-5,11-dioxo-11H-indeno[1,2-c]isoquinoline Hydrochloride (5n). 6-(3-Bromo-1-propyl)-5,6-dihydro-2,3-dimethoxy-8,9-methylenedioxy-5,11- dioxo-11H-indeno[1,2-c]isoquinoline (5y) (0.2538 g, 0.538 mmol) was added to sodium hydride (124.8 mg of a 60% suspension in mineral oil, 3.12 mmol) and 1,2,4-triazole (0.2673 g, 0.566 mol) in DMF (50 mL) and the reaction mixture was heated at 60° C. for 3 h. The reaction mixture was diluted with water (200 mL) and the precipitate was separated by filtration and washed with water (50 mL). The precipitate was partially dissolved in methanol-chloroform 1:1 (200 mL). Diethyl ether (100 mL) was added and the precipitate was separated by filtration and washed with additional diethyl ether (100 mL) to provide the product as the free base. The residue was dissolved in trifluoroacetic acid (2 mL) and hydrochloric acid (4 mL of a 2 M solution in diethyl ether) was added, followed by more diethyl ether (30 mL). The product was collected as a dark red solid (159.5 mg, 57%): mp>240° C. IR (KBr) 3429, 1694, 1647, 1553, 1500, 1487, 1431, 1394, 1311, 1254, 1207, 1032, 928, 873, 800, 786, 722, 617 cm$^{-1}$; $^1$H NMR (DMSO-d$_6$) δ 8.56 (s, 1 H), 7.99 (s, 1 H), 7.90 (s, 1 H), 7.52 (s, 1 H), 7.15 (s, 1 H), 7.10 (s, 1 H), 6.19 (s, 2 H), 4.44-4.38 (m, 4 H), 3.90 (s, 3 H), 3.86 (s, 3 H), 2.25 (m, 2 H); ESIMS m/z (rel intensity) 461 (MH$^+$, 53), 392 (MH$^+$—C$_2$N$_3$H$_3$, 100). High resolution ESIMS m/z (rel intensity) 461.1464 (100, MH$^+$) (calculated mass 461.1461).

6-(3-Thiazolylamino-1-propyl)-5,6-dihydro-2,3-dimethoxy-8,9-methylenedioxy-5,11-dioxo-11H-indeno[1,2-c]isoquinoline Dihydrochloride (5o). The product (213 mg, 41%) was dissolved in chloroform (50 mL) and treated with an anhydrous solution of 2 M HCl in diethyl ether (15 mL, 30.0 mmol) at 0° C. The reaction mixture was stirred at room temperature for 6 h and the precipitated product was filtered and washed with chloroform (50 mL), methanol (10 mL), and dried over P$_2$O$_5$ to provide the desired analogue as a pale purple solid (140 mg, 61%): mp 298-300° C. (deo). $^1$H NMR (DMSO-d$_6$) δ 7.82 (s, 1 H), 7.44 (s, 1 H), 7.38 (s, 1 H), 7.04 (s, 1 H), 6.18 (s, 2 H), 4.42 (bs, 2 H), 4.07 (bs, 2 H), 3.88 (s, 3 H), 3.83 (s, 3 H), 3.76 (bs, 4 H), 2.07 (bs, 2 H); ESIMS m/z (rel intensity) 494 (MH$^+$, 100). Anal. (C$_{25}$H$_{25}$N$_3$O$_6$SCl$_2$.0.6 CHCl$_3$) C, H, N.

6-(3-piperazinyl-1-propyl)-5,6-dihydro-2,3-dimethoxy-8,9-methylenedioxy-5,11-dioxo-11H-indeno[1,2-c]isoquinoline Dihydrochloride (5p). The product (350 mg, 72%) was dissolved in chloroform and treated with 2 M HCl in diethyl ether (9.0 mL, 18.2 mmol) at room temperature to afford the desired analogue as a pale purple solid (280 mg, 84%): mp 276-278 (dec). $^1$H NMR (D$_2$O) δ 6.63 (bs, 1 H), 6.53 (s, 1 H), 6.47 (bs, 1 H), 6.18 (s, 1 H), 5.91 (s, 2 H), 3.90 (bs, 2 H), 3.51 (s, 3 H), 3.46 (bs, 11 H), 3.20 (bs, 2 H), 2.02 (bs, 2 H); ESIMS m/z (rel intensity) 478 (MH$^+$, 100). Anal. (C$_{26}$H$_{29}$Cl$_2$N$_3$O$_6$.2.3H$_2$O) C, H, N.

6-[3-(Morpholin-4-yl)-1-propyl]-5,6-dihydro-2,3-dimethoxy-8,9-methylenedioxy-5,11-dioxo-11H-indeno[1,2-c]isoquinoline (5q). The product was isolated as a dark purple solid (0.220 g, 72%): mp 290-292° C. $^1$H NMR (CDCl$_3$) δ 7.98 (s, 1 H), 7.59 (s, 1 H), 7.36 (s, 1 H), 7.02 (s, 1 H), 6.07 (s, 2 H), 4.48 (t, J=7.39 Hz, 2 H), 4.02 (s, 3 H), 3.95 (s, 3 H), 3.76 (bs, 4 H), 2.54 (bs, 6 H), 2.01 (bs, 2 H); ESIMS m/z (rel intensity) 479 (MH$^+$, 100). Anal. (C$_{26}$H$_{26}$N$_2$O$_7$.0.2H$_2$O) C, H, N.

6-[3-(Thiomorpholin-4-yl)-1-propyl]-5,6-dihydro-2,3-dimethoxy-8,9-methylenedioxy-5,11-dioxo-11H-indeno[1,2-c]isoquinoline (5r). The product was isolated as a dark purple solid (275 mg, 53%): rap 306-308° C. $^1$H NMR (CDCl$_3$) δ 7.80 (s, 1 H), 7.60 (s, 1 H), 7.33 (s, 1 H), 7.04 (s, 1 H), 6.08 (s, 2 H), 4.48 (t, J=6.4 Hz, 2 H), 4.02 (s, 3 H), 3.96 (s, 3 H), 2.84-2.78 (bs, 8 H), 2.67 (bs, 2 H), 2.09 (bs, 2 H); ESIMS m/z (rel intensity) 495 (MH$^+$, 100). Anal. (C$_{26}$H$_{26}$N$_2$O$_6$S.0.3 H$_2$O) C, H, N.

6-[3-(3-Hydroxypiperidinyl)-1-propyl]-5,6-dihydro-2,3-dimethoxy-8,9-methylenedioxy-5,11-dioxo-11H-indeno[1,2-c]isoquinoline Hydrochloride (5s). The product (220 mg, 0.45 mmol, 70%) was treated with 2 M HCl in diethyl ether (4.0 mL, 6.69 mmol) in chloroform at room temperature to afford the desired analogue as a purple solid (210 mg, 89%): mp 288-290° C. $^1$H NMR (D$_2$O) δ 6.54 (bs, 1 H), 6.41 (s, 1 H), 6.29 (bs, 1 H), 6.06 (s, 1 H), 5.88 (s, 2 H), 3.82 (bs, 2 H), 3.45 (s, 3 H), 3.37 (bs, 7 H), 3.15 (bs, 3 H), 1.99 (bs, 4 H), 1.68 (bs, 2 H); ESIMS m/z (rel intensity) 493 (MH$^+$, 100). Anal. (C$_{27}$H$_{29}$ClN$_2$O$_7$.1.4H$_2$O) C, H, N.

3-[(1-Methylpiperazinyl)-1-propyl]-5,6-dihydro-2,3-dimethoxy-8,9-methylenedioxy-5,11-dioxo-11H-indeno[1,2-c]isoquinoline (5t). The desired analogue was isolated as a dark purple solid (160 mg, 51%): mp 254-256° C. $^1$H NMR (CDCl$_3$) δ 7.99 (s, 1 H), 7.60 (s, 1 H), 7.30 (s, 1 H), 7.03 (s, 1 H), 6.08 (s, 2 H), 4.47 (t, J=6.0 Hz, 2 H), 4.02 (s, 3 H), 3.96 (s, 3 H), 2.55 (bs, 10 H), 2.30 (s, 3 H), 1.99 (bs, 2 H); ESIMS m/z (rel intensity) 492 (MH$^+$, 100). Anal. (C$_{27}$H$_{29}$N$_3$O$_6$.0.5 CHCl$_3$) C, H, N.

6-[3-(4-Aminopiperidinyl)-1-propyl]-5,6-dihydro-2,3-dimethoxy-8,9-methylenedioxy-5,11-dioxo-11H-indeno[1,2-c]isoquinoline Dihydrochloride (5u). The product (205 mg, 66%) was dissolved in chloroform (30 mL) and treated with 2 M HCl in diethyl ether (5.2 mL, 10.40 mmol) at room temperature for 8 h. The precipitate was filtered and washed with chloroform (30 mL) to provide the desired analogue as a dark purple solid (165 mg, 85%): mp 262-264° C. (dec). $^1$H NMR (D$_2$O) δ 6.62 (s, 1 H), 6.50 (s, 1 H), 6.44 (s, 1 H), 6.17 (s, 1 H), 5.92 (s, 2 H), 3.92 (bs, 2 H), 3.64 (bs, 2 H), 3.50 (s, 4 H), 3.45 (s, 3 H), 3.23 (bs, 2 H), 3.08 (bs, 2 H), 2.25 (m, 2 H), 2.06 (bs, 2 H), 1.90 (m, 2 H); ESIMS m/z (rel intensity) 492 (MH$^+$, 70).

6-(3-Homopiperazinyl-1-propyl)-5,6-dihydro-2,3-dimethoxy-8,9-methylenedioxy-5,11-dioxo-11H-indeno[1,2-c]isoquinoline Dihydrochloride (5v). The obtained product (390 mg, 0.66 mmol, 69%) was dissolved in chloroform and treated with 2 M HCl in diethyl ether (10.0 mL, 19.8 mmol) to afford the desired analogue as a purple solid (305 mg, 82%): mp 264-266° C. (dec). $^1$H NMR (D$_2$O) δ 6.71 (bs, 1 H), 6.56 (bs, 2 H), 6.21 (bs, 1 H), 5.92 (s, 2 H), 3.98 (bs, 2 H), 3.63-3.57 (bs, 6 H), 3.55 (s, 3 H), 3.50 (s, 3 H), 3.36-3.25 (bs, 4 H), 2.19 (bs, 2 H), 2.09 (bs, 2 H); ESIMS m/z (rel intensity) 492 (MH$^{4+}$, 100). Anal. (C$_{27}$H$_{31}$Cl$_2$N$_3$O$_6$.0.7H$_2$O) C, H, N.

3-[(1-Hydroxyethyl-piperazine)-1-propyl]-5,6-dihydro-2,3-dimethoxy-8,9-methylenedioxy-5,11-dioxo-11H-indeno[1,2-c]isoquinoline (5w). The desired analogue was isolated as a dark brown solid (258 mg, 47%): mp 262-264° C. $^1$H NMR (CDCl$_3$) δ 8.00 (s, 1 H), 7.60 (s, 1 H), 7.32 (s, 1 H), 7.04 (s, 1 H), 6.06 (s, 2 H), 4.52 (bs, 2 H), 4.03 (s, 3 H), 3.96 (s, 3 H), 3.22 (bs, 4 H), 3.13 (bs, 6 H), 2.84 (bs, 2 H), 2.68 (bs, 2 H), 1.73 (bs, 4 H), 1.63 (bs, 4 H), 1.43 (s, 18 H), 1.41 (s, 9 H); ESIMS m/z (rel intensity) 522 (MH$^+$, 100). Anal. (C$_{28}$H$_{31}$N$_3$O$_7$.0.8H$_2$O) C, H, N.

6-[(3-Morpholylethylamino)-1-propyl]-5,6-dihydro-2,3-dimethoxy-8,9-methylenedioxy-5,11-dioxo-11H-indeno[1,2-c]isoquinoline (5x). The desired analogue was isolated as a pale purple solid (245 mg, 59%): mp 215-217° C. $^1$H NMR (CDCl$_3$) δ 8.01 (s, 1 H), 7.62 (s, 1 H), 7.42 (s, 1 H), 7.05 (s, 1 H), 6.06 (s, 2 H), 4.52 (bs, 2 H), 4.03 (s, 3 H), 3.97 (s, 3 H), 3.70 (be, 4 H), 2.81 (bs, 2 H), 2.73 (bs, 2 H), 2.53 (bs, 2 H), 2.46 (bs, 4 H), 2.02 (bs, 2 H); ESIMS m/z (rel intensity) 522 (MH$^+$, 100). Anal. (C$_{28}$H$_{31}$N$_3$O$_7$.1.0 H$_2$O) C, H, N.

General Procedure for the Preparation of Mono-Boc-Protected Diamines. Boc$_2$O (0.500 g, 2.291 mmol) was dissolved in CHCl$_3$ (10 mL) and the solution was added dropwise to a solution of diamine (11.45 mmol) in CHCl$_3$ (50 mL). The reaction mixture was allowed to stir at room temperature for 24 h, concentrated, and purified by flash column chromatography (SiO$_r$), eluting with a solution of 1% Et$_3$N/10% MeOH in CHCl$_3$, to provide the mono-Boc protected diamine. (Mono-Boc-1,2-diaminoethane, mono-Boc-1,3-diaminopropane, and mono-Boc-1,4-diaminobutane were also prepared as described below.)

Mono-Boc-1,7-diaminoheptane The general procedure provided the desired compound as a colorless semisolid (0.473 g, 90%). $^1$H NMR (CDCl$_3$) δ 4.52 (bs, 1 H), 3.12 (q, J=6.2 Hz, 2 H), 2.70 (t, J=6.8 Hz, 2 H), 1.43-1.23 (m, 19 H).

Mono-Boc-1,8-diaminooctane The general procedure provided the desired compound as a colorless semisolid (0.492 g, 88%). $^1$H NMR (CDCl$_3$) δ 4.51 (bs, 1 H), 3.12 (q, J=6.5 Hz, 2 H), 2.69 (t, J=6.8 Hz, 2 H), 1.43-1.23 (m, 21 H).

Mono-Boc-1,9-diaminononane. The general procedure provided the desired compound as a colorless semisolid (0.125 g, 21%). $^1$H NMR (CDCl$_3$) δ 4.50 (bs, 1 H), 3.12 (q, J=6.5 Hz, 2 H), 2.70 (t, J=6.8 Hz, 2 H), 1.44-1.22 (m, 23 H).

Mono-Boc-1,10-diaminodecane. The general procedure provided the desired compound as a colorless semisolid (0.192 g, 31%). $^1$H NMR (CDCl$_3$) δ $^1$H NMR (CDCl$_3$) δ 4.50 (bs, 1 H), 3.13 (q, J=6.3 Hz, 2 H), 2.71 (t, J=6.9 Hz, 2 H), 1.44-1.18 (m, 27 H).

Mono-Boc-1,11-diaminoundecane. The general procedure provided the desired compound as a colorless solid (0.555 g, 85%): mp 30-34° C. IR (film) 3370, 2919, 2851, 1687, and 1522 cm$^{-1}$; $^1$H NMR (CDCl$_3$) δ 4.49 (bs, 1 H), 3.11 (q, J=6.5 Hz, 2 H), 2.71 (t, J=6.8 Hz, 2 H), 1.44-1.27 (m, 29 H); ESIMS m/z (rel intensity) 287 (MH$^+$, 100). Anal. (C$_{16}$H$_{34}$N$_2$O$_2$) C, H, N.

Mono-Boc-1,12-diaminododecane. The general procedure provided the desired compound as a colorless semisolid (0.191 g, 28%). $^1$H NMR (CDCl$_3$) δ 4.48 (bs, 1 H), 3.11 (q, J=6.2 Hz, 2 H), 2.76 (t, J=6.9 Hz, 2 H), 1.44-1.26 (m, 31 H).

6-Amino-5,6-dihydro-5,11-diketo-11H-indeno[1,2-c]isoquinoline (5z). Benz[d]indeno[1,2-b]pyran-5,11-dione (4d) (0.150 g, 0.604 mmol) was treated with hydrazine (0.255 g, 7.964 mmol) in CHCl$_3$ (50 mL) and the reaction mixture was heated at reflux for 16 h. The reaction mixture was allowed to cool to room temperature, diluted with CHCl$_3$ (150 mL), and washed with sat NaHCO$_3$ (2×50 mL). The solution was dried over sodium sulfate and concentrated to provide a red-orange solid (0.120 g, 76%): mp 272-274° C. IR (film) 3448, 3305, 1686, 1663, 1610, 1507, 1312, 762 cm$^{-1}$; $^1$H NMR (CDCl$_3$) δ 8.54 (d, J=7.8 Hz, 1 H), 8.51 (d, J=7.2 Hz, 1 H), 8.24 (d, J=7.4 Hz, 1 H), 7.85 (m, 1 H), 7.60-7.45 (m, 4 H), 6.19 (s, 2 H); EIMS m/z (rel intensity) 262 (M$^+$, 100). Anal. (C$_{16}$H$_{10}$N$_2$O$_2$·0.25H$_2$O) C, H, N.

General Procedure for the Preparation of Mono-Boc-Protected Indenoisoquinolines. Mono-Boc protected diamine (2.054 mmol) was added to a solution of benz[d]indeno[1,2-b]pyran-5,11-dione (4d) (0.255 g, 1.027 mmol) in CHCl$_3$ (100 mL). The reaction mixture was heated at reflux for 24 h, concentrated, and purified by flash column chromatography (SiO$_2$), eluting with CHCl$_3$, to provide the mono-Boc-protected indenoisoquinoline. (Mono-hoc-protected indenoisoquinolines 5aa, 5ab, and 5ac were also prepared as described below.)

6-(7'-tert-BOC-Aminoheptyl)-5,6-dihydro-5,11-dioxo-11H-indeno[1,2-c]isoquinoline (5af). The general procedure provided the desired compound as a yellow-orange solid (0.451 g, 95%): mp 112-116° C. IR (film) 3369, 1697, 1664, 1503, and 1172 cm$^{-1}$; $^1$H NMR (DMSO-d$_6$) δ 8.58 (d, J=8.1 Hz, 1 H), 8.23 (d, J=8.2 Hz, 1 H), 7.84-7.79 (m, 1 H), 7.71 (d, J=7.7 Hz, 1 H), 7.63-7.50 (m, 4 H), 6.76 (m, 1 H), 4.50 (t, J=7.4 Hz, 2 H), 2.90 (q, J=6.2 Hz, 2 H), 1.77 (m, 2 H), 1.46-1.28 (m, 17 H); ESIMS m/z/z (rel intensity) 483 (MNa$^+$, 100). Anal. (C$_{28}$H$_{32}$N$_2$O$_4$) C, H, N.

6-(8'-tert-BOC-Aminooetyl)-5,6-dihydro-5,11-dioxo-11H-indeno[1,2-c]isoquinoline (5ag). The general procedure provided the desired compound as a yellow-orange solid (0.466 g, 97%): mp 140-143° C. IR (film) 3368, 2929, 1698, 1665, 1504, and 1172 cm$^{-1}$; $^1$H NMR (DMSO-d$_6$) δ 8.58 (d, J=7.9 Hz, 1 H), 8.23 (d, J=8.1 Hz, 1 H), 7.84-7.78 (m, 1 H), 7.71 (d, J=7.5 Hz, 1 H), 7.63-7.47 (m, 4 H), 6.75 (m, 1 H), 4.50 (t, J=7.4 Hz, 2 H), 2.91 (q, J=6.6 Hz, 2 H), 1.78 (m, 2 H), 1.46-1.26 (m, 19 H); ESIMS m/z (rel intensity) 497 (MNa$^+$, 100). Anal. (C$_{29}$H$_{34}$N$_2$O$_4$) C, H, N.

6-(9'-tert-BOC-Aminononyl)-5,6-dihydro-5,11-dioxo-11H-indeno[1,2-c]isoquinoline (5ah). The general procedure provided the desired compound as an orange solid (0.145 g, 77%): mp 91-95° C. IR (film) 3371, 2928, 1698, 1666, 1504, and 1172 cm$^{-1}$; $^1$H NMR (DMSO-d$_6$) δ 8.58 (d, J=8.0 Hz, 1 H), 8.23 (d, J=7.4 Hz, 1 H), 7.84-7.79 (m, 1 H), 7.71 (d, J=7.4 Hz, 1 H), 7.63-7.50 (m, 4 H), 6.74 (m, 1 H), 4.50 (t, J=7.3 Hz, 2 H), 2.91 (q, J=6.6 Hz, 2 H), 1.78 (m, 2 H), 1.47-1.24 (m, 21 H); ESIMS m/z (rel intensity) 511 (MNa$^+$, 100). Anal. (C$_{30}$H$_{36}$N$_2$O$_4$) C, H, N.

6-(10'-tert-BOC-Aminodecyl)-5,6-dihydro-5,1-dioxo-11H-indeno[1,2-c]isoquinoline (5ai). The general procedure provided the desired compound as a yellow-orange solid (0.220 g, 78%): mp 135-137° C. IR (film) 3368, 2927, 1698, 1666, 1504, and 1172 cm$^{-1}$; $^1$H NMR (DMSO-d$_6$) δ 8.58 (d, J=7.9 Hz, 1 H), 8.23 (dd, J=8.1 Hz and 0.7 Hz, 1 H), 7.84 (dt, J=7.2 Hz and 1.4 Hz, 1 H), 7.71 (d, J=7.5 Hz, 1 H), 7.63-7.47 (m, 4 H), 6.76 (m, 1 H), 4.50 (t, J=7.4 Hz, 2 H), 2.90 (q, J=6.5 Hz, 2 H), 1.77 (m, 2 H), 1.46-1.23 (m, 23 H); ESIMS m/z (rel intensity) 525 (MNa$^+$, 100). Anal. (C$_{31}$H$_{38}$N$_2$O$_4$) C, H, N.

6-(11'-tert-BOC-Aminoundecyl)-5,6-dihydro-5,11-dioxo-11H-indeno[1,2-c]isoquinoline (5aj). The general procedure provided the desired compound as a yellow-orange solid (0.445 g, 86%): mp 111-114° C. IR (KBr) 3364, 2918, 2850, 1678, 1660, 1534, 1505, and 758 cm$^{-1}$; $^1$H NMR (DMSO-d$_6$) δ 8.58 (d, J=8.1 Hz, 1 H), 8.23 (d, J=7.4 Hz, 1 H), 7.84-7.79 (m, 1 H), 7.71 (d, J=7.5 Hz, 1H), 7.62-7.50 (m, 4 H), 6.74 (m, 1 H), 4.50 (t, J=7.4 Hz, 2 H), 2.90 (q, J=6.5 Hz, 2 H), 1.78 (m, 2 H), 1.46-1.22 (m, 25 H); ESIMS m/z (rel intensity) 539 (MNa$^+$, 100). Anal. (C$_{32}$H$_{40}$N$_2$O$_4$) C, H, N.

6-(12'-tert-BOC-Aminododecyl)-5,6-dihydro-5,11-dioxo-11H-indeno[1,2-c]isoquinoline (5ak). The general procedure provided the desired compound as a yellow-orange solid (0.177 g, 66%): mp 129-134° C. IR (film) 3369, 2926, 1698, 1666, 1504, and 1172 cm$^{-1}$; $^1$H NMR (DMSO-d$_6$) δ 8.58 (d, J=8.0 Hz, 1 H), 8.22 (d, J=7.4 Hz, 1 H), 7.84-7.78 (m, 1 H), 7.71 (d, J=7.5 Hz, 1 H), 7.62-7.50 (m, 4 H), 6.74 (m, 1 H), 4.50 (t, J=7.3 Hz, 2 H), 2.90 (q, J=6.6 Hz, 2 H), 1.77 (m, 2 H), 1.46-1.22 (m, 27 H); ESIMS (rel intensity) 553 (MNa$^+$, 100). Anal. (C$_{33}$H$_{42}$N$_2$O$_4$) C, H, N.

6-(5-Aminopentyl)-5,6-dihydro-5,11-diketo-11H-indeno[1,2-c]isoquinoline Hydrochloride (5ao). Benz[d]indeno[1,2-b]pyran-5,11-dione (4d) (0.100 g, 0.403 mmol) was treated with 1,5-diaminopentane (0.206 g, 2.014 mmol) in CHCl$_3$ (40 mL) and the reaction mixture was heated at reflux for 16 h. The reaction mixture was allowed to cool to room temperature and washed with water (3×15 mL). The solution was dried over sodium sulfate, filtered, and treated with 2 M HCl in Et$_2$O (5 mL). After 30 min, the reaction mixture was filtered and the filter pad was washed with CHCl$_3$ (50 mL) and hexanes (50 mL) to provide an orange solid (0.122 g, 82%): mp 265-268° C. IR (film) 3432, 3077, 2856, 1707, 1635, 1611, 1549, and 1504 cm$^{-1}$; $^1$H NMR. (CDCl$_3$) δ 8.59 (d, J=8.1 Hz, 1 H), 8.23 (d, J=8.1 Hz, 1 H), 7.85-7.80 (m, 3 H), 7.74 (d; J=7.4 Hz, 1 H), 7.63-7.51 (m, 4 H), 4.52 (t, J=7.3 Hz, 2 H), 2.81 (m, 2 H), 1.83 (m, 2 H) 1.65-1.52 (m, 4 H); ESIMS m/z (rel intensity) 333 (MH⁺, 100). Anal. ($C_{21}H_{21}ClN_2O_2 \cdot 0.75\ H_2O$) C, H, N.

6-(6-Aminohexyl)-5,6-dihydro-5,11-diketo-11H-indeno[1,2-c]isoquinoline Hydrochloride (5ap). Benz[d]indeno[1,2-b]pyran-5,11-dione (4d) (0.100 g, 0.403 mmol) was treated with 1,6-diaminohexane (0.234 g, 2.014 mmol) in CHCl₃ (40 mL) and the reaction mixture was heated at reflux for 16 h. The reaction mixture was allowed to cool to room temperature and washed with water (3×25 mL). The solution was dried over sodium sulfate, filtered, and treated with 2 M HCl in Et₂O (5 mL). After 30 min, the reaction mixture was filtered and the filter pad was washed with CHCl₃ (50 mL) and hexanes (50 mL) to provide an orange solid (0.125 g, 81%): mp 195° C. (dec). IR (film) 3435, 1660, 1630, 1610, and 1504 cm⁻¹; ¹H NMR (CDCl₃) δ 8.59 (d, J=7.8 Hz, 1 H), 8.23 (d, J=8.1 Hz, 1 H), 7.85-7.71 (m, 4 H), 7.61-7.51 (m, 4 H), 4.52 (t, J=7.3 Hz, 2 H), 2.78 (m, 2 H), 1.79 (m, 2 H), 1.59-1.39 (m, 6 H); ESIMS m/z (rel intensity) 347 (MH⁺, 100). Anal. ($C_{22}H_{23}ClN_2O_2 \cdot 0.5H_2O$) C, H, N.

General Procedure for the Preparation of Indenoisoquinoline Hydrochloride Salts. 3 M HCl in MeOH (10 mL) was slowly added to a solution of mono-Boc protected indenoisoquinoline (0.100 g, 0.188-0.217 mmol) in CHCl₃ (50 mL) at room temperature. After 2 h, the reaction mixture was concentrated and the residue was triturated with Et₂O. Filtration of the obtained solid provided the indenoisoquinoline as a hydrochloride salt. (Indenoisoquinoline hydrochloride salts 5al, 5am, and 5an were also prepared as described below.)

6-(7-Aminoheptyl)-5,6-dihydro-5,11-dioxo-11H-indeno[1,2-c]isoquinoline Hydrochloride (5aq). The general procedure provided the desired compound as a yellow-orange solid (0.085 g, 99%): mp 228-231° C. IR (KBr) 3436, 2931, 1702, 1650, 1611, 1549, 1504, and 759 cm⁻¹; ¹H NMR (DMSO-d₆) δ 8.60 (d, J=8.1 Hz, 1 H), 8.24 (d, J=8.2 Hz, 1 H), 7.85-7.80 (m, 1 H), 7.73 (d, J=7.4 Hz, 1 H), 7.63-7.49 (m, 6 H), 4.53 (t, J=7.0 Hz, 2 H), 2.78 (t, J=7.1 Hz, 2 H), 1.80 (m, 2 H), 1.55-1.35 (xn, 8 H); ESIMS m/z (rel intensity) 361 (MH⁺, 100). Anal. ($C_{23}H_{25}ClN_2O_2 \cdot 0.5H_2O$) C, H, N.

6-(8-Aminooctyl)-5,6-dihydro-5,11-dioxo-11H-indeno[1,2-c]isoquinoline Hydrochloride (5ar). The general procedure provided the desired compound as an orange solid (0.083 g, 95%): mp 182-185° C. IR (KBr) 3436, 2930, 1661, 1505, and 761 cm⁻¹; ¹H NMR (DMSO-d₆) δ 8.60 (d, J=8.5 Hz, 1 H), 8.24 (d, J=7.0 Hz, 1 H), 7.86-7.81 (m, 1 H), 7.73 (d, J=7.6 Hz, 1 H), 7.63-7.52 (m, 6 H), 4.52 (t, J=7.9 Hz, 2 H), 2.78 (t, J=7.3 Hz, 2 H), 1.79 (m, 2 H), 1.50 (m, 4 H), 1.31 (m, 6 H); ESIMS m/z (rel intensity) 375 (MH⁺, 100). Anal. ($C_{24}H_{27}ClN_2O_2 \cdot 0.75H_2O$) C, H, N.

6-(9-Aminononyl)-5,6-dihydro-5,11-dioxo-11H-indeno[1,2-c]isoquinoline Hydrochloride (5 as). The general procedure provided the desired compound as an orange solid (0.082 g, 94%): mp 204-207° C. IR (KBr) 3435, 2927, 1702, 1662, 1610, 1549, 1504, 1427, and 759 cm⁻¹; ¹H NMR (DMSO-d₆) δ 8.60 (d, J=8.3 Hz, 1 H), 8.24 (d, J=9.3 Hz, 1 H), 7.83-7.81 (m, 1 H), 7.73 (d, J=7.8 Hz, 1 H), 7.63-7.51 (m, 6 H), 4.52 (t, J=8.3 Hz, 2 H), 2.78 (t, J=7.3 Hz, 2 H), 1.79 (m, 2 H), 1.51 (m, 4 H), 1.28 (m, 8 H); ESIMS m/z (rel intensity) 389 (MH⁺, 100). Anal. ($C_{25}H_{29}ClN_2O_2 \cdot 0.75H_2O$) C, H, N.

6-(10-Aminodecyl)-5,6-dihydro-5,11-dioxo-11H-indeno[1,2-c]isoquinoline Hydrochloride (5at). The general procedure provided the desired compound as an orange solid (0.087 g, 91%): mp 189-192° C. JR (KBr) 3443, 2925, 2851, 1705, 1646, 1611, 1550, 1504, 1467, and 759 cm⁻¹; ¹H NMR (DMSO-d₆) δ 8.60 (d, J=7.9 Hz, 1 H), 8.23 (d, 0.1=7.5 Hz, 1 H), 7.83 (m, 1 H), 7.73 (d, J=8.0 Hz, 1 H), 7.63-7.51 (m, 6 H), 4.52 (t, J=7.4 Hz, 2 H), 2.76 (m, 2 H), 1.79 (m, 2 H), 1.49 (m, 4 H), 1.27 (m, 10 H); ESIMS m/z (rel intensity) 403 (MH⁺, 100). Anal. ($C_{26}H_{31}ClN_2O_2 \cdot 0.5H_2O$) C, H, N.

6-(11-Aminoundecyl)-5,6-dihydro-5,11-dioxo-11H-indeno[1,2-c]isoquinoline Hydrochloride (5au). The general procedure provided the desired compound as an orange solid (0.085 g, 88%): mp 125-129° C. IR (KBr) 3436, 2922, 2851, 1662, 1610, 1549, 1504, 1426, and 758 cm⁻¹; ¹H NMR (DMSO-d₆) δ 8.60 (d, J=8.0 Hz, 1 H), 8.23 (d, J=7.5 Hz, 1 H), 7.85 (m, 1 H), 7.72 (d, J=7.5 Hz, 1 H), 7.63-7.51 (m, 6 H), 4.51 (t, J=8.0 Hz, 2 H), 2.77 (t, J=7.6 Hz, 2 H), 1.78 (m, 2 H), 1.48 (m, 4 H), 1.25 (m, 12 H); ESIMS m/z (rel intensity) 417 (MH⁺, 100). Anal. ($C_{26}H_{31}ClN_2O_2 \cdot 1H_2O$) C, H, N.

6-(12-Aminododecyl)-5,6-dihydro-5,11-dioxo-11H-indeno[1,2-c]isoquinoline Hydrochloride (5av). The general procedure provided the desired compound as a yellow solid (0.087 g, 91%): mp 175-178° C. IR (KBr) 3435, 2927, 2850, 1704, 1644, 1506, 1466, and 762 cm⁻¹; ¹H NMR (DMSO-d₆) δ 8.59 (d, J=7.8 Hz, 1 H), 8.23 (d, J=7.5 Hz, 1 H), 7.83 (m, 1 H), 7.72 (d, J=7.8 Hz, 1 H), 7.63-7.51 (m, 6 H), 4.51 (t, J=7.5 Hz, 2 H), 2.76 (m, 2 H), 1.78 (m, 2 H), 1.51 (m, 4 H), 1.24 (m, 14 H); ESIMS m/z (rel intensity) 431 (MH⁺, 100). Anal. ($C_{28}H_{35}ClN_2O_2 \cdot 1.25H_2O$) C, H, N.

5,6-Dihydro-5,11-dioxo-6-(2-pyridylmethyl)-11H-indeno[1,2-c]isoquinoline (5aw). 2-(Aminomethyl)pyridine (0.054 g, 0.504 mmol) was added to a solution of benz[d]indeno[1,2-b]pyran-5,11-dione (4d) (0.100 g, 0.403 mmol) in CHCl₃ (50 mL) and the reaction mixture was heated at reflux for 16 h. The reaction mixture was allowed to cool to room temperature, washed with H₂O (3×25 mL), sat NaCl (25 mL), dried over sodium sulfate, and concentrated. The residue was washed with EtOAc, hexanes, and dried to provide a yellow solid (0.110 g, 81%): mp 240-242° C. IR (KBr) 1698, 1655, 1618, 1501, 1427, and 755 cm⁻¹; ¹H NMR (DMSO-d₆) δ 8.62 (d, J=8.0 Hz, 1 H), 8.56 (d, J=4.9 Hz, 1 H), 8.22 (d, J=8.1 Hz, 1 H), 7.97 (dt, J=7.8 Hz and 1.7 Hz, 1 H), 7.89 (m, 1 H), 7.61-7.37 (m, 7 H), 5.91 (s, 2 H); ESIMS m/z (rel intensity) 339 (MH⁺, 100). Anal. ($C_{22}H_{14}N_2O_2$) C, H, N.

5,6-Dihydro-5,11-dioxo-6-(3-pyridylmethyl)-11H-indeno[1,2-c]isoquinoline Hydrochloride (5ax). 3-(Aminomethyl)pyridine (0.054 g, 0.504 mmol) was added to a solution of benz[d]indeno[1,2-b]pyran-5,11-dione (4d) (0.100 g, 0.403 mmol) in CHCl₃ (50 mL) and the reaction mixture was heated at reflux for 16 h. The reaction mixture was allowed to cool to room temperature, washed with H₂O (3×25 mL), sat NaCl (25 mL), dried over sodium sulfate, and concentrated. The residue was diluted with CHCl₃ (40 mL), 3 M HCl in MeOH (10 mL) was added, and the reaction mixture was allowed to stir at room temperature for 2 h. The reaction mixture was concentrated, and the residue was washed with CHCl₃ to provide a pink solid (0.146 g, 97%): mp 274° C. (dec). IR (KBr) 2343, 2106, 1695, 1655, 1610, 1551, 1501, and 754 cm⁻¹; ¹H NMR (DMSO-d₆) δ 8.98 (s, 1 H), 8.78 (d, J=5.2 Hz, 1 H), 8.64 (d, J=8.1 Hz, 1 H), 8.36 (d, J=9.1 Hz, 1 H), 8.23 (d, J=7.5 Hz, 1 H), 7.90 (m, 2 H), 7.59-7.39 (m, 5 H), 5.89 (s, 2 H); ESIMS m/z (rel intensity) 339 (MH⁺, 100). Anal. ($C_{22}H_{15}ClN_2O_2$) C, H, N.

5,6-Dihydro-5,11-dioxo-6-(2-pyridylethyl)-11H-indeno[1,2-c]isoquinoline Hydrochloride (5ay), 2-(2-Aminoethyl)pyridine (0.098 g, 0.806 mmol) was added to a solution of benz[d]indeno[1,2-b]pyran-5,11-dione (4d) (0.100 g, 0.403 mmol) in CHCl₃ (50 mL) and the reaction mixture was heated at reflux for 16 h. The reaction mixture was allowed to cool to room temperature, washed with H₂O (3×25 mL), sat NaCl (25 mL), dried over sodium sulfate, and concentrated. The residue was diluted with CHCl₃ (40 mL), 3 M HCl in MeOH (10 mL) was added, and the reaction mixture was allowed to stir at room temperature for 2 h. The reaction mixture was concentrated, and the residue was washed with CHCl$_3$ to provide a yellow solid (0.146 g, 93%): mp 240° C. (dec). IR (KBr) 2307, 1698, 1659, 1610, 1548, 1504, 1429, and 760 cm$^{-1}$; $^1$H NMR (DMSO-d$_6$) δ 8.78 (d, J=5.5 Hz, 1 H), 8.57 (d, J=8.0 Hz, 1 H), 8.33 (m, 1 H), 8.02 (d, J=8.0 Hz, 1 H), 7.97 (d, J=8.0 Hz, 1 H), 7.90 (d, J=8.0 Hz, 1 H), 7.80 (m, 2 H), 7.61-7.44 (m, 4 H), 4.92 (t, J=6.5 Hz, 2 H), 3.59 (t, J=6.3 Hz, 2 H); ESIMS m/z (rel intensity) 353 (MH$^+$, 100). Anal. (C$_{23}$H$_{17}$ClN$_2$O$_2$) C, H, N.

5,6-Dihydro-5,11-dioxo-6-(3-pyridylethyl)-11H-indeno[1,2-c]isoquinoline (5az). 3-(2-Aminoethyl)pyridine (0.172 g, 0.604 mmol) was added to a solution of benz[d]indeno[1,2-b]pyran-5,11-dione (4d) (0.100 g, 0.403 mmol) in CHCl$_3$ (50 mL). Triethylamine (0.224 mL, 1.612 mmol) was added and the reaction mixture was heated at reflux for 16 h. The reaction mixture was allowed to cool to room temperature, washed with H$_2$O (3×25 mL), sat NaCl (25 mL), dried over sodium sulfate, and concentrated. The obtained precipitate was washed with EtOAc, hexanes, and dried to provide an orange solid (0.140 g, 99%): mp 220° C. (dec). IR (KBr) 1691, 1660, 1609, 1549, 1504, 1424, and 765 cm$^{-1}$; $^1$H NMR (DMSO-d$_6$) δ 8.90 (s, 1 H), 8.73 (d, J=. 5.6 Hz, 1 H), 8.59 (d, J=8.1 Hz, 1 H), 8.44 (d, J=7.9 Hz, 1 H), 8.10 (d, J=8.1 Hz, 1 H), 7.88 (m, 3 H), 7.61-7.48 (m, 4 H), 4.87 (t, J=6.7 Hz, 2 H), 3.37 (t, J=6.3 Hz, 2 H); ESIMS m/z (rel intensity) 353 (MH$^+$, 100). Anal. (C$_{23}$H$_{16}$N$_2$O$_2$.0.55H$_2$O) C, H, N.

cis-4-Carboxy-N-(3-chloropropyl)-3,4-dihydro-3-(4-methoxyphenyl)-1(2H)isoquinolone (8a). Homophthalic anhydride (6a) (3.065 g, 18.90 mmol) was added to a chloroform (125 mL) solution of 4-methoxybenzylidene-(3-chloro-1-propylamine) (7a) (4.000 g, 18.90 mmol) and the reaction mixture was allowed to stir at room temperature for 3 h. The obtained precipitate was filtered, washed with chloroform (100 mL), and dried to provide an off-white solid (4.723 g, 67%): mp 180-181° C. IR (KBr) 3437, 2957, 1740, 1622, 1598, 1573, 1514, 1479, 1258, and 1173 cm$^{-1}$; $^1$H NMR (CD$_3$OD) δ 8.10 (dd, J=7.6 Hz and 1.4 Hz, 1 H), 7.63 (d, J=7.6 Hz, 1 H), 7.55 (dt, J=7.4 Hz and 1.5 Hz, 1 H), 7.50 (m, 1 H), 6.97 (m, 2 H), 6.75 (m, 2 H), 5.13 (d, J=6.3 Hz, 1 H), 4.76 (d, J=6.2 Hz, 1 H), 3.98 (m, 1 H), 3.70 (s, 3 H), 3.61 (m, 2 H), 3.22 (m, 1 H), 2.13-2.01 (m, 2 H); ESIMS m/z (rel intensity) 374/376 (MH$^+$, 100/33). Anal. (C$_{20}$H$_{20}$ClNO$_4$) C, H, N.

Benzylidene-(3-bromo-1-propylamine) (7b). The hydrobromide salt of 3-bromopropylamine (5.364 g, 24.50 mmol) was treated with triethylamine (4 mL) in CHCl$_3$ (100 mL) and allowed to stir at room temperature for 5 min. Benzaldehyde (2.000 g, 18.85 mmol) and magnesium sulfate (6.000 g) were added and the reaction mixture was allowed to stir at room temperature for 16 h. The reaction mixture was filtered and the filter pad was washed with CHCl$_3$ (50 mL). The filtrate was washed with water (3×50 mL), sat NaCl (50 mL), dried over sodium sulfate, and concentrated to provide a yellow oil (4.262 g, 100%). IR (film) 1645, 754, and 693 cm$^{-1}$; $^1$H NMR (CDCl$_3$) δ 8.34 (s, 1 H), 7.76 (m, 2 H), 7.44 (m, 3 H), 3.78 (dt, J=6.3 Hz and 1.3 Hz, 2 H), 3.52 (t, J=6.5 Hz, 2 H), 2.31 (pent, J=6.4 Hz, 2 H); ESIMS m/z (rel intensity) 226/228 (MH$^+$, 100/91). Anal. (C$_{10}$H$_{12}$BrN) C, H, N.

cis-4-Carboxy-3,4-dihydro-N-(3-bromopropyl)-3-phenyl-7-nitro-1(2H)isoquinolone (8b). 4-Nitrohomophthalic anhydride (6b) (3.664 g, 17.69 mmol) was added to a chloroform (125 mL) solution of benzylidene-(3-bromo-1-propylamine) (7b) (4.000 g, 17.69 mmol), and the reaction mixture was allowed to stir at room temperature for 1.25 h. The obtained precipitate was filtered, washed with chloroform (150 mL), and dried to provide a yellow solid (6.278 g, 82%): mp 158-160° C. IR (KBr) 3435, 3061, 1743, 1638, 1520, 1349, and 1191 cm$^{-1}$; $^1$H NMR (CD-30D) δ 8.90 (d, J=2.5 Hz, 1 H), 8.38 (dd, J=8.7 Hz and 2.6 Hz, 1 H), 7.98 (m, 1 H), 7.25-7.19 (m, 3 H), 7.07-7.03 (m, 2 H), 5.32 (d, J=6.2 Hz, 1 H), 4.96 (d, J=6.2 Hz, 1 H), 3.99 (m, 1 H), 3.52 (m, 2 H), 3.26 (m, 1 H), 2.26-2.12 (m, 2 H); negative ion ESIMS m/z (rel intensity) 431/433 [(M-H$^+$)$^-$, 12/9]. Anal. (C$_{19}$H$_{17}$BrN$_2$O$^5$.1.0H$_2$O) C, H, N.

6-(3-Chloropropyl)-5,6-dihydro-9-methoxy-5,11-dioxo-11H-indeno[1,2-c]isoquinoline (5bc). Thionyl chloride (2 mL) was added to a solution of cis-4-carboxy-N-(3-chloropropyl)-3,4-dihydro-3-(4-methoxyphenyl)-1(2H)isoquinolone (8a) (0.510 g, 1.364 mmol) in benzene (40 mL). The reaction mixture was heated at reflux for 30 min, allowed to cool to room temperature, and concentrated. The residue was diluted with nitrobenzene (20 mL), chilled in an ice bath, and aluminum chloride (0.364 g, 2.728 mmol) was added. The reaction mixture was removed from the bath and heated at 100° C. for 1.5 h. Ice water (100 mL) was added and the solution was extracted with CHCl$_3$ (3×50 mL). The combined organic layer was washed with sat NaHCO$_3$ (3×50 mL), sat NaCl (50 mL), and dried over sodium sulfate. The solution was concentrated, hexanes (250 mL) were added, and liquid was decanted. The obtained solid was washed with hexanes (100 mL) and the liquid was again decanted. The solid was purified by flash column chromatography (SiO$_2$), eluting with chloroform, to provide a purple-red solid (0.082 g, 17%) that was precipitated from EtOAc/hexanes: mp 195-198° C. IR (KBr) 1662, 1611, 1505, 1481, 1432, and 1299 cm$^{-1}$; $^1$H NMR (CDCl$_3$) δ 8.67 (d, J=8.1 Hz, 1 H), 8.31 (dd, J=8.2 Hz and 0.7 Hz, 1 H), 7.73 (m, 1 H), 7.66 (d, J=8.4 Hz, 1 H), 7.45 (m, 1 H), 7.22 (d, J=2.6 Hz, 1 H), 6.86 (dd, J=8.4 Hz and 2.6 Hz, 1 H), 4.67 (m, 2 H), 3.89 (s, 3 H), 3.83 (m, 2 H), 2.43 (m, 2 H); CIMS m/z (rel intensity) 354/356 (MH$^+$, 100/30). Anal. (C$_{20}$H$_{16}$ClNO$_3$) C, H, N.

6-(3-Bromopropyl)-5,6-dihydro-5,11-dioxo-3-nitro-11H-indeno[1,2-c]isoquinoline (5bb). Thionyl chloride (5 mL) was added to a solution of cis-4-carboxy-3,4-dihydro-N-(3-bromopropyl)-3-phenyl-7-nitro-1(2 H)isoquinolorie (8b) (1.000 g, 2.308 mmol) in benzene (50 mL). The reaction mixture was heated at reflux for 30 min, allowed to cool to room temperature, and concentrated. The residue was diluted with nitrobenzene (30 mL), chilled in an ice bath, and aluminum chloride (0.616 g, 4.616 mmol) was added. The reaction mixture was removed from the bath and heated at 100° C. for 1 h. Ice water (100 mL) was added and the solution was extracted with CHCl$_3$ (3×100 mL). The combined organic layer was washed with sat NaHCO$_3$ (3×50 mL), sat NaCl (50 mL) and dried over sodium sulfate. The solution was concentrated, hexanes (900 mL) were added, and liquid was decanted. The obtained solid was washed with hexanes (100 mL) and the liquid was again decanted. The crude solid was purified by flash column chromatography (SiO$_2$), eluting with chloroform, to provide an orange solid (0.432 g, 45%): mp 258-260 (dec). IR (film) 1672, 1612, 1560, 1503, 1428, and 1337 cm$^{-1}$; $^1$H NMR (CDCl$_3$) δ 9.20 (d, J=2.4 Hz, 1 H), 8.89 (d, J=8.9 Hz, 1 H), 8.52 (dd, J=9.0 Hz and 2.4 Hz, 1 H), 7.92 (m, 1 H), 7.75 (m, 1 H), 7.57-7.52 (m, 2 H), 4.76 (m, 2 H), 3.70 (t, J=6.2 Hz, 2 H), 2.54 (m, 2 H); CIMS m/z (rel intensity) 413/415 (MH$^+$, 100/82). Anal. (C$_{19}$H$_{13}$BrN$_2$O$_4$) C, H, N.

Bis{(5,6-dihydro-5,11-diketo-11H-indeno[1,2-c]isoquinoline)-6-ethyl}amine (12a). 2,2'-Diaminodiethylamine (11a) (0.3 g, 2.91 mmol) was added to a stirred solution of indenobenzopyran 4d (2.17 g, 8.72 mmol) in CHCl$_3$ (200 mL) and the mixture was stirred under reflux for 48 h. The reaction mixture was then cooled and the resultant orange solid was filtered through a sintered glass funnel and washed with chloroform (30 mL) to provide pure bisindenoisoquinoline 12a (0.75 g, 46%) as an orange solid: mp 240-242° C. $^1$H NMR (DMSO-d$_6$) δ 8.51 (d, J=8.9 Hz, 2 H), 8.11 (d, J=7.7 Hz, 2 H), 7.76 (bs, 4 H), 7.47 (bs, 4 H), 7.36 (bs, 4 H), 4.51 (bs, 4 H), 3.03 (bs, 4 H); ESIMS m/z (rel intensity) (MH$^+$, 100). Anal. Calcd for C$_{36}$H$_{25}$N$_3$O$_4$: C, 76.72; H, 4.47; N, 7.46. Found: C, 76.35; H, 4.45; N, 7.39.

Bis{(5,6-dihydro-5,11-diketo-11H-indeno[1,2-c]isoquinoline)}-(6-ethyl,6'-propyl)amine (12b). 2-Aminoethyl-3-aminopropylamine (11b) (0.2 g, 1.71 mmol) was added to a stirred solution of indenobenzopyran 4d (1.06 g, 4.27 mmol) in CHCl$_3$ (200 mL) and the reaction mixture was stirred under reflux for 48 h. The reaction mixture was then cooled and the resultant orange solid was filtered through a sintered glass funnel and washed with chloroform-methanol mixture (2:8, 50 mL) to provide pure bisindenoisoquinoline 12b (0.72 g, 73%) as an orange solid: mp 250-252° C. $^1$H NMR (CDCl$_3$) δ 8.69 (d, J=8.5 Hz, 2 H), 8.29 (t, J=7.4 Hz, 2 H), 7.70 (t, J=7.4 Hz, 2 H), 7.62 (m, 2 H), 7.46-7.37 (m, 8 H), 4.69 (t, J=7.3 Hz, 2 H), 4.61 (t, J=7.5 Hz, 2 H), 3.16 (t, J=7.3 Hz, 2 H), 2.89 (t, J=6.0 Hz, 2 H), 2.05 (m, 2 H); ESIMS m/z (rel intensity) 578 (MH$^+$, 100); HRESIMS calcd for (C$_{37}$H$_{27}$N$_3$O$_4$)H$^+$: 578.2079. Found: 578.2087.

Bis{(5,6-dihydro-5,11-diketo-11H-indeno[1,2-c]isoquinoline)-6-propyl}amine (12c). 3,3'-Diaminodipropylamine (11c) (0.3 g, 2.29 mmol) was added to a stirred solution of indenobenzopyran 4d (1.7 g, 6.86 mmol) in CHCl$_3$ (200 mL) and the mixture was stirred under reflux for 48 h. The bright orange reaction mixture was purified by flash column chromatography (SiO$_2$/CHCl$_3$ to 3% MeOH in CHCl$_3$) to afford pure bisindenoisoquinoline 12c (0.54 g) in 40% yield as a dark orange solid: mp 223-225° C. $^1$H NMR (CDCl$_3$) δ 8.65 (d, J=8.1 Hz, 2 H), 8.27 (d, J=8.1 Hz, 2 H), 7.67 (t, J=7.1 Hz, 4 H), 7.57 (d, J=7.0 Hz, 2 H), 7.41 (t, J=7.1 Hz, 4 H), 7.33 (t, J=7.1 Hz, 2 H), 4.62 (t, J=7.3 Hz, 4 H), 2.84 (t, J=6.4 Hz, 4 H), 2.08 (m, 4 H); $^1$H NMR (DMSO-d$_6$) δ 8.53 (d, J=7.8 Hz, 2 H), 8.18 (d, J=7.9 Hz, 2 H), 7.87 (d, J=7.4 Hz, 2 H), 7.79 (t, J=7.6 Hz, 2 H), 7.54 (t, J=5.8 Hz, 4 H), 7.46 (m, 4 H), 4.53 (t, J=6.9 Hz, 4 H), 2.80 (bs, 4 H), 1.99 (m, 4 H); ESIMS m/z (rel intensity) 592 (MH$^+$, 100). Anal. Calcd for C$_{38}$H$_{29}$N$_3$O$_4$·1.6H$_2$O: C, 73.56; H, 5.23; N, 6.77. Found: C, 73.18; H, 4.93; N, 6.47.

Bis{(5,6-dihydro-5,11-diketo-11H-indeno[1,2-c]isoquinoline)-6-propyl}methylamine (12d). 3,3'-Diamino-N-methyl dipropylamine (11d) (0.10 g, 0.69 mmol) was added to a stirred solution of indenobenzopyran 4d (0.38 g, 1.52 mmol) in CHCl$_3$ (150 mL) and the reaction mixture was stirred under reflux for 48 h. The reaction mixture was cooled to room temperature and purified by flash column chromatography (SiO$_2$/CHCl$_3$ to 5% MeOH in CHCl$_3$) to provide bisindenoisoquinoline 12d (340 mg, 82%) as a red solid: mp 230-232° C. $^1$H NMR (CDCl$_3$) δ 8.67 (d, J=8.1 Hz, 2 H), 8.30 (d, J=7.6 Hz, 2 H), 7.72-7.66 (dt, J=8.3 and 2.8 Hz, 4 H), 7.59 (d, J=7.1 Hz, 2 H), 7.48-7.40 (q, J=7.5 Hz, 4 H), 7.33 (t, 7.3 Hz, 2 H), 4.63 (t, J=8.0 Hz, 4 H), 2.66 (t, J=6.5 Hz, 4 H), 2.37 (s, 3 H), 2.13-2.04 (m, 4 H); ESIMS m/z (rel intensity) 606 (MH$^+$, 100). Anal. Calcd for C$_{39}$H$_{31}$N$_3$O$_4$·0.4 CHCl$_3$: C, 72.42; H, 4.84; N, 6.43. Found: C, 72.67; H, 5.05; N, 6.32.

Bis{(5,6-dihydro-5,11-diketo-11H-indeno[1,2-c]isoquinoline)}-(6-propyl,6'-butyl)amine (12e). 4-Aminobutyl-3-aminopropylamine (11e) (0.2 g, 1.38 mmol) was added to a stirred solution of indenobenzopyran 4d (0.75 g, 3.03 mmol) in CHCl$_3$ (200 mL) and the reaction mixture was stirred under reflux for 48 h. The reaction mixture was then cooled and the resultant orange solid was filtered through a sintered funnel and washed with chloroform-methanol mixture (5:1, 50 mL) to provide pure bisindenoisoquinoline 12e (0.63 g, 76%) as an orange solid: mp 228-230° C. $^1$H NMR (CDCl$_3$) δ 8.67 (d, J=8.1 Hz, 2 H), 8.28 (d, J=8.1 Hz, 2 H), 7.70-7.65 (m, 2 H), 7.59 (d, J=6.8 Hz, 2 H), 7.52 (d, J=7.4 Hz, 2 H), 7.45-7.24 (m, 6 H), 4.61 (t, J=7.3 Hz, 2 H), 4.55 (t, J=7.9 Hz, 2 H), 2.84 (t, J=6.5 Hz, 2 H), 2.80 (t, J=6.8 Hz, 2 H), 2.15-2.10 (m, 2 H), 2.00-1.95 (m, 2 H), 1.84-1.77 (m, 2 H); ESIMS m/z (rel intensity) 606 (MH$^+$, 100); HRESIMS calcd for (C$_{39}$H$_{31}$N$_3$O$_4$)H$^+$: 606.2393. Found: 606.2402.

Bis-1,3-{(5,6-dihydro-5,11-diketo-11H-indeno[1,2-c]isoquinoline)-(6-ethyl-tert-BOCamino)}propane (13a). N,N'-Bis(2-aminoethyl)-1,3-propanediamine (11g) (0.10 g, 0.62 mmol) was added to a stirred solution of indenobenzopyran 4d (0.34 g, 1.37 mmol) in CHCl$_3$ (150 mL) and the reaction mixture was stirred under reflux for 72 h, providing bisindenoisoquinoline 12g as a crude intermediate. After allowing the reaction mixture to cool to room temperature, Et$_3$N (0.35 mL, 2.50 mmol) and Boc$_2$O (0.34 g, 1.56 mmol) were added, and the reaction mixture was stirred at room temperature for 8 h. The crude reaction mixture was purified by flash column chromatography (SiO$_2$/20% EtOAc in hexane, then 1-5% MeOH in CHCl$_3$) to provide Doc-protected bisindenoisoquinoline 13a (380 mg, 74%) as an orange solid: mp 238-240° C. $^1$H NMR (CDCl$_3$) δ 8.63 (d, J=8.0 Hz, 1 H), 8.16 (d, J=7.4 Hz, 2 H), 7.65-7.58 (m, 5 H), 7.53-7.45 (m, 2 H), 7.38-7.29 (m, 5 H), 4.63 (bs, 4 H), 3.62 (bs, 4 H), 3.32 (bs, 4 H), 1.90 (bs, 2 H), 1.41 (s, 18 H); ESIMS m/z (rel intensity) 821 (MH$^+$, 10), 721 (MH$^+$-Boc, 100). Anal. Calcd for C$_{49}$H$_{48}$N$_4$O$_8$: C, 71.69; H, 5.89; N, 6.82. Found: C, 71.35; H, 5.99; N, 6.68.

Bis-1,2-{(5,6-dihydro-5,11-diketo-11H-indeno[1,2-c]isoquinoline)-(6-propyl-tert-BOCamino)}ethane (13b). N,N'-Bis(3-aminopropyl)-1,2-ethanediamine (11h) (0.16 g, 0.85 mmol) was added to a stirred solution of indenobenzopyran 4d (0.46 g, 1.87 mmol) in CHCl$_3$ (150 mL) and the reaction mixture was stirred under reflux for 72 h, providing bisindenoisoquinoline 12h as a crude intermediate. Upon allowing the reaction mixture to cool to room temperature, Et$_3$N (0.6 mL, 4.24 mmol) and Boc$_2$O (0.56 g, 2.60 mmol) were added to the reaction mixture and the mixture was allowed to stir at room temperature for 8 h. The crude reaction mixture was purified by flash column chromatography (SiO$_2$/20% EtOAc in hexane, then 1-5% MeOH in CHCl$_3$) to provide Boc-protected bisindenoisoquinoline 13b (550 mg, 76%) as an orange solid: mp 106-108° C. $^1$H NMR (CDCl$_3$) δ 8.60 (bs, 2 H), 8.23 (bs, 2 H), 7.65 (bs, 2 H), 7.55 (d, J=6.7 Hz, 2 H), 7.40-7.32 (m, 8 H), 4.48 (bs, 4 H), 3.45 (bs, 8 H), 2.12 (bs, 4 H), 1.44 (s, 9 H), 1.39 (s, 9 H); ESIMS m/z (rel intensity) 835 (MH$^+$, 22), 735 (MH$^+$-Boc, 100). Anal. Calcd for C$_{50}$H$_{50}$N$_4$O$_8$·0.3H$_2$O: C, 71.46; H, 6.07; N, 6.67. Found: C, 71.15; H, 6.19; N, 6.61.

Bis-1,3-{(5,6-dihydro-5,11-diketo-11H-indeno[1,2-c]isoquinoline)-(6-propyl-tert-BOCamino)}propane (13c). N,N'-Bis(3-aminopropyl)-1,3-propanediamine (11j) (0.15 g, 0.74 mmol) was added to a stirred solution of indenobenzopyran 4d (0.40 g, 1.63 mmol) in CHCl$_3$ (150 mL) and the reaction mixture was stirred under reflux for 72 h, providing bisindenoisoquinoline 12j as a crude intermediate. Upon allowing the reaction mixture to cool to room temperature, Et$_3$N (0.53 mL, 3.78 mmol) and Boc$_2$O (0.49 g, 2.27 mmol) were added to the reaction mixture and the mixture was allowed to stir at room temperature for 8 h. The crude reaction mixture was purified by flash column chromatography (SiO$_2$/20% EtOAc in hexane, then 1-5% MeOH in CHCl$_3$) to provide Boc-protected bisindenoisoquinoline 13c (450 mg, 70%) as an orange solid: mp 86-88° C. $^1$H NMR (CDCl$_3$) δ 8.63 (d, J=8.1 Hz, 2 H), 8.24 (d, J=7.6 Hz, 2 H), 7.65 (t, J=7.3 Hz, 2 H), 7.55 (d, J=6.7 Hz, 2 H), 7.40-7.31 (m, 8 H), 4.49 (bs, 4 H), 3.44 (bs, 4 H), 3.27 (apparent t, J=6.2 Hz, 4 H), 2.08 (bs, 4 H), 1.86 (bs, 2 H), 1.41 (bs, 18 H); ESIMS m/z (relative intensity) 849

(MH+, 3), 749 (MH+–Boc, 37), 649 (MH+–2xBoc, 100). Anal. Calcd for $C_{51}H_{52}N_4O_8 \cdot 0.5H_2O$: C, 71.39; H, 6.23; N, 6.53. Found: C, 70.99; H, 620; N, 6.62.

Bis-1,4-{(5,6-dihydro-5,11-diketo-11H-indeno[1,2-c]isoquinoline)-(6-propyl-tent-BOCamino)}butane (13d). N,N'-Bis(3-aminopropyl)-1,4-butanediamine (11k) (0.10 g, 0.50 mmol) was added to a stirred solution of indenobenzopyran 4d (0.27 g, 1.09 mmol) in CHCl$_3$ (150 mL) and the reaction mixture was stirred under reflux for 72 h, providing bisindenoisoquinoline 12k as a crude intermediate. Upon allowing the reaction mixture to cool to room temperature, Et$_3$N (0.28 mL, 2.00 mmol) and Boc$_2$O (0.27 g, 1.25 mmol) were added to the reaction mixture and the mixture was allowed to stir at room temperature for 8 h. The crude reaction mixture was purified by flash column chromatography (SiO$_2$/20% EtOAc in hexane, and then 1-5% MeOH in CHCl$_3$) to provide Boc-protected bisindenoisoquinoline 13d (350 mg, 82%) as an orange solid: mp 92-94° C. $^1$H NMR (CDCl$_3$) δ 8.66 (d, J=8.1 Hz, 2 H), 8.28 (d, J=8.0 Hz, 2 H), 7.68 (t, J=7.7 Hz, 2 H), 7.60 (d, J=7.1 Hz, 2 H), 7.43-7.34 (m, 8 H), 4.51 (t, J=8.3 Hz, 4 H), 3.44 (bs, 4 H), 3.28 (bs, 4 H), 2.11 (m, 4 H), 1.50 (bs, 4 H), 1.41 (s, 18 H); ESIMS m/z (rel intensity) 863 (MH+, 13), 763 (MH+–Boc, 100). Anal. Calcd for $C_{52}H_{54}N_4O_8 \cdot 0.9 \, H_2O$: C, 71.04; H, 6.40; N, 6.37. Found: C, 70.77; H, 6.39; N, 6.26.

Bis{(5,6-dihydro-5,11-diketo-11H-indeno[1,2-c]isoquinoline)}-(6-ethyl,6'-propyl)ammonium Trifluoroacetate (14a). Bisindenoisoquinoline 12b (0.5 g, 0.87 mmol) was dissolved in neat CF$_3$COOH (30 mL) and the reaction mixture was stirred at room temperature for 1 h. The reaction mixture was concentrated, diluted with chloroform (50 mL), and the resultant solid was filtered through a sintered glass funnel and further washed with methanol (50 mL) to give bisindenoisoquinoline 14a (0.48 g, 80%) as a red solid: mp 240-242° C. $^1$H NMR (DMSO-d$_6$) δ 8.71 (bs, 1 H, —NH—), 8.56 (d, J=7.8 Hz, 2 H), 8.17 (d, J=8.6 Hz, 2 H), 7.83-7.75 (m, 4 H), 7.57-7.50 (m, 8 H), 4.79 (bs, 4 H), 4.57 (bs, 2 H), 3.46 (bs, 2 H), 3.17 (bs, 2 H), 2.18 (bs, 2 H); ESIMS m/z (rel intensity) 578 (MH+—CF$_3$COOH, 100). Anal. Calcd for $C_{39}H_{28}N_3O_6F_3 \cdot 0.3 \, H_2O$: C, 67.20; H, 4.14; N, 6.03. Found: C, 66.85; H, 4.12; N, 5.93.

Bis{(5,6-dihydro-5,11-diketo-11H-indeno[1,2-c]isoquinoline)}-(6-propyl,6'-butyl)amine Hydrochloride (14b). 2 M HCl in ether (6.2 in L, 2.4 mmol) was added to a stirred solution of bisindenoisoquinoline 12e (0.5 g, 0.83 mmol) in chloroform (100 mL) and the reaction mixture was stirred at room temperature for 2 h. The reaction mixture was filtered through a sintered glass funnel and the solid was washed with chloroform (50 mL) and methanol (50 mL) to give bisindenoisoquinoline hydrochloride 14b (0.44 g, 83%) as an orange solid: mp 280-282° C. (dec). $^1$H NMR (DMSO-d$_6$) δ 8.66 (bs, 1 H), 8.54 (d, J=7.9 Hz, 2 H), 8.18 (d, J=8.6 Hz, 2 H), 7.83-7.7 d 0 (m, 4 H), 7.58-7.40 (m, 8 H), 4.54-4.42 (m, 4 H), 3.06 (bs, 2 H), 2.96 (bs, 2 H), 2.16 (bs, 2 H), 1.84 (bs, 2 H), 1.76 (bs, 2 H); ESIMS m/z (rel intensity) 606 (MH+, 100). Anal. Calcd for $C_{39}H_{32}N_3O_4Cl \cdot 1.1 \, H_2O$: C, 70.76; H, 5.21; N, 6.35. Found: C, 70.48; H, 5.12; N, 6.23.

Bis-1,2-{(5,6-dihydro-5,11-diketo-11H-indeno[1,2-c]isoquinoline)-6-ethylamino}ethane Bis(trifluoroacetate) (14c). N,N'-Bis(2-aminoethyl)-1,2-ethanediamine (11f) (0.4 g, 2.74 mmol) was added to a stirred solution of indenobenzopyran 4d (1.49 g, 6.02 mmol) in CHCl$_3$ (200 mL) and the reaction mixture was stirred under reflux for 48 h. The reaction mixture was then cooled and the resultant orange solid was filtered through a sintered glass funnel and washed with chloroform (50 mL) to provide bisindenoisoquinoline 12f (0.57 g, 69%) as an insoluble orange solid. Intermediate 12f (0.5 g, 0.83 mmol) was dissolved in neat CF$_3$COOH (30 mL) and stirred at room temperature for 30 min. The reaction mixture was concentrated, diluted with chloroform (50 mL), and filtered through a sintered glass funnel to provide bisindenoisoquinoline 14c (0.57 g, 83%) as an orange solid: mp 230-232° C. $^1$H NMR (DMSO-d$_6$) δ 8.97 (bs, 2 H), 8.59 (d, J=8.1 Hz, 2 H), 8.23 (d, J=8.0 Hz, 2 H), 7.89-7.83 (td, J=1.2 and 8.3 Hz, 2 H), 7.76 (d, J=6.8 Hz, 2 H), 7.63-7.50 (m, 8 H), 4.83 (bs, 4 H), 3.52 (bs, 4 H), 3.32 (bs, 4 H); ESIMS m/z (rel intensity) 607 (MH+, 100). Anal. Calcd for $C_{42}H_{32}N_4O_8F_6 \cdot 0.4H_2O$: C, 59.92; H, 3.93; N, 6.66. Found: C, 59.56; H, 4.04; N, 6.62.

Bis-1,3-{(5,6-dihydro-5,11-diketo-11H-indeno[1,2-c]isoquinoline)-6-ethylamino}propane Bis(trifluoroacetate) (14d). Boc-protected bisindenoisoquinoline 13a (0.3 g, 0.36 mmol) was dissolved in neat CF$_3$COOH (30 mL) and the mixture was stirred at room temperature for 1 h. The reaction mixture was concentrated and the resultant solid was diluted with chloroform (50 mL) and filtered through a sintered glass funnel to provide bisindenoisoquinoline 14d (0.28 g, 92%) as an orange solid: mp 244-246° C. $^1$H NMR (DMSO-d$_6$) δ 8.93 (bs, 2 H), 8.60 (d, J=8.4 Hz, 2 H), 8.23 (d, J=7.9 Hz, 2 H), 7.87 (t, J=7.5 Hz, 2 H), 7.79 (d, J=7.8 Hz, 2 H), 7.60-7.52 (m, 8 H), 4.82 (bs, 4 H), 3.47 (bs, 4 H), 3.07 (bs, 4 H), 1.95 (bs, 2 H); ESIMS m/z (rel intensity) 621 (MH, 100), 274 (7). Anal. Calcd for $C_{43}H_{34}F_6N_4O_8 \cdot 1.7 \, H_2O$: C, 58.73; H, 4.29; N, 6.37. Found: C, 58.38; H, 4.32; N, 6.26.

Bis-1,2-{(5,6-dihydro-5,11-diketo-11H-indeno[1,2-c]isoquinoline)-6-propylamino}ethane Bis(trifluoroacetate) (14e). Boc-protected bisindenoisoquinoline 13b (0.5 g, 0.79 mmol) was dissolved in neat CF$_3$COOH (30 mL) and the mixture was stirred at room temperature for 30 min. The reaction mixture was concentrated, diluted with chloroform (50 mL), and the resultant solid was filtered through a sintered glass funnel to afford bisindenoisoquinoline 14e (0.61 g, 90%) as a pale red solid: mp 220-222° C. $^1$H NMR (DMSO-d$_6$) δ 8.84 (bs, 2 H), 8.57 (d, J=8.1 Hz, 2 H), 8.20 (d, J=7.8 Hz, 2 H), 7.85-7.77 (m, 4 H), 7.60-7.48 (m, 8 H), 4.57 (t, J=6.6 Hz, 4 H), 3.23 (bs, 4 H), 3.18 (bs, 4 H), 2.16 (m, 4 H); ESIMS m/z (rel intensity) 635 (MH+, 61). Anal. Calcd for $C_{44}H_{36}N_4O_8F_6 \cdot 1.4H_2O$: C, 59.51; H, 4.40; N, 6.31. Found: C, 59.15; H, 4.06; N, 6.06.

Bis-1,4-{(5,6-dihydro-5,11-diketo-11H-indeno[1,2-c]isoquinoline)-6-propyl}piperazine Bis(trifluoroacetate) (14f). 1,4-Bis(3-aminopropyl)piperazine 11i (0.10 g, 0.50 mmol) was added to a stirred solution indenobenzopyran 4d (0.27 g, 1.10 mmol) in CHCl$_3$ (150 mL) and the reaction mixture was stirred under reflux for 60 h. The reaction mixture was then cooled and the resultant red solid was filtered off through a sintered glass funnel, washed with chloroform (50 mL) and dried to provide intermediate 12i. This compound was further treated with CF$_3$COOH (40 mL) and the mixture was stirred at room temperature for 2 h. The reaction mixture was concentrated, diluted with chloroform (50 mL), and the resultant solid was filtered and washed with methanol-chloroform (1:9) to provide bisindenoisoquinoline 14f (430 mg, 86%) as red solid: mp 256-258° C. $^1$H NMR (CDCl$_3$) δ 8.57 (d, J=8.0 Hz, 2 H), 8.21 (d, J=8.1 Hz, 2 H), 7.85-7.77 (m, 4 H), 7.58-7.48 (m, 8 H), 4.55 (bs, 4 H), 3.34 (bs, 4 H), 3.02 (bs, 4 H), 2.72 (bs, 2 H), 2.47 (bs, 2 H, merged with DMSO-d$_6$ protons), 2.09 (bs, 4 H); ESIMS m/z (rel intensity) 661 (MH+, 100). Anal. Calcd for $C_{46}H_{38}F_6N_4O_8 \cdot 0.4 \, H_2O$: C, 61.66; H, 4.37; N, 6.25. Found: C, 61.27; H, 4.61; N, 6.18.

Bis-1,3-{(5,6-dihydro-5,11-diketo-11H-indeno[1,2-c]isoquinoline)-6-propylamino}propane Bis(trifluoroacetate) (14g). Boc-protected bisindenoisoquinoline 13c (0.3 g, 0.35 mmol) was dissolved in neat CF$_3$COOH (30 mL) and the mixture was stirred at room temperature for 1 h. The reaction mixture was concentrated and the resultant solid was diluted with chloroform (50 mL) and filtered through a sintered glass funnel to provide bisindenoisoquinoline 14g (0.27 g, 89%) as an orange solid: mp 225-227° C. $^1$H NMR (DMSO-$d_6$) δ 8.66 (bs, 2 H), 8.56 (d, J=8.1 Hz, 2 H), 8.19 (d, J=7.9 Hz, 2 H), 7.79 (t, J=7.9 Hz, 4 H), 7.59-7.48 (m, 8 H), 4.57 (bs, 4 H), 3.09 (bs, 4 H), 2.96 (bs, 4 H), 2.15 (bs, 4 H), 1.87 (bs, 2 H); ESIMS m/z (relative intensity) 649 (MH$^+$, 100). Anal. Calcd for $C_{45}H_{38}F_6N_4O_8$.1.3 $H_2O$: C, 60.04; H, 4.55; N, 6.22. Found: C, 59.71; H, 4.41; N, 6.03.

Bis-1,4-{(5,6-dihydro-5,11-diketo-11H-indeno[1,2-c]iso-quinoline)-6-propylamino}butane Bis(trifluoroacetate) (14h). Boc-protected bisindenoisoquinoline 13d (0.3 g, 0.35 mmol) was dissolved in neat $CF_3COOH$ (20 mL) and the mixture was stirred at room temperature for 1 h. The reaction mixture was concentrated and the resultant solid was diluted with chloroform (50 mL) and filtered through a sintered glass funnel to provide bisindenoisoquinoline 14h (0.28 g, 90%) as an orange solid: mp 236-238° C. $^1$H NMR (DMSO-$d_6$) δ 8.58 (d, J=8.0 Hz, 2 H), 8.52 (bs, 2 H), 8.20 (d, J=8.1 Hz, 2 H), 7.84-7.78 (m, 4 H), 7.60-7.49 (m, 8 H), 4.57 (t, J=6.6 Hz, 4 H), 3.08 (bs, 4 H), 2.92 (bs, 4 H), 2.16 (m, 4 H), 1.59 (bs, 4 H); ESIMS m/z (rel intensity) 663 (MH$^+$, 100). Anal. Calcd for $C_{46}H_{40}F_6N_4O_8$.0.4 $H_2O$: C, 61.52; H, 4.58; N, 6.24. Found: C, 61.22; H, 4.62; N, 6.09.

Bis{(5,6-dihydro-5,11-diketo-11H-indeno[1,2-c]iso-quinoline)-6-ethylamino-ethyl}amine Tris(trifluoroacetate) (14i). N-(2-aminoethyl)-N'-[(2-aminoethyl)aminoethyl)]-1,2-ethanediamine (11l) (0.20 g, 1.06 mmol) was added to a stirred solution of indenobenzopyran 4d (0.58 g, 2.32 mmol) in $CHCl_3$ (150 mL) and the reaction mixture was stirred under reflux for 4 days, providing bisindenoisoquinoline 12l as a crude intermediate. Upon allowing the reaction mixture to cool to room temperature, $Et_3N$ (0.86 mL, 6.13 mmol) and $Boc_2O$ (0.89 g, 4.09 mmol) were added and the mixture was allowed to stir at room temperature for 12 h. The crude reaction mixture was purified by flash column chromatography ($SiO_2$/20% EtOAc in hexane, then 1-3% MeOH in $CHCl_3$) to provide Boc-protected bisindenoisoquinoline 13e (0.61 g, 61%), which was further treated with neat $CF_3COOH$ (30 mL) and stirred at room temperature for 3 h. The reaction mixture was concentrated and the resultant solid was diluted with chloroform (50 mL) and filtered through a sintered glass funnel to provide bisindenoisoquinoline 14i (0.42 g, 66%) as red solid: mp 198-200° C. (dec). $^1$H NMR (DMSO-$d_6$) δ 8.55 (d, J=8.1 Hz, 2 H), 8.20 (d, J=7.6 Hz, 2 H), 7.85-7.76 (m, 4 H), 7.59-7.48 (m, 8 H), 4.81 (bs, 4 H), 3.54 (bs, 4 H), 3.32 (bs, 8 H); ESIMS m/z (rel intensity) 650 (MH$^+$, 100). Anal. Calcd for $C_{46}H_{38}N_5O_{10}F_9$.0.6 $CH_2Cl_2NH_3$: C, 53.15; H, 3.93; N, 7.45. Found: C, 53.16; H, 4.27; N, 7.81.

Bis-1,2-{(5,6-dihydro-5,11-diketo-11H-indeno[1,2-c]iso-quinoline)-6-ethylamino-ethylamino}ethane Tetra(trifluoro-acetate) (14j). N,N'-Bis{(2-aminoethyl)aminoethyl)}-1,2-ethanediamine (11m) (0.20 g, 0.86 mmol) was added to a stirred solution of indenobenzopyran 4d (0.47 g, 1.89 mmol) in $CHCl_3$ (150 mL) and the reaction mixture was stirred under reflux for 4 days, providing bisindenoisoquinoline 12m as a crude intermediate. Upon allowing the reaction mixture to cool to room temperature, $Et_3N$ (1.21 mL, 8.67 mmol) and $Boc_2O$ (0.95 g, 4.34 mmol) were added to the reaction mixture and the mixture was allowed to stir at room temperature for 12 h. The crude reaction mixture was purified by flash column chromatography ($SiO_2$/20% EtOAc in hexane, then 1-3% MeOH in $CHCl_3$) to provide Boc-protected bisindenoisoquinoline 13f (0.62 g, 66%), which was further treated with neat $CF_3COOH$ (30 mL) and stirred at room temperature for 3 h. The reaction mixture was concentrated and the resultant solid was diluted with chloroform (50 mL) and filtered through a sintered glass funnel to provide bisindenoisoquinoline 14j (0.48 g, 49%) as red solid: mp 206-208° C. (dec). $^1$H NMR (DMSO-$d_6$) δ 8.55 (t, J=8.4 Hz, 2 H), 8.19 (t, J=8.0 Hz, 2 H), 7.82-7.61 (m, 4 H), 7.59-7.51 (m, 8 H), 4.81. (bs, 4 H), 3.52 (bs, 4 H), 3.27 (bs, 4 H), 3.19-3.13 (bs, 8 H); ESIMS m/z (rel intensity) 693 (MH$^+$, 100). Anal. Calcd for $C_{50}H_{44}N_6O_{12}F_{12}$.0.6$H_2O$: C, 51.78; H, 3.93; N, 7.25. Found: C, 51.41; H, 4.17; N, 7.53.

Bis-1,3-{(5,6-dihydro-5,11-diketo-2,3-dimethoxy-11H-indeno[1,2-c]isoquinoline)-6-ethylamino}propane Bis{trifluoroacetate) (14k). N,N'-Bis(2-aminoethyl)-1,3-propanediamine (11g) (0.050 g, 0.309 mmol) was added to a solution of 2,3-dimethoxybenz[d]indeno[1,2-b]pyran-5,11-dione (4a) (0.200 g, 0.649 mmol) in $CHCl_3$ (50 mL). The solution was heated at reflux for 72 h and cooled to room temperature. Triethylamine (0.17 mL) and $Boc_2O$ (0.270 g, 1.236 mmol) were added to the solution and stirring was continued at room temperature for 16 h. The solution was washed with water (2×25 mL) and sat NaCl (25 mL), dried over sodium sulfate, and concentrated. The crude red solid was purified by flash column chromatography ($SiO_2/CHCl_3$ to 3% MeOH in $CHCl_3$) followed by precipitation from $CH_2Cl_2$-hexanes to provide a pink solid. The obtained pink solid was diluted with trifluoroacetic acid (30 mL) and the mixture was stirred at room temperature for 16 h. The solution was concentrated, diluted with $CHCl_3$ (50 mL) and filtered to provide a red solid (0.257 g, 86%): mp 225-228° C. IR (KBr) 3437, 1652, 1553, 1513, 1429, 1268, 1204, and 1021 cm$^{-1}$; $^1$H NMR (DMSO-$d_6$) δ 7.96 (s, 2 H), 7.72-7.69 (bs, 2 H), 7.52-7.43 (m, 8 H), 4.71 (bs, 4 H), 3.92 (s, 6 H), 3.81 (s, 6 H), 3.06 (bs, 4 H), 1.99 (bs, 2 H); ESIMS m/z (rel intensity) 741 (MH$^+$, 100). Anal. Calcd for $C_{47}H_{42}F_6N_4O_{12}$.4 $H_2O$: C, 54.23; H, 54.83; N, 5.38. Found: C, 54.63; H, 4.49; N, 5.47.

Bis-1,3-{(5,6-dihydro-5,11-diketo-2,3-dimethoxy-11H-indeno[1,2-c]isoquinoline)-6-propylamino}propane Bis{trifluoroacetate) (14l). N,N'-Bis(3-aminopropyl)-1,3-propanediamine (11j) (0.058 g, 0.309 mmol) was added to a solution of indenobenzopyran 4a (0.200 g, 0.649 mmol) in $CHCl_3$ (50 mL). The solution was heated at reflux for 72 h and cooled to room temperature. Triethylamine (0.17 mL) and $Boc_2O$ (0.270 g, 1.236 mmol) were added to the solution and stirring was continued at room temperature for 16 h. The solution was washed with water (2×25 mL) and sat NaCl (25 mL), dried over sodium sulfate, and concentrated. The crude orange solid was purified by flash column chromatography ($SiO_2/CHCl_3$ to 3% MeOH in $CHCl_3$) followed by precipitation from EtOAc to provide an orange solid. The obtained orange solid was diluted with trifluoroacetic acid (30 mL) and the mixture was stirred at room temperature for 16 h. The solution was concentrated, diluted with $CHCl_3$ (50 mL) and filtered to provide a red solid (0.221 g, 72%): mp 273-276° C. (dec). IR (KBr) 3436, 1639, 1553, 1512, 1478, 1429, 1267, 1184, and 1022 cm$^{-1}$; $^1$H NMR (DMSO-$d_6$) δ 8.43 (bs, 4 H), 8.00 (s, 2 H), 7.76 (d, J=7.58 Hz, 2 H), 7.59-7.45 (m, 8 H), 4.56 (bs, 4 H), 3.93 (s, 6 H), 3.85 (s, 6 H), 3.09 (bs, 4 H), 2.98 (bs, 4 H), 2.15 (bs, 4 H), 1.86 (bs, 2 H); ESIMS m/z (rel intensity) 769 (MH$^+$, 100). Anal. Calcd for $C_{49}H_{46}F_6N_4O_{12}$.6 $H_2O$: C, 53.26; H, 5.29; N, 5.07. Found: C, 52.88; H, 4.96; N, 5.21.

Bis-1,3-{(5,6-dihydro-5,11-diketo-3-nitro-11H-indeno[1,2-c]isoquinoline)-6-ethylamino}propane Bis{trifluoroacetate) (14m). N,N'-Bis(2-aminoethyl)-1,3-propanediamine (11g) (0.056 g, 0.349 mmol) was added to a solution of indenobenzopyran 4c (0.225 g, 0.767 mmol) in $CHCl_3$ (50 mL). The solution was heated at reflux for 72 h and cooled to room temperature. Triethylamine (0.19 mL) and $Boc_2O$ (0.305 g, 1.396 mmol) were added to the solution and stirring was continued at room temperature for 16 h. The solution was washed with water (2×30 mL) and sat NaCl (30 mL), dried over sodium sulfate, and concentrated. The crude orange solid was purified by flash column chromatography (SiO$_2$/CHCl$_3$ to 3% MeOH in CHCl$_3$) to provide an orange solid. The orange solid was diluted with trifluoroacetic acid (40 mL) and the mixture was stirred at room temperature for 24 h. The solution was concentrated, diluted with CHCl$_3$ (50 mL) and filtered to provide an orange solid (0.221 g, 67%): mp 227-230° C. (dec). IR (KBr) 3433, 3087, 3022, 2819, 1679, 1615, 1560, 1505, 1429, 1138, and 1200 cm$^{-1}$; $^1$H NMR (CDCl$_3$) δ 8.90 (bs, 4 H), 8.79 (d, J=9.14 Hz, 2 H), 8.66 (d, J=9.07 Hz, 2 H), 7.93 (d, J=6.54 Hz, 2 H), 7.74 (d, J=7.17 Hz, 2 H), 7.67 (m, 4 H), 4.87 (bs, 4 H), 3.49 (bs, 4 H), 3.09 (bs, 4 H), 1.91 (bs, 2 H); ESIMS m/z (rel intensity) 711 (MH$^+$, 100). Anal. Calcd for C$_{43}$H$_{32}$F$_6$N$_6$O$_{12}$.0.5H$_2$O: C, 54.49; H, 3.51; N, 8.87. Found: C, 54.24; H, 3.80; N, 8.86.

Bis-1,3-{(5,6-dihydro-5,11-diketo-3-nitro-11H-indeno[1,2-c]isoquinoline)-6-propylamino}propane Bis{trifluoroacetate} (14n). N,N'-Bis(3-aminopropyl)-1,3-propanediamine (11j) (0.064 g, 0.341 mmol) was added to a solution of indenobenzopyran 4c (0.200 g, 0.682 mmol) in CHCl$_3$ (75 mL). The solution was heated at reflux for 72 h and cooled to room temperature. Triethylamine (0.19 mL) and Boc$_2$O (0.298 g, 1.364 mmol) were added to the solution and stirring was continued at room temperature for 16 h. The solution was washed with water (2×30 mL) and sat NaCl (30 mL), dried over sodium sulfate, and concentrated. The crude orange solid was purified by flash column chromatography (SiO$_2$/CHCl$_3$ to 3% MeOH in CHCl$_3$) to provide an orange solid. The obtained orange solid was diluted with trifluoroacetic acid (40 mL) and stirred at room temperature for 2 h. The solution was concentrated, diluted with CHCl$_3$ (50 mL) and filtered to provide an orange solid (0.206 g, 62%): mp 220-223° C. IR (KBr) 1678, 1614, 1505, 1339, 1203, and 1132 cm$^{-1}$; $^1$H NMR (CDCl$_3$) δ 8.88 (d, J=2.5 Hz, 2 H), 8.75 (d, J=9.0 Hz, 2 H), 8.63 (bs, 2 H), 8.60 (dd, J=9.0 Hz and 2.5 Hz, 2 H), 7.92 (d, J=6.5 Hz, 2 H), 7.70-7.61 (m, 6 H), 4.64 (t, J=5.9 Hz, 4 H), 3.15 (bs, 4 H), 2.98 (bs, 4 H), 2.19 (bs, 2 H); ESIMS m/z (rel intensity) 739 (MH$^+$, 100). Anal. Calcd for C$_{45}$H$_{36}$F$_6$N$_6$O$_{12}$.3 H$_2$O: C, 52.95; H, 4.15; N, 8.23. Found: C, 53.33; H, 4.32; N, 8.60.

1,3-{6-(3-tert-Butyloxycarbonylamino-1-propyl)-5,6-dihydro-2,3-dimethoxy-8,9-methylenedioxy-5,11-dioxo-11H-indeno[1,2-c]isoquinoline}-{5',6'-dihydro-6'-[(3'-tert-butyloxycarbonylamino)-1'-propyl]-5',11'-dioxo-11'H-indeno[1,2-c]isoquinoline}propane (16a). 5 M NaOH (aq) was added slowly to a solution of indenoisoquinoline hydrochloride A (1.0 g, 1.58 mmol) in a water-chloroform solution (2:1, 250 mL), which was prepared according to Nagarajan, M.; Xiao, X.; Antony, S.; Kohlhagen, G.; Pommier, Y.; Cushman, M., Design, Synthesis, and Biological Evaluation of Indenoisoquinoline Topoisomerase I Inhibitors Featuring Polyamine Side Chains on the Lactam Nitrogen. *J. Med. Chem.* 2003, 46, 5712-5724, the disclosure of which is hereby incorporated by reference. At a pH of 7-8, the organic layer was separated and the aqueous layer was extracted with chloroform (3×100 mL). The combined organic layers were washed with water (100 mL), sat NaCl (100 mL), dried over Na$_2$SO$_4$, and concentrated. Indenobenzopyran 4d (0.43 g, 1.74 mmol) was added to a solution of the crude indenoisoquinoline triamine A (0.70 g, 1.34 mmol) in chloroform (200 mL) and the reaction mixture was heated at reflux for 4 days. The reaction mixture containing crude, unsymmetrical bisindenoisoquinoline 15a was cooled to room temperature, Et$_3$N (0.93 mL, 6.64 mmol) and Boc$_2$O (0.87 g, 3.98 mmol) were added, and the solution was allowed to stir at room temperature for 12 h. The crude reaction mixture was purified by flash column chromatography (SiO$_2$/20% EtOAc in hexane, then 1-3% MeOH in CHCl$_3$) to provide Boc-protected bisindenoisoquinoline 16a (0.72 g, 48%) as purple solid: mp 120-122° C. $^1$H NMR (CDCl$_3$) δ 8.64 (d, J=8.3 Hz, 1 H), 8.24 (d, J=5.7 Hz, 1 H), 7.94 (s, 1 H), 7.67 (t, J=7.4 Hz, 1 H), 7.58 (s, 1 H), 7.56 (s, 1 H), 7.42-7.34 (m, 5 H), 6.99 (s, 1 H), 6.05 (s, 2 H), 4.49 (bs, 2 H), 4.40 (bs, 2 H), 4.01 (s, 3 H), 3.92 (s, 3 H), 3.45 (bs, 4 H), 3.29 (bs, 4 H), 2.10 (bs, 4 H), 1.87 (m, 2 H), 1.42 (s, 18 H); ESIMS m/z (rel intensity) 953 (MH$^+$, 30), 853 (MH$^+$-Boc, 100). Anal. Calcd for C$_{54}$H$_{56}$N$_4$O$_{12}$.0.9 CHCl$_3$: C, 62.18; H, 5.41; N, 5.28. Found; C, 62.08; H, 5.36; N, 5.15.

1,3-{6-(3-Amino-1-propyl)-5,6-dihydro-2,3-dimethoxy-8,9-methylene dioxy-5,11-dioxo-11H-indeno[1,2-c]isoquinoline}-{5',6'-Dihydro-6'-(3'-amino-1'-propyl)-5',11'-dioxo-11'H-indeno[1,2-c]isoquinoline}propane Bis(trifluoroacetate) (17a). Boc-protected bisindenoisoquinoline 16a (0.55 g, 0.58 mmol) was dissolved in neat CF$_3$COOH (30 mL) and the mixture was stirred at room temperature for 3 h. The reaction mixture was concentrated and the resultant solid was diluted with chloroform (50 mL) and filtered through a sintered glass funnel to provide bisindenoisoquinoline 17a (0.43 g, 76%) as purple solid: mp 218-220° C. $^1$H NMR (DMSO-d$_6$) δ 8.65 (bs, 2 H), 8.53 (d, J=8.0 Hz, 1 H), 8.17 (d, J=7.2 Hz, 1H), 7.80-7.75 (m, 3 H), 7.55-7.50 (m, 4 H), 7.39 (s, 1 H), 7.32 (s, 1 H), 7.02 (s, 1 H), 6.18 (s, 2 H), 4.55 (bs, 2 H), 4.45 (bs, 2 H), 3.86 (s, 3 H), 3.81 (s, 3 H), 3.07-2.98 (bs, 8 H), 2.14 (bs, 4 H), 1.89 (bs, 2 H); ESIMS m/z (rel intensity) 753 (MH$^+$, 100). Anal. Calcd for C$_{48}$H$_{42}$N$_4$O$_{12}$F$_6$.3.1 H$_2$O: C, 55.61; H, 4.69; N, 5.40. Found: C, 55.24; H, 4.36; N, 5.36.

METHOD EXAMPLES

COMPARE screening. The compounds described herein were examined for antiproliferative activity against the human cancer cell lines in the National Cancer Institute screen (COMPARE screening), in which the activity of each compound was evaluated with approximately 55 different cancer cell lines of diverse tumor origins. The GI50 values (i.e., the concentration causing 50% growth inhibition) obtained with selected cell lines, along with the mean graph midpoint (MGM) values, are summarized in Table 1 and Table 2, and provide a means of comparison of the antiproliferative activity of the compounds described herein with that of other compounds, including camptothecin (S-1), oracin (S-2), and/or 5,6-dihyro-6-(3-amino-1-propyl)-5,11-dioxo-11H-indeno[1,2,c]isoquinoline (S-3). The MGM is based on a calculation of the average GI50 for all of the cell lines tested (approximately 55) in which GI50 values below and above the test range (10$^{-8}$ to 10$^{-4}$ molar) are taken as the minimum (10$^{-8}$ molar) and maximum (10$^{-4}$ molar) drug concentrations used in the screening test. Therefore, the MGM value represents an overall assessment of toxicity of the compound across numerous cell lines. The results of topoisomerase I DNA cleavage experiments are expressed semi-quantitatively and provide a means of comparison with the biological activity of other compounds, including camptothecin (S-1) (++++), oracin (S-2) (+), and/or 5,6-dihyro-6-(3-amino-1-propyl)-5,11-dioxo-11H-indeno[1,2,c]isoquinoline (S-3).

Hollow Fiber Activity. Several of the more active indenoisoquinoline analogs (5p, 5q, 5s, 5v, and 5w) and several of the most active bisindenoisoquinoline analogs (14d, 14g, 14h, and 14i) were evaluated as anticancer agents in an in vivo animal model in which polyvinylidene fluoride (PVDF) "hollow fibers" containing various cancer cell cultures were implanted intraperitoneally (IP) and subcutaneously (SC) into athymic nude mice and compounds were administered by the IP route. The effects of the compounds on the reduction of viable cancer cell mass compared to those of controls were determined. Each compound was tested in the hollow fiber assay against a panel of twelve human tumor cell lines as described previously; see, Hollingshead, M.; Plowman, J.; Alley, M.; Mayo, J.; Sausville, E., The Hollow Fiber Assay. *Contrib. Oncol.* 1999, 54, 109-120; and Plowman, J.; Carnalier, R.; Alley, M.; Sausville, E.; Schepartz, S. *Contrib. Oncol.* 1999, 54, 121-135, the disclosures of which are hereby incorporated by reference. The compounds were solubilized in 10% DMSO in saline/Tween-80® and administered intraperitoneally once daily for a total of four doses at each of two dose levels. The two doses were selected based on single dose toxicity studies for each derivative. A score of 2 was assigned each time the compound produced a 50% or greater reduction in viable cell mass compared to vehicle-treated controls. The score for each compound was summed for the intraperitoneal fibers and the subcutaneous fibers to provide the total score for each derivative as shown in Table 3 and Table 4. For comparative purposes, the score for the clinically used anticancer drug paclitaxel is provided.

Induction of DNA cleavage. The compounds described herein may be examined for induction of DNA cleavage in the 3'-end-labeled PvuII/HindIII fragment of pBluescript SK(−) phagemid DNA in the presence of top 1 (see, Kohlhagen et al. "Protein-Linked DNA Strand Breaks Induced by NSC 314622, a Novel Noncamptothecin Topoisomerase I Poison," *Mol. Pharmacol.* 1998, 54, 50-58). The cleavage patterns for the compounds described herein can be determined, along with those of comparative compounds NSC 314622 (A) (see, Kohlhagen et al., "Protein-Linked DNA Strand Breaks Induced by NSC 314622, a Novel Noncamptothecin Topoisomerase I Poison," *Mol. Pharmacol.* 1998, 54, 50-58), camptothecin (B, CPT), and NSC 706744 (C, MJ-III-65) (see, Cushman et al., "Synthesis of New Indeno[1,2-e]isoquinolines: Cytotoxic Non-Camptothecin Topoisomerase I Inhibitors," *J. Med. Chem.* 2000, 43, 3688-3698 and Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.* 2003, 63, 7428-7435).

Topoisomerase 1-Mediated DNA Cleavage Reactions Using 3'-End-labeled 161 BP Plasmid DNA. The 161 by fragment from pBluescript SK(−) phagemid DNA (Stratagene, La Jolla, Calif.) is cleaved with the restriction endonuclease Pvu II and Hind III (New England Biolabs, Beverly, Mass.) in supplied NE buffer 2 (10 µL reactions) for 1 h at 37° C., separated by electrophoresis in a 1% agarose gel made in 1×TBE buffer. The 161 by fragment is eluted from the gel slice (centrilutor by Amicon) and concentrated in a centricon 50 centrifugal concentrator (Amicon, Beverly, Mass.). Approximately 200 ng of the fragment is 3'-end-labeled at the Hind III site by fill-in reaction with [alpha-$^{32}$P]-dCTP and 0.5 mM dATP, dGTP, and dTTP, in React 2 buffer (50 mM Tris-HCl, pH 8.0, 100 mM MgCl, 50 mM NaCl) with 0.5 units of DNA polymerase I (Klenow fragment). Labeling reactions are followed by phenol-chloroform extraction and ethanol precipitation. The resulting 161 by 3'-endlabeled DNA fragment is resuspended in water. Aliquots (approximately 50,000 dpm/reaction) are incubated with topoisomerase I at 30° C. for 15 min in the presence the compounds described herein. Reactions are terminated by adding 0.5% SDS. After ethanol precipitation, the samples are resuspended in loading buffer (80% formamide, 10 mM sodium hydroxide, 1 mM sodium EDTA, 0.1% xylene cyanol, and 0.1% bromophenol blue, pH 8.0), and separated in a denaturing gel (16% polyacrylamide, 7 M urea) run at 51° C. The gel is dried and visualized by using a Phosphoimager and ImageQuant software (Molecular Dynamics, Sunnyvale, Calif.).

Topoisomerase II-Mediated DNA Cleavage Assays Using 5'-End-labeled Human C-myc DNA. A 403-base pair DNA fragment of the human c-myc gene from the junction between the first intron and the first exon is prepared by PCR between positions 2671 and 3073 using the a sense primer oligonucleotide and an antisense primer oligonucleotide, as described by Cushman et al., in U.S. Pat. No. 6,509,344. Single-end labeling of these DNA fragments is obtained by 5'-end labeling of the adequate primer oligonucleotide. Approximately 0.1 µg of the human c-myc DNA that had been restricted by XhoI and XbaI is used as template for PCR. The 5'-end-labeled DNA fragments are equilibrated with or without a drug in 1% dimethyl sulfoxide, 10 mM Tris-HCl, pH 7.5, 50 mM KCl, 5 mM MgCl$_2$, 2 mM dithiothreitol, 0.1 mM Na$_2$EDTA, 1 mM ATP, and 15 µg/mL bovine serum albumin for 5 min before addition of purified human topoisomerase II (40-70 ng) in a 10 µL final reaction volume. The reactions are performed at 37° C. for 30 min and thereafter stopped by adding 1% sodium dodecyl sulfate (SDS) and 0.4 mg/mL proteinase K (final concentrations) followed by an additional incubation at 50° C. for 30 min. Samples are ethanol-precipitated before separation of the topoisomerase II-cleaved fragments on denaturing polyacrylamide gels. The sequencing gels are made of 7% polyacrylamide in IX TBE buffer (90 mM Tris borate, 2 mM EDTA, pH 8.3). Electrophoresis is performed at 2500 V (60 W) for 2-5 h. The gels were dried and visualized using a Phosphoiniager and ImageQuant software.

DNA Cleavage Semiquantitative Analysis. One of the most abundant cleavage products (see, Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," *Cancer Res.* 2003, 63, 7428-7435) is chosen for semiquantitation using ImageQuant TL v2003.3. The rubberband baseline correction is applied with band detection sensitivity set at 90. In the case of the compounds described herein, the absolute density value for the band corresponding to the above product is compared to the value for the NSC 314622 (A). The ratio of the band density observed for the compounds described herein to the NSC 314622 band is multiplied by 100 to obtain percentages. Assignments are performed as follows: 0-25%, 0; 25-75%, +; 75-175%, ++; 175-325%, +++; camptothecin ++++.

SV40 DNA Unwinding Assay. Reaction mixtures (10 µL final volume) contain 0.3 µg supercoiled SV40 DNA in reaction buffer (10 mM Tris-HCl, pH 7.5, 50 mM KCl, 5 mM MgCl$_2$, 0.1 mM EDTA, 15 µg/mL bovine serum albumin) and 10 units of purified calf thymus topoisomerase I. Reactions are performed at 37° C. for 30 min and terminated by the addition of 0.5% SDS, and then 1.1 µL of 10× loading buffer (20% Ficol 400, 0.1 M Na$_2$EDTA pH 8, 1.0% SDS, 0.25% Bromophenol Blue) is then added and reaction mixtures are loaded onto a 1% agarose gel made in IX TBE buffer. After electrophoresis, DNA bands are stained in 10 µg/mL of ethidium bromide and visualized by transillumination with UV light (300 nm).

Additional details regarding the biological evaluation of the compounds described herein may be found in co-pending PCT/US2005/008491, the disclosure of which is incorporated herein by reference.

TABLE 1

Cytotoxicities and Topoisomerase I Inhibitory Activities of Indenoisoquinoline Analogs.

| | cytotoxicity (GI50 in μM)[a] | | | | | | | | | |
|---|---|---|---|---|---|---|---|---|---|---|
| Cmpd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
| S-1 | 0.01 | 0.03 | 0.01 | 0.01 | 0.22 | 0.02 | 0.01 | 0.04 | .0405 ± 0.0187 | ++++ |
| S-2 | 1.62 | 1.12 | 1.65 | 1.42 | 3.85 | 0.95 | 1.28 | 2.56 | 1.90 ± 0.80 | + |
| 4a | NT | 100 | 100 | 100 | 100 | 100 | 100 | 100 | 100 | ++ |
| 4b | 53.7 | >100 | >100 | >100 | >100 | >100 | >100 | >100 | 57.5 | ++ |
| 4c | 18.20 | 47.9 | >100 | 25.1 | >100 | >100 | >100 | >100 | 64.6 | 0/+ |
| 4d | >100 | >100 | >100 | >100 | >100 | >100 | >100 | >100 | >100 | 0 |
| 5a | NT | 2.45 | 6.17 | 6.61 | 5.89 | 11.0 | 4.47 | 7.08 | 6.17 | ++ |
| 5b | <0.010 | <0.010 | 2.69 | 0.30 | 2.63 | 0.023 | 2.04 | 3.02 | 0.525 | 0/+ |
| 5c | 5.62 | 6.46 | NT | 7.08 | 25.7 | 4.17 | 5.62 | >100 | 9.77 | +++ |
| 5d | 1.74 | 0.58 | 1.86 | 0.51 | 1.70 | 0.91 | 1.32 | 2.82 | 1.86 | +++ |
| 5h | 89.1 | 60.3 | >100 | 56.2 | >100 | >100 | >100 | >100 | 741 | +++ |
| 5i | 52.50 | >100 | NT | 83.2 | >100 | 58.9 | 61.7 | >100 | 74.1 | ++++ |
| 5j | >100 | 36.3 | 85.1 | 29.5 | 81.3 | 93.3 | >100 | >100 | 67.6 | ++++ |
| 5e | <0.010 | <0.010 | <0.010 | <0.010 | <0.010 | <0.010 | <0.010 | 0.014 | 0.033 | +++ |
| 5f | 0.19 | 0.274 | 0.016 | 0.012 | 0.864 | 0.015 | 0.017 | 2.17 | 0.370 ± 0.28 | ++++ |
| 5g | 2.69 | 1.41 | 2.34 | 0.79 | 1.66 | 1.66 | 1.41 | 2.75 | 1.86 | +++++ |
| 5l | <0.010 | <0.010 | 0.037 | <0.010 | 0.085 | <0.010 | <0.010 | 0.020 | 0.079 ± 0.023 | ++++ |
| 5m | 0.447 | 1.99 | 0.398 | 0.269 | 56.2 | 0.316 | 0.363 | 7.08 | 2.16 ± 0.24 | ++ |
| 5n | 0.079 | 1.91 | 0.288 | <0.010 | 61.7 | 0.085 | 0.085 | >100 | 3.55 | +++ |
| 5o | <0.010 | <0.010 | <0.010 | 0.014 | 0.041 | <0.010 | <0.010 | <0.010 | 0.112 ± 0.066 | ++++ |
| 5p | <0.005 | 0.575 | <0.005 | 1.20 | 2.04 | 0.091 | 0.015 | 4.57 | 0.382 ± 0.119 | ++ |
| 5q | 1.78 | 1.15 | 0.040 | 0.030 | 74.1 | 0.813 | 0.155 | 67.6 | 4.64 ± 1.25 | ++++ |
| 5r | 26.3 | 72.4 | 18.2 | 37.2 | 34.7 | NT | >100 | >100 | 50.1 | ++ |
| 5s | <0.005 | <0.005 | <0.010 | 5.01 | 5.75 | 0.126 | <0.005 | 0.977 | 0.243 ± 0.088 | +++ |
| 5t | 18.2 | 1.48 | 17.8 | 15.1 | 15.1 | 11.5 | 10.7 | >100 | 12.0 | + |
| 5u | 0.427 | 0.120 | 0.100 | 1.29 | 0.832 | 0.257 | 0.182 | 1.74 | 0.766 ± 0.254 | + |
| 5v | <0.005 | 0.214 | 0.145 | 0.457 | 5.01 | 0.145 | 0.081 | 2.63 | 0.715 ± 0.335 | +++ |
| 5w | 9.77 | 2.34 | 1.44 | 1.23 | 15.1 | >100 | 0.275 | >100 | 7.86 ± 0.27 | ++ |
| 5x | <0.005 | <0.005 | 0.550 | 0.162 | 0.525 | 1.48 | 0.603 | 1.95 | 1.27 ± 0.84 | +++ |
| 5z | 24.5 | >50.1 | 28.2 | >50.1 | >50.1 | >50.1 | >50.1 | >50.1 | 39.8 | 0 |
| 5af | NT | 17.4 | 20.9 | 20.0 | 33.9 | 74.1 | 31.6 | 81.3 | 30.9 | 0 |
| 5ag | 10.7 | 25.7 | 8.71 | 15.5 | — | >50.1 | >50.1 | >50.1 | 19.9 | 0 |
| 5ah | 24.5 | NT | 17.8 | 17.4 | 28.8 | 77.6 | >100 | >100 | 50.1 | − |
| 5ai | 28.8 | 60.3 | 42.7 | 43.6 | >100 | >100 | 97.7 | >100 | 52.5 | 0 |
| 5aj | 20.9 | 35.5 | 29.5 | 24.0 | 70.8 | >100 | 91.2 | >100 | 42.6 ± 5.35 | − |
| 5ak | 32.4 | >100 | 20.4 | 27.5 | >100 | >100 | 91.2 | >100 | 51.3 | − |
| 5al | 0.620 | 0.270 | 0.210 | 0.920 | 0.710 | 0.490 | 0.760 | 0.920 | 0.530 ± 0.320 | +++ |
| 5am | 0.200 | 0.180 | 0.25 | 0.26 | 1.38 | 0.160 | 0.22 | 0.78 | 0.32 ± 0.23 | +++ |
| 5an | 0.08 | 0.10 | 0.10 | 0.05 | 0.52 | 0.04 | 0.01 | 0.84 | 0.16 ± 0.01 | +++ |
| 5ao | 0.288 | 0.200 | 0.871 | 1.35 | 0.708 | 0.398 | 0.347 | 1.35 | 0.471 ± 0.054 | 0 |
| 5ap | 1.29 | 0.912 | 1.23 | 1.62 | 2.00 | 1.32 | 0.603 | 2.04 | 1.32 | ++ |
| 5aq | 1.20 | 1.26 | 1.78 | 2.00 | 1.70 | 1.66 | 0.832 | 2.24 | 1.66 ± 0.155 | 0 |
| 5ar | 2.14 | 1.66 | 2.82 | 3.80 | 3.47 | 3.47 | 3.39 | 5.62 | 3.71 | + |
| 5as | 6.76 | 6.46 | 9.77 | 9.33 | 9.55 | 8.51 | 6.03 | 9.55 | 8.13 | 0 |
| 5at | 4.79 | 2.75 | 1.82 | 13.8 | 10.7 | 3.31 | 3.47 | 11.7 | 5.50 | + |
| 5au | 2.19 | 1.91 | 2.04 | 1.70 | 2.09 | 2.00 | 4.57 | 11.0 | 5.13 | + |
| 5av | 17.0 | NT | 18.2 | 14.8 | 17.8 | 13.5 | 19.1 | 19.5 | 18.2 | 0/+ |
| 5aw | 11.2 | NT | 12.3 | 10.7 | 13.8 | 28.2 | 13.5 | 3.09 | 15.1 | 0 |
| 5ax | 7.59 | NT | 6.76 | 8.71 | 13.8 | 13.8 | 13.8 | 42.7 | 11.5 | +++ |
| 5ay | 21.4 | NT | 17.4 | 27.5 | >100 | 77.6 | 74.1 | 5.13 | 53.7 | 0 |
| 5az | 28.8 | NT | 27.5 | 89.1 | >100 | >100 | 81.3 | 4.57 | 44.7 | 0 |
| 5ba | 0.295 | 0.794 | 0.027 | <0.010 | 3.39 | <0.010 | 0.036 | 3.24 | 0.178 ± 0.012 | ++++ |
| 5bb | NT | 3.47 | >100 | >100 | >100 | >100 | >100 | >100 | 40.0 | 0 |
| 5bc | NT | NT | NT | NT | NT | NT | NT | NT | NT | +++ |
| 5bd | NT | 0.046 | 0.058 | 0.148 | 3.02 | 0.309 | 0.034 | 1.48 | 0.328 ± 0.046 | ++++ |
| 5bf | 33.9 | 26.9 | 44.7 | 75.9 | 52.5 | >100 | 61.7 | 64.6 | 38.9 | +++ |
| 5bg | <0.010 | <0.010 | 0.038 | NT | 0.028 | <0.010 | 0.014 | 0.059 | 0.048 ± 0.024 | + |
| 5bh | 7.59 | 4.90 | NT | 19.5 | 7.94 | 25.1 | 29.5 | 7.76 | 12.3 | 0 |
| 5bi | 0.021 | 0.038 | 0.095 | 0.380 | NT | 0.309 | 0.085 | 1.23 | 0.632 ± 0.029 | +++ |
| 5bj | <0.010 | <0.010 | NT | <0.010 | <0.010 | <0.010 | NT | <0.010 | 0.014 ± 0.001 | NA |
| 5bk | 1.41 | 1.26 | 1.95 | 1.58 | 2.69 | 4.07 | 2.29 | 4.68 | 2.70 ± 0.125 | + |
| 5bl | 0.031 | 0.027 | >100 | 0.200 | 1.35 | 0.229 | >100 | 1.07 | 0.296 ± 0.067 | NA |
| 5bm | <0.010 | NT | <0.010 | <0.010 | <0.010 | 0.012 | <0.010 | <0.010 | 0.016 | ++++ |
| 5bn | 0.026 | 0.044 | 0.112 | 0.550 | 0.417 | 0.158 | 0.055 | 0.389 | 0.124 ± 0.014 | 0 |
| 5bo | 0.195 | NT | 0.550 | 0.178 | 0.550 | 0.269 | 0.174 | 0.490 | 0.339 | NA |
| 5bp | <0.010 | <0.010 | <0.010 | <0.010 | 0.028 | <0.010 | <0.010 | <0.010 | 0.020 ± 0.001 | NA |
| 5bq | 0.078 | 0.102 | 0.240 | 1.00 | 0.427 | 0.245 | 0.257 | 0.617 | 0.300 ± 0.072 | 0 |

TABLE 1-continued

Cytotoxicities and Topoisomerase I Inhibitory Activities of Indenoisoquinoline Analogs.

| Cmpd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
|---|---|---|---|---|---|---|---|---|---|---|
| 5br | <0.010 | <0.010 | <0.010 | <0.010 | 0.020 | <0.010 | <0.010 | <0.010 | 0.019 ± 0.004 | NA |
| 5bs | 0.056 | 0.110 | 0.178 | 0.071 | 1.66 | 0.676 | 0.204 | 0.646 | 0.416 ± 0.134 | +++ | cytotoxicity (GI50 in μM)[a]

[a]The cytotoxicity GI50 values are the concentrations corresponding to 50% growth inhibition.
[b]Mean graph midpoint for growth inhibition of all human cancer cell lines successfully tested.
[c]The compounds were tested at concentrations ranging up to 10 μM. The activity of the compounds to produce top 1-mediated DNA cleavage was expressed semiquantitatively as follows: +: weak activity; ++ and +++: modest activity; ++++: similar activity as 1 μM camptothecin; +++++: greater activity than 1 μM camptothecin.
NT: Not Tested;
NA: Not Available S-1 = camptothecin S-2 = oracin

TABLE 2

Cytotoxicities and Topoisomerase I Inhibitory Activities of Bis-Indenoisoquinoline Analogs.

cytotoxicity (GI50 in μM)[a]

| Cmpd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
|---|---|---|---|---|---|---|---|---|---|---|
| S-3 | 0.20 | 0.18 | 0.25 | 0.26 | 1.38 | 0.16 | 0.22 | 0.78 | 0.32 ± 0.23 | +++ |
| S-1 | 0.01 | 0.03 | 0.01 | 0.01 | 0.22 | 0.02 | 0.01 | 0.04 | .0405 ± 0.0187 | ++++ |
| 12a | >25.1 | >25.1 | >25.1 | >25.1 | >25.1 | >25.1 | >25.1 | >25.1 | 18.2 | + |
| 12c | 0.794 | 0.550 | 3.63 | 6.61 | 2.95 | 1.55 | 1.00 | 8.91 | 4.28 ± 1.89 | + |
| 12d | NT | NT | 1.12 | 2.00 | 1.20 | 0.589 | NT | 1.55 | 0.934 ± 0.476 | ++ |
| 13a | 22.4 | 22.9 | >50.1 | >50.1 | 21.4 | >50.1 | >50.1 | >50.1 | 33.9 | 0 |
| 13b | 20.0 | 14.1 | >50.1 | 45.7 | 13.2 | 39.8 | >50.1 | >50.1 | 28.2 | 0 |
| 13d | 11.0 | 1.91 | 8.13 | 93.3 | 69.2 | 36.3 | 47.9 | 69.2 | 35.5 | ++ |
| 14a | 0.977 | 1.05 | 14.5 | 5.01 | 8.91 | 11.0 | 1.91 | 2.24 | 5.25 | + |
| 14b | 0.028 | 0.056 | NT | 0.513 | 0.372 | 0.132 | 0.288 | 0.562 | 0.357 ± 0.087 | + |
| 14c | 0.032 | 0.029 | NT | 0.331 | 1.66 | 0.178 | 0.182 | 1.66 | 0.427 ± 0.01 | + |
| 14d | 0.339 | <0.005 | 0.155 | 0.182 | 0.093 | <0.005 | 0.079 | 0.024 | 0.122 ± 0.064 | ++++ |
| 14e | <0.010 | <0.010 | NT | 0.052 | 1.02 | <0.010 | <0.010 | 0.933 | 0.152 ± 0.062 | ++++ |
| 14f | 12.9 | 35.5 | >100 | >100 | >100 | 15.5 | 24.0 | >100 | 44.8 ± 2.05 | 0 |
| 14g | <0.010 | <0.010 | 0.011 | 0.042 | 0.074 | <0.010 | NT | 0.107 | 0.394 ± 0.33 | ++++ |
| 14h | 0.525 | <0.005 | 0.251 | 0.562 | 0.135 | <0.005 | 0.234 | 0.676 | 0.225 ± 0.084 | +++ |
| 14i | 0.048 | 0.112 | 0.275 | 0.269 | 1.15 | 0.017 | 0.331 | 1.00 | 0.474 ± 0.143 | +++ |
| 14j | 0.977 | 0.200 | 0.012 | NT | 0.032 | NT | 0.085 | 0.126 | 0.262 ± 0.100 | ++ |
| 14k | 0.068 | 0.045 | 0.170 | 1.23 | 0.269 | 0.028 | 0.209 | 0.813 | 0.562 | ++ |
| 14l | 1.51 | 0.331 | 4.17 | 4.27 | 9.55 | 0.240 | 19.5 | 3.98 | 6.03 | ++ |
| 14m | 0.631 | 0.044 | 0.324 | 0.603 | 0.245 | 0.123 | 0.813 | 0.437 | 0.354 ± 0.184 | ++ |
| 14n | 3.02 | 1.45 | 1.17 | 1.78 | 2.29 | 1.17 | 0.912 | 3.89 | 1.50 ± 0.24 | 0 |
| A[d] | NT | 43 | >100 | 44 | 0.88 | 33 | >100 | 68 | 58.9 | ++ |
| 16a | >100 | >100 | NT | >100 | NT | >100 | NT | >100 | 68.0 | 0 |
| 17a | 0.191 | 0.022 | <0.010 | NT | <0.010 | NT | <0.010 | 0.155 | 0.046 ± 0.010 | + |

[a]The cytotoxicity GI50 values are the concentrations corresponding to 50% growth inhibition.
[b]Mean graph midpoint for growth inhibition of all human cancer cell lines successfully tested.
[c]The compounds were tested at concentrations ranging up to 10 μM. The activity of the compounds to produce top1-mediated DNA cleavage was expressed semi-quantitatively as follows: + & ++: weak activity; +++: similar activity as compound S-3; ++++: similar activity as 1 μM camptothecin;
NT: Not Tested.
S-1 = camptothecin;
S-3 = 5,6-dihydro-6-(3-amino-1-propyl)-5,11-dioxo-11 H-indeno[1,2,c]isoquinoline (NSC 725671).
[d]A = 5,6-dihydro-2,3-dimethoxy-8,9-methylenedioxy-6-(3-aminopropylaminopropylamino-1-propyl)-5,11-dioxo-11H-indeno[1,2-c]isoquinoline

TABLE 3

Hollow Fiber Activities of Indenoisoquinoline Analogs.

| Compound | IP Score[a] | SC score[a] | Total score | Cell kill[b] |
|---|---|---|---|---|
| 5p | 16 | 2 | 18 | N |
| 5q | 4 | 2 | 6 | N |
| 5s | 6 | 0 | 6 | N |
| 5v | 12 | 2 | 14 | N |
| 5w | 8 | 0 | 8 | N |
| Paclitaxel | 24 | 8 | 32 | Y |

[a]The IP and SC scores listed are the sums of all the IP and SC scores for each compound.
[b]A net cell kill at one or more implant sites is indicated with a Y.

TABLE 4

Hollow Fiber Activities of Bis-Indenoisoquinoline Analogs.

| Compound | IP Score[a] | SC score[a] | Total score | Cell kill[b] |
|---|---|---|---|---|
| 14d | 2 | 4 | 6 | N |
| 14g | 26 | 6 | 32 | N |
| 14h | 12 | 4 | 16 | N |
| 14i | 10 | 6 | 16 | N |
| Paclitaxel | 24 | 8 | 32 | Y |

[a]The IP and SC scores listed are the sums of all the IP and SC scores for each compound.
[b]A net cell kill at one or more implant sites is indicated with a Y.

The invention claimed is:

1. A process for preparing a compound of the formula

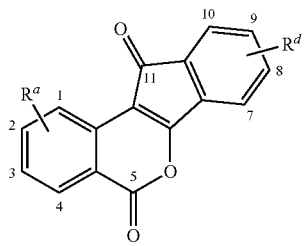

without isolating an intermediate product, the process comprising: reacting a compound of the formula

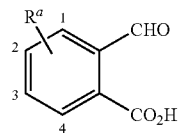

with a compound of the formula

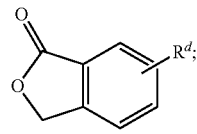

and
cyclizing the intermediate product
wherein
$R^a$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof;

$R^d$ represents 1-4 substituents each of which is independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted alkyl, optionally substituted alkoxy, cyano, nitro, optionally substituted alkylthio, optionally substituted alkylsulfonyl, carboxylic acid and derivatives thereof, and sulfonic acid and derivatives thereof.

2. The process of claim 1 wherein the cyclizing step includes one or more acids.

3. The process of claim 1 wherein $R^a$ represents a 3-nitro substituent and $R^d$ represents a 9-methoxy substituent.

* * * * *

UNITED STATES PATENT AND TRADEMARK OFFICE
CERTIFICATE OF CORRECTION

| | | |
|---|---|---|
| PATENT NO. | : 9,217,010 B2 | Page 1 of 1 |
| APPLICATION NO. | : 14/339766 | |
| DATED | : December 22, 2015 | |
| INVENTOR(S) | : Mark S. Cushman | |

It is certified that error appears in the above-identified patent and that said Letters Patent is hereby corrected as shown below:

In column 1, lines 22-25 should read:

This invention was made with government support under Grant Nos. CA089566 and CA009634 awarded by the National Institutes of Health. The government has certain rights in this invention Signed and Sealed this
Fifth Day of April, 2016

Michelle K. Lee
*Director of the United States Patent and Trademark Office*